United States Patent
Rogowski et al.

(10) Patent No.: US 12,410,237 B2
(45) Date of Patent: Sep. 9, 2025

(54) METHODS FOR PURIFYING PROTEINS HAVING A TUBULIN CARBOXYPEPTIDASE ACTIVITY AND PEPTIDIC BASED INHIBITORS THEREOF

(71) Applicants: CENTRE NATIONAL DE LA RECHERCHE SCIENTIFIQUE, Paris (FR); UNIVERSITÉ DE MONTPELLIER, Montpellier (FR)

(72) Inventors: Krzysztof Rogowski, Montpellier (FR); Siem Van Der Laan, Cazilhac (FR)

(73) Assignees: CENTRE NATIONAL DE LA RECHERCHE SCIENTIFIQUE, Paris (FR); UNIVERSITÉ DE MONTPELLIER, Montpellier (FR)

( * ) Notice: Subject to any disclaimer, the term of this patent is extended or adjusted under 35 U.S.C. 154(b) by 221 days.

(21) Appl. No.: 16/631,849

(22) PCT Filed: Jul. 18, 2018

(86) PCT No.: PCT/EP2018/069496
§ 371 (c)(1),
(2) Date: Jan. 17, 2020

(87) PCT Pub. No.: WO2019/016259
PCT Pub. Date: Jan. 24, 2019

(65) Prior Publication Data
US 2020/0172598 A1    Jun. 4, 2020

(30) Foreign Application Priority Data
Jul. 18, 2017 (EP) .................................... 17305954

(51) Int. Cl.
| | | |
|---|---|---|
| *C07K 14/81* | (2006.01) | |
| *A61K 38/00* | (2006.01) | |
| *A61K 38/05* | (2006.01) | |
| *A61K 38/06* | (2006.01) | |
| *A61K 38/07* | (2006.01) | |
| *A61K 38/08* | (2019.01) | |
| *A61K 38/10* | (2006.01) | |
| *A61P 21/00* | (2006.01) | |
| *A61P 25/28* | (2006.01) | |
| *C07K 1/14* | (2006.01) | |
| *C12N 9/48* | (2006.01) | |
| *C12Q 1/37* | (2006.01) | |

(52) U.S. Cl.
CPC .......... *C07K 14/8103* (2013.01); *A61K 38/05* (2013.01); *A61K 38/06* (2013.01); *A61K 38/07* (2013.01); *A61K 38/08* (2018.01); *A61K 38/10* (2013.01); *A61P 21/00* (2018.01); *A61P 25/28* (2018.01); *C07K 1/14* (2013.01); *C12N 9/485* (2013.01); *C12Q 1/37* (2013.01); *C12Y 304/17017* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 4,837,219 A | * | 6/1989 | Hutterer | A61K 31/315 514/561 |
| 2004/0001899 A1 | * | 1/2004 | Bennett | A61K 31/015 514/474 |
| 2004/0048327 A1 | * | 3/2004 | Powers | C07D 303/48 530/331 |
| 2006/0154312 A1 | * | 7/2006 | Agoulnik | G01N 33/5091 514/450 |
| 2007/0088074 A1 | * | 4/2007 | Martynyuk | A61K 31/198 514/567 |
| 2009/0137473 A1 | | 5/2009 | Martin et al. | |
| 2015/0111878 A1 | * | 4/2015 | Hoffman | A61P 19/02 514/567 |

FOREIGN PATENT DOCUMENTS

| | | | | |
|---|---|---|---|---|
| WO | WO-9611009 A1 | * | 4/1996 | ............ A61K 31/00 |
| WO | WO-9832464 A1 | * | 7/1998 | ............ A61K 33/26 |

OTHER PUBLICATIONS

Pepscan, "C-terminal modifications," available online at https://www.pepscan.com/custom-peptide-synthesis/peptide-modifications/c-terminal-modifications/, 5 pages (2015) (Year: 2015).*
Schiefer et al., J. Med. Chem. 56:6054-6068 (2013) (Year: 2013).*
National Institute of Neurological Disorders and Stroke, "Parkinson's Disease," National Institute of Neurological Disorders and Stroke, available online at www.ninds.nih.gov/health-information/disorders/parkinsons-disease#, 10 pages (accessed on Feb. 9, 2024) (Year: 2024).*
Kerr et al., Nat. Commun. 6:8526 (2015) (Year: 2015).*
Warner et al., Cir. Res. 130:1723-1741 (2022) (Year: 2022).*
Magiera et al., Cell 173:1323-1327 (2018) (Year: 2018).*
McKenna et al., Annu. Rev. Cell Dev. Biol. 39:331-361 (2023) (Year: 2023).*
Lopes et al., Cells 9:17 pages (2020) (Year: 2020).*

(Continued)

*Primary Examiner* — Thea D' Ambrosio
(74) *Attorney, Agent, or Firm* — SALIWANCHIK, LLOYD & EISENSCHENK

(57) ABSTRACT

The invention relates to a method for purifying proteins having a tubulin carboxypeptidase activity from a biological extract, comprising polymerization/depolymerization cycle performed on a biological extract in presence of microtubules. The invention further relates to a peptidic based inhibitor for use in the treatment of a disorder involving altered microtubule detyrosination in an animal, wherein the peptidic based inhibitor comprises a peptidic moiety constituted of 1 to 20 amino acids, said peptidic moiety having an amino acid selected from Y or F at the C-terminal position, and wherein the peptidic based inhibitor inhibits at least partially a tubulin carboxypeptidase activity.

Figure 1:
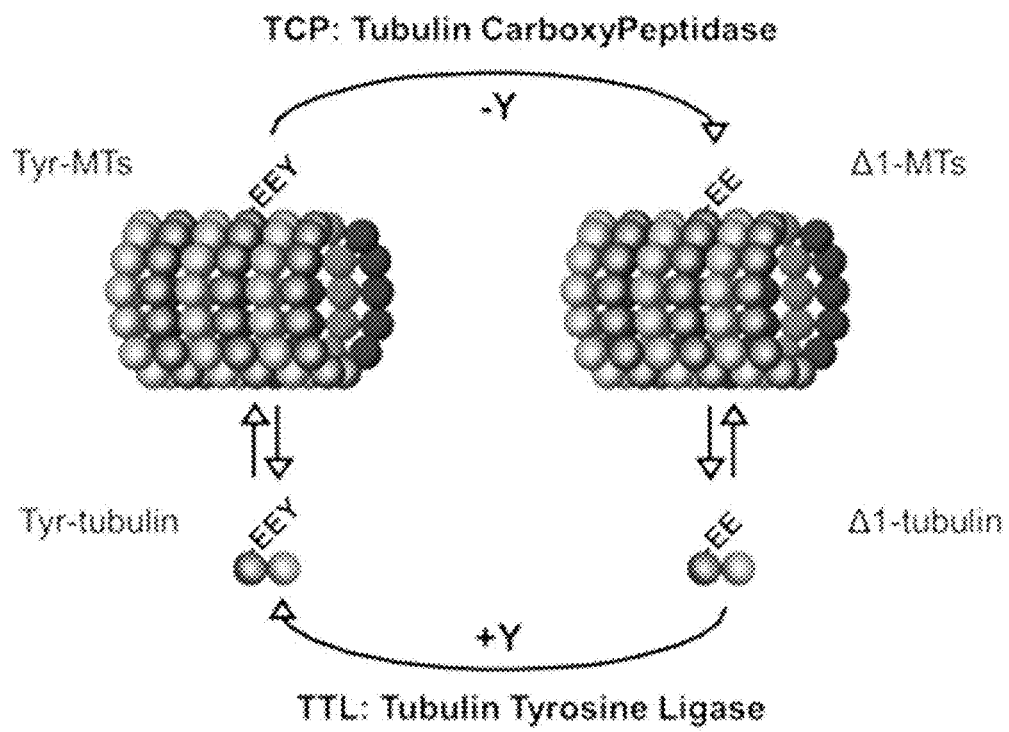

6 Claims, 11 Drawing Sheets
Specification includes a Sequence Listing.

(56) References Cited

OTHER PUBLICATIONS

Libre Texts™, "7.1: Properties of Amino acids", LibreTexts™, available online at https://chem.libretexts.org/Courses/Indiana_Tech/EWC%3A_CHEM_2300_-_Introductory_Organic_(Budhi)/7%3A_Amino_Acids_Proteins_and_Enzymes/7.01%3A_Properties_of_Amino_Acids, 4 pages (accessed on Jan. 8, 25) (Year: 2025).*

Bosson, A et al. "Cap-Gly Proteins at Microtubule Plus Ends: Is EB1 Detyrosination Involved?" *PLoS ONE*, Mar. 14, 2012, pp. 1-7, vol. 7, No. 3, e33490.

Fonrose, X. et al. "Parthenolide Inhibits Tubulin Carboxypeptidase Activity" *Cancer Research*, Apr. 1, 2007, pp. 3371-3378, vol. 67, No. 7.

Brunet-Simon, A. et al. "Onset of Zygotic Transcription and Maternal Transcript Legacy in the Rabbit Embryo" *Molecular Reproduction and Development*, Jan. 2001, pp. 127-136, vol. 58, No. 2.

Aillaud, C. et al. "Vasohibins/SVBP are tubulin carboxypeptidases (TCPs) that regulate neuron differentiation" *Science*, Dec. 15, 2017, pp. 1448-1453, pp. 1-6, vol. 358.

Written Opinion in International Application No. PCT/EP2018/069496, Sep. 14, 2018, pp. 1-5.

Van Der Laan, S. "Evolutionary Divergence of Enzymatic Mechanisms for Tubulin Detyrosination" *Cell Reports*, Dec. 17, 2019, pp. 4159-4171, supplemental pp. e1-e6 and supplemental information pp. 1-15, vol. 29.

\* cited by examiner

METHODS FOR PURIFYING PROTEINS HAVING A TUBULIN CARBOXYPEPTIDASE ACTIVITY AND PEPTIDIC BASED INHIBITORS THEREOF

CROSS-REFERENCE TO RELATED APPLICATION

This application is the U.S. national stage application of International Patent Application No. PCT/EP2018/069496, filed Jul. 18, 2018.

The Sequence Listing for this application is labeled "Seq-List-replace.txt" which was created on Feb. 11, 2020 and is 62 KB. The entire content of the sequence listing is incorporated herein by reference in its entirety.

FIELD OF THE INVENTION

The present invention relates to a method for purifying a protein having a tubulin carboxypeptidase activity in a biological extract. The invention further relates to a method for identifying a peptidic based inhibitor suitable for inhibiting a tubulin carboxypeptidase activity. The present invention also relates to the use of such peptidic based inhibitors for use in the treatment of a disorder involving defects in microtubule detyrosination in an animal, preferably a mammal.

BACKGROUND OF THE INVENTION

Microtubules (MTs) are the major types of filaments that constitute the eukaryotic cytoskeleton. They are formed by the polymerization of a dimer of two globular proteins, α- and β-tubulin heterodimers. They are involved in many different functions including intracellular transport (cargo transport), cell motility, cell division, cell morphogenesis and convey mechanical signals to intracellular effectors (mechanotransduction). The intrinsic dynamic instability of the cytoskeletal microtubular system is essential for neuronal remodelling, plasticity and adaptation. Each particular MT function requires the recruitment of a specific set of MT-associated proteins (MAPs) and molecular motors. Many MAPs and motors interact with the C-terminal tails of tubulins, which protrude from the MT surface (Ciferri et al, 2008; Mizuno et al, 2004; Roll-Mecak & Vale, 2008; Skiniotis et al, 2004). Thus, one way to adapt MTs to different functions is to change the properties of the tubulin C-terminal tails through posttranslational modifications.

Among said post-translational modifications of the tubulin C-terminal tails, two polymodifications, namely polyglutamylation and polyglycylation, occur on both α- and β-tubulin (Edde et al, 1992; Redeker et al, 1994). Polyglutamylation and polyglycylation consist of the addition of side chains composed of either glutamate or glycine residues to the primary sequence glutamates present at the C-terminus of both tubulins. Enzymes that catalyze these modifications have recently been identified (Janke et al, 2005; Rogowski et al, 2009; van Dijk et al, 2007) as well as the enzymes that remove polyglutamylation (Rogowski et al, 2010). Apart from polymodifications, also detyrosination occurs on the C-terminus but it is specific to α-tubulin (Arce et al, 1975). Detyrosination consists of the removal of the very C-terminal tyrosine from α-tubulin and it results in generation of so-called Δ1-tubulin (FIG. 1).

Up to now, the enzymes responsible for detyrosination that possess tubulin carboxypeptidase (TCP) activity are unknown. Of note, native TCP activity contained in protein extracts obtained from different tissues and/or organisms likely differ in their set of enzymes responsible for detyrosination.

The identification of specific inhibitors of enzymes with TCP activity is of particular interest for treating disorders involving microtubule detyrosination, such as neurodegenerative diseases, neuronal regeneration disorders, cancers, muscular dystrophies, heart diseases, vascular disorders, retinal degeneration, infertility or ciliopathies.

Accordingly, there is thus a need for a method allowing identification of enzymes with TCP activity and a method to allow design and identification of molecules that act on native TCP enzymatic activity.

SUMMARY OF THE INVENTION

Interestingly, the present invention proposes methods for identifying both, the enzymes that possess TCP activity and peptidic based inhibitors regardless of the original tissue and/or organism. To this end, the present invention proposes to purify TCP activity from a biological extract and to use such purified biological extract, which exhibits native TCP activity to test and identify peptidic based inhibitors. More particularly, the inventors surprisingly discovered that it is possible to exploit the natural substrate of tubulin carboxypeptidases, i.e. the very C-terminal amino acid(s) of alpha-tubulins, as moieties or backbone for modifications, to inhibit TCP activity. The peptides that share sequence homology with the C-terminal amino acid sequence of alpha-tubulins could mimic the natural substrate of enzymes that possess TCP activity and consequently inhibit its activity. More particularly, the inventors have inventively used peptides composed of variable lengths (1 to 20 amino acids) of the very C-terminal sequence of alpha-tubulin that protrudes out of the hollow tube comprised by the MT structures, to inhibit native TCP activity contained in biological extracts. Highly selective, cell permeable, reversible or irreversible (suicide ligands) modified peptides with undetectable cytotoxicity that specifically modulate TCP activity were generated. The present invention further proposes a group of chemically modified peptides that pharmacologically act on microtubule dynamics by specifically modulating TCP activity.

Since the enzymes responsible for detyrosination that possess tubulin carboxypeptidase (TCP) activity may be valuable pharmacological targets, the present invention now proposes a method for identifying enzymes responsible for detyrosination that possess tubulin carboxypeptidase (TCP) activity. To do so, the inventors originally set up a biochemical approach to isolate TCP activity contained in a biological extract followed by a specific enrichment of all proteins that could bind to microtubules. As such, the set of microtubule associated proteins (MAPs) was identified before and after the biochemical purification steps. It is thus an object of the present invention to provide a method for purifying proteins having a tubulin carboxypeptidase activity from a biological extract, comprising:

(a) centrifuging the biological extract at a temperature comprised between 0 and 10° C., preferably between 2 and 5° C., more preferably at 2° C.;

(b) recovering the supernatant from step (a) and proceeding to a first microtubule polymerization cycle by adding GTP and incubating the mixture at a temperature between 35 and 40° C., preferably at 37° C., +/−2° C., then centrifuging;

(c) recovering the pellets of step (b), resuspending in ice-cold buffer, incubating at 4° C.+/−1° C., and proceeding to a second microtubule polymerization cycle by adding GTP and incubating the mixture at 37° C., +/−2° C., then centrifuging;

(d) recovering the pellets of step (c) resuspending in ice-cold buffer, incubating at 4° C.+/−1° C., and proceeding to a third microtubule polymerization cycle by adding GTP and incubating the mixture at 37° C., +/−2° C., then centrifuging;

(e) resuspending the pellets of step (d) and submitting the mixture to an ion exchange chromatography and recovering the flow through;

(f) precipitating the proteins of the flow through with a 60% saturated ammonium sulphate solution;

(g) submitting the precipitated fraction of step (f) to an hydrophobic chromatography and eluting by gradually decreasing ammonium sulphate concentration up to zero to recover the fraction of proteins with a tubulin carboxypeptidase activity.

It is a further object of the invention to provide a method for selecting a peptidic based inhibitor able to inhibit a tubulin carboxypeptidase activity among peptidic based inhibitor candidates that comprise a peptidic moiety constituted of 1 to 20 amino acids, said modified peptide having at the C-terminal position an amino acid selected from Y or F, wherein the method comprises (a) contacting the peptidic based inhibitor candidate with a mixture containing both a fraction of native or recombinant proteins with a tubulin carboxypeptidase activity and microtubules, which preferably comprise synthetic microtubules and/or α-tubulins, with labeled C-terminal Y; and (b) measuring the level of isolated Y and/or detyrosinated microtubules.

Advantageously, the fraction of proteins with a tubulin carboxypeptidase activity is obtained with the method for purifying proteins as exposed above.

In an embodiment, the microtubules comprise synthetic microtubules and/or α-tubulins, with labeled C-terminal Y.

In an embodiment, the level of isolated Y in the reaction sample is compared to the level of isolated Y in a control sample comprising solely a fraction of proteins with a tubulin carboxypeptidase activity and microtubules.

In a particular embodiment, the peptidic moiety of the peptidic based inhibitor candidate is constituted of between 1 and 20 amino acids of the most C-terminal amino acids of an alpha-tubulin.

In a particular embodiment, the peptidic moiety of the peptidic based inhibitor candidate is constituted of between 1 and 16 of the most C-terminal amino acids of the amino acid sequence Nter-X1-X2-X3-X4-X5-X6-X7-X8-X9-X10-X11-X12-X13-X14-X15-X16-Cter, wherein X1, X2, X5, X7, X9 and X13 are hydrophobic amino acids, preferably selected from G, A or V, X3, X6, X8, X10, X11, X12, X14 and X15 are negatively charged amino acids, preferably selected from E or D, X4 is an amino acid with a polar uncharged side chain, preferably selected from S, T, N or Q, and X16 is a large hydrophobic amino acid, selected from Y or F.

For instance, the peptidic moiety of the peptidic based inhibitor candidate has the amino acid sequence selected from Y, EAY, EDY and EEY.

In a particular embodiment, the peptidic based inhibitor candidate further comprises a reactive moiety, preferably selected from epoxysuccinyl, acyloxymethyl, aldehydes and ketones. In an embodiment, the reactive group is incorporated within the peptidic sequence. For instance, the reactive group is an epoxyde, which replaces the glutamate residue adjacent to the very C-terminal aromatic residue, preferably F or Y.

It is another object of the invention to provide a peptidic based inhibitor for use in the treatment of a disorder involving altered microtubule detyrosination in an animal, wherein the peptidic based inhibitor comprises or a peptidic moiety constituted of 1 to 20 amino acids, said peptidic moiety having an amino acid selected from Y or F at the C-terminal position, and wherein the peptidic based inhibitor inhibits at least partially a tubulin carboxypeptidase activity.

According to the invention, the peptidic based inhibitor inhibits irreversibly or reversibly a tubulin carboxypeptidase activity.

The disorder is preferably selected from neurodegenerative diseases, preferably selected from Alzheimer disease, Parkinson disease, psychiatric disorders, and neural disorders, neuronal regeneration disorders, cancers, preferably selected from colon cancer and neuroblastoma, muscular dystrophies, heart diseases, vascular disorders, infertility, retinal degeneration, and ciliopathies.

It is another object of the present invention to provide a pharmaceutical composition comprising a therapeutically effective amount of such peptidic based inhibitors.

FIGURES

FIG. 1: schematic overview of detyrosination and tyrosination cycle of microtubule, which consists of the removal of the very C-terminal tyrosine from α-tubulin by use of Tubulin CarboxyPeptidase (TCP) and results in generation of so-called Δ1-tubulin. Incorporation of tyrosine (Y) at the very C-terminus of the detyrosinated soluble tubulin is obtained by Tubulin tyrosine ligase (TTL).

Figure 2:
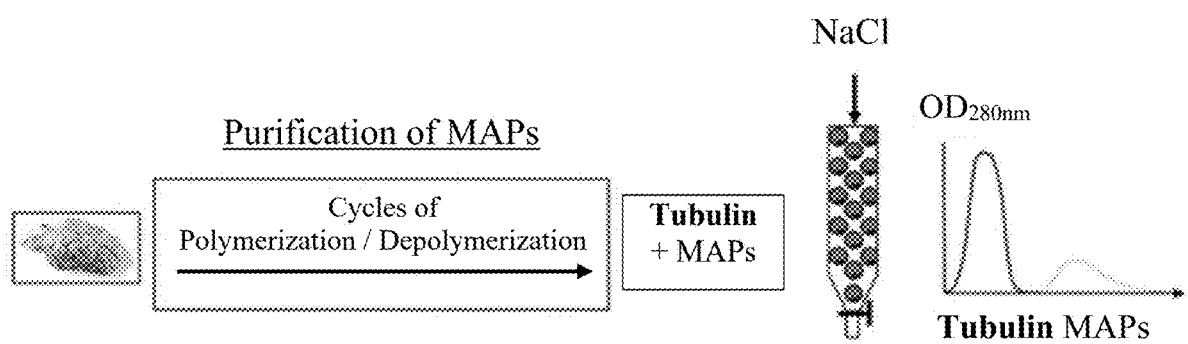

FIG. 2: isolation of native TCP activity from a brain extract by way of cycles of depolymerization/polymerization to isolate and purify Microtubule Associated Proteins (MAPs).

Figure 3:
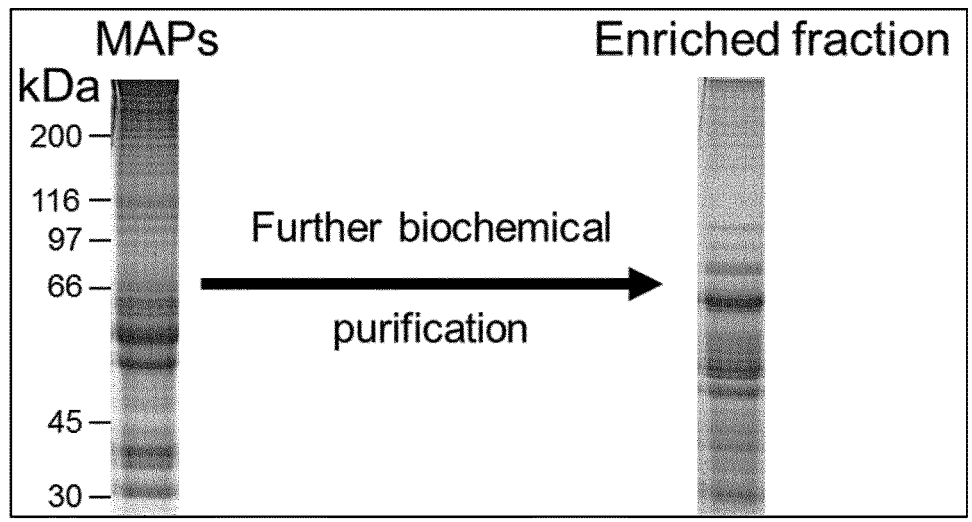

FIG. 3: biochemical isolation of MAPs before (MAPs) and after (Enriched fraction) enrichment by biochemical enrichment including ammonium sulphate precipitation and hydrophobic chromatography. (The polymerization/depolymerization method is used to get the initial MAPs. The enriched fraction is after the biochemical procedure involving ammonium sulphate and hydrophobic chromatography.)

Figure 4:
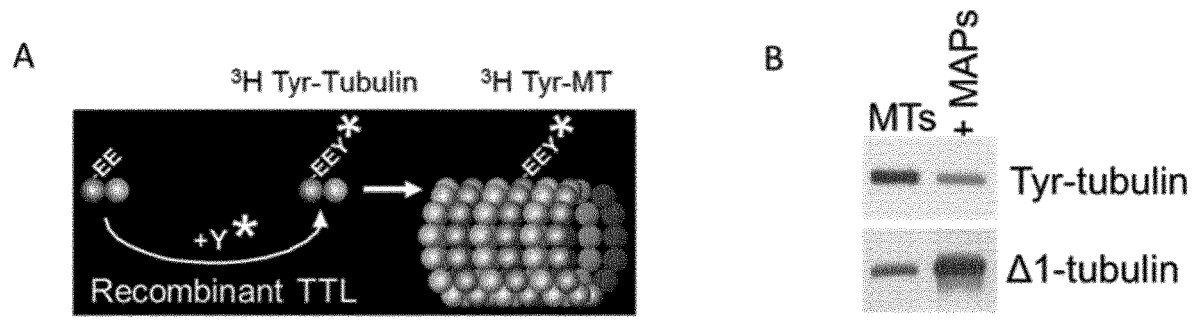

FIG. 4: (A) schematic representation of detyrosination assay wherein $^3$H Tyrosine is incorporated into soluble Tubulin by use of TTL. Following polymerization cycles $^3$H Tyr-Tubulin is incorporated in microtubules to obtain $^3$H Tyr-microtubule; (B) validation of the TCP activity contained in the isolated MAPs fraction.

Figure 5:
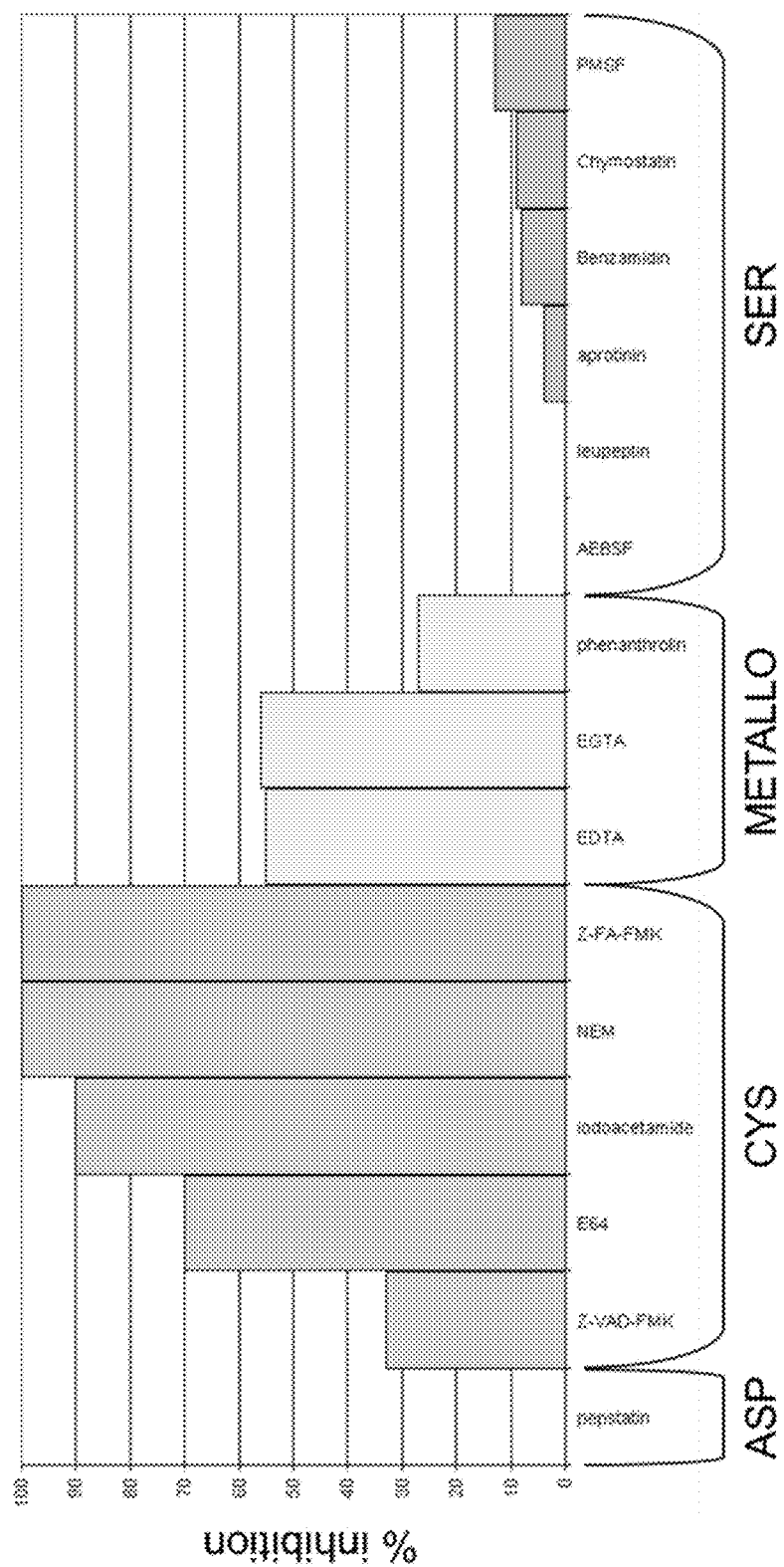

FIG. 5: inhibition of native TCP activity in brain extract by treatment with different Aspartic, Cysteine, Metallo and Serine proteases inhibitors (ASP=aspartic protease inhibitor, CYS=cysteine protease inhibitors, METALLO=metalloprotease inhibitors, SER=serine protease inhibitors).

Figure 6:
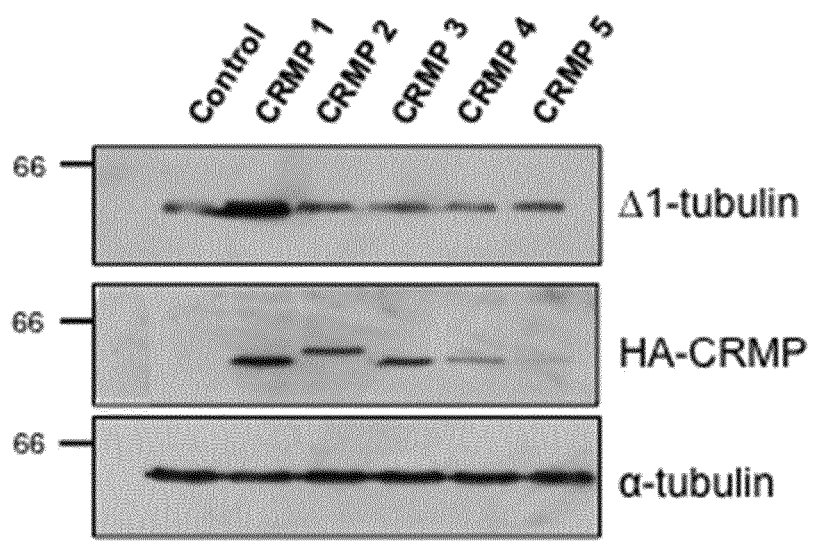

FIG. 6: Immunoblot analysis of protein extract obtained from HEK293 ectopically expressing individual CRMP family members. Δ1-tubulin represents the amounts of detyrosinated tubulin. HA displays the level of ectopically expressed CRMP members. The α-tubulin labeling served as a loading control and allows to compare the ratio of detyrosinated tubulin to total tubulin.

Figure 7:
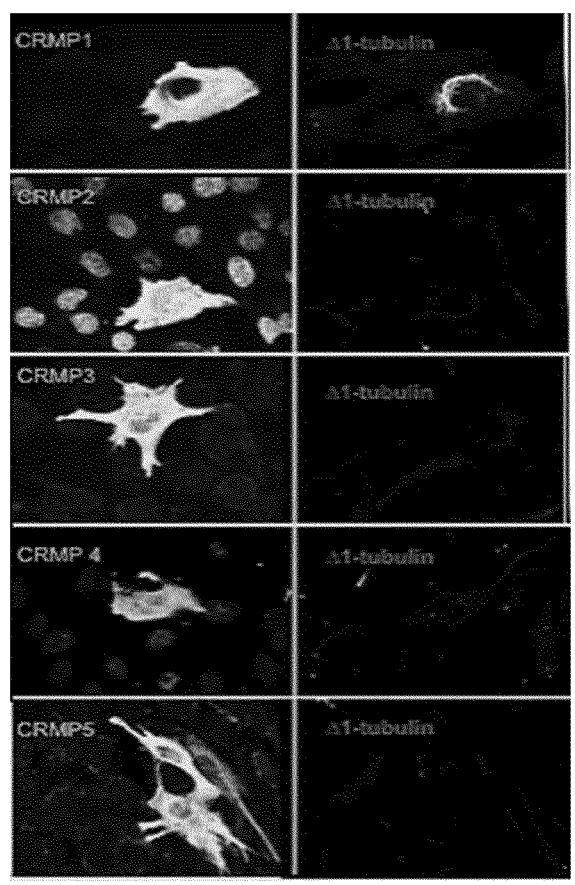

FIG. 7: Immunofluorescence analysis of U2OS cells ectopically expressing the five members of CRMP family. The left panel displays the immunofluorescence (IF) signal for the ectopically expressed CRMPs. In the right panel the signal can be observed for detyrosinated MTs.

Figure 8:
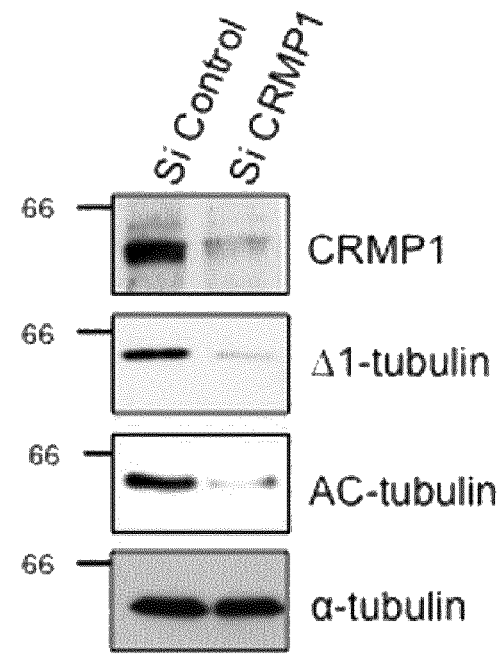

FIG. 8: Immunoblot showing specific knockdown of endogenous CRMP1 expression in U2OS cells by siRNA interference. The α-tubulin labeling serves as a loading control and allows to compare the ratio of detyrosinated tubulin to total tubulin.

Figure 9:
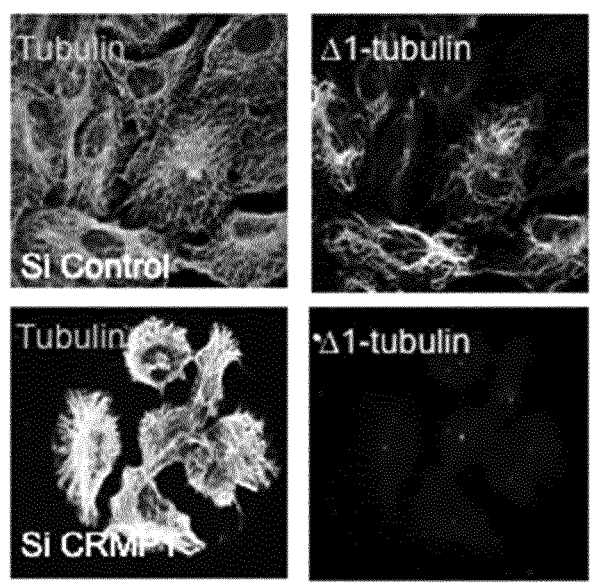

FIG. 9: Immunofluorescence analysis of U2OS cells depleted for CRMP1 protein. The left panel displays the total tubulin level per cell. On the right panel only microtubules labeled for detyrosination are staining positively.

Figure 10:
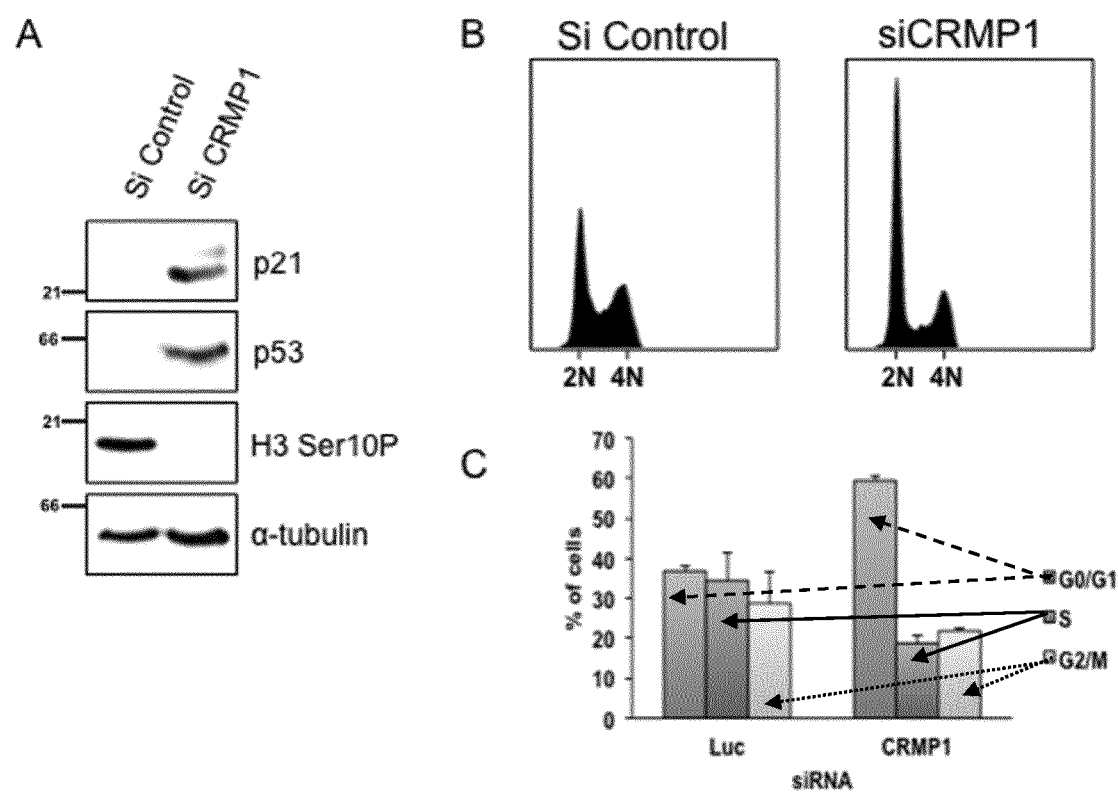

FIG. 10: (A) Immunoblot analysis of U2OS cells depleted for CRMP1 protein. Cell cycle arrest is demonstrated by accumulation of cyclin dependent kinase inhibitor p21 and its downstream effector p53 as well as decrease in the amount of phosphorylated histone 3 (serine—Ser10P). (B) Flow cytometry analysis of bulk DNA content of CRMP1 depleted U2OS cells. (C) Graphical representation of the relative number of cells in different cell cycle stages from control (Luciferase) and CRMP1 depleted U2OS cells.

Figure 11:
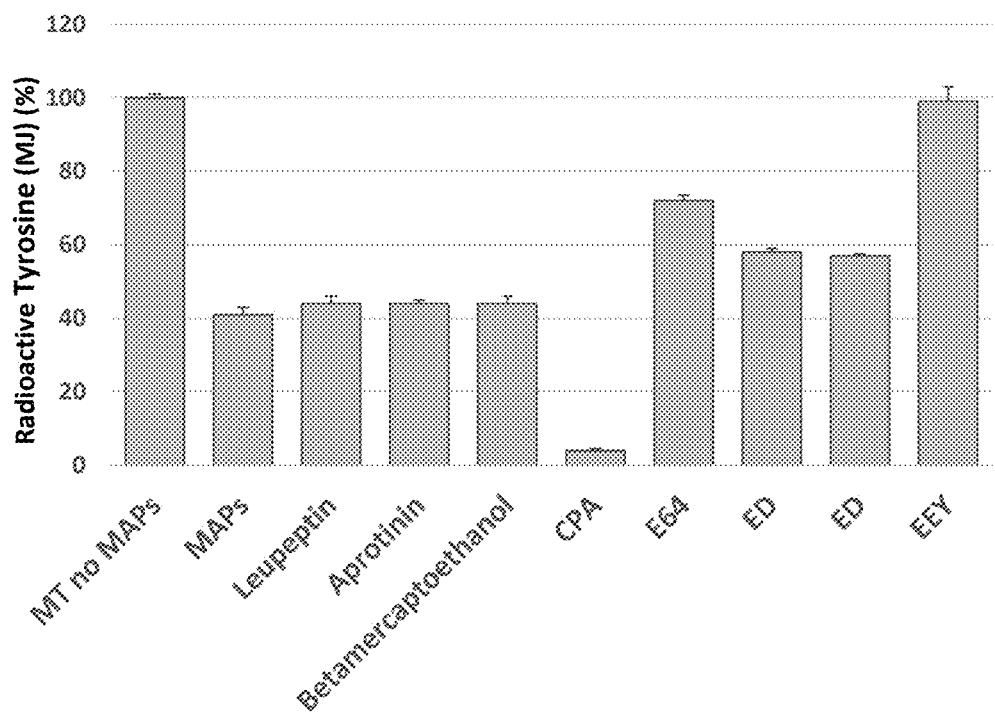
Figure 11:
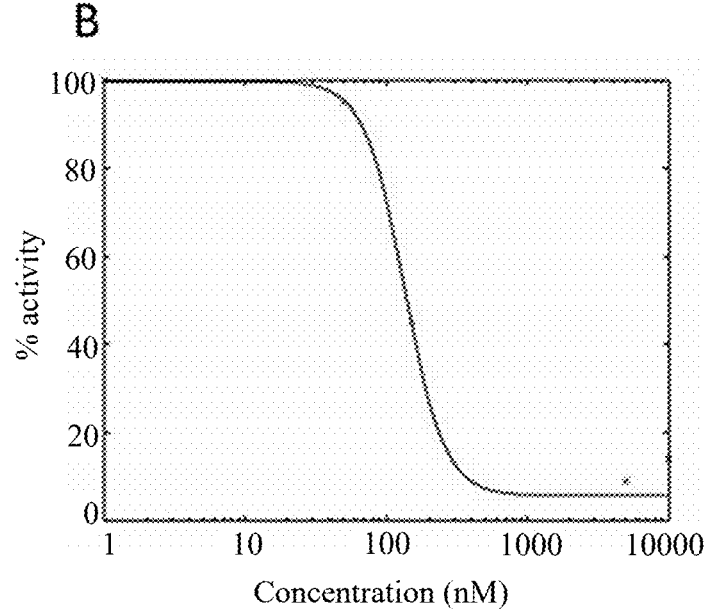

FIG. 11: (A) inhibition of native TCP activity in brain-derived MAPs resulting from incubation with various peptides inspired by the C-terminal sequence of tubulin (EDY, EEY). (B) Dose response curve of TCP activity in presence of increasing EEY concentrations.

Figure 12:
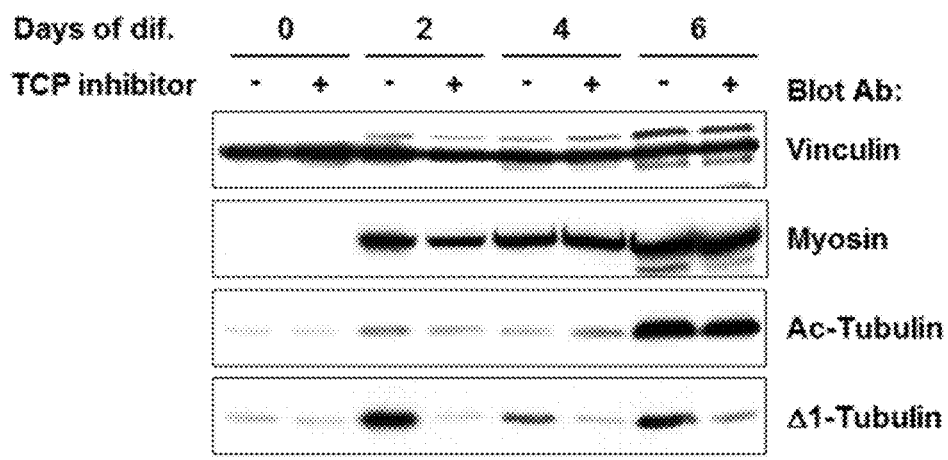

FIG. 12: C2C12 muscle differentiation model. Time-course of C2C12 cells mimicking muscle differentiation in presence or absence of the TCP inhibitor EEY. Immunoblotting analysis of protein extracts obtained from myogenic differentiation of C2C12 cells. Incubation with EEY led to decrease tubulin detyrosination levels (Δ1-tubulin).

Figure 13:
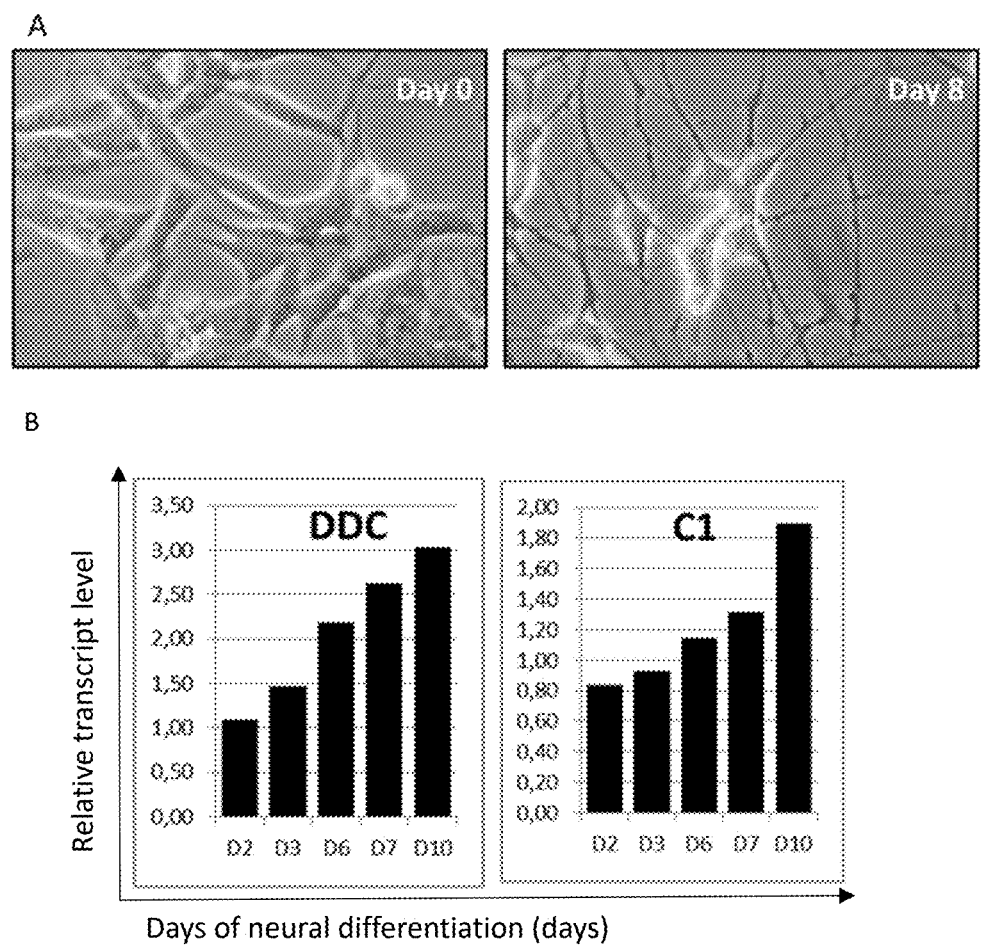

FIG. 13: SH-SY5Y neural differentiation process. (A) Phase contrast microscopy pictures of SH-SY5Y cells at Day 0 and Day 8 after neural differentiation. (B) Gene expression analysis of DDC (Aromatic-L-amino-acid decarboxylase), a marker of dopaminergic neurons and of CRMP1 (C1) expression during the neuronal differentiation process.

Figure 14:
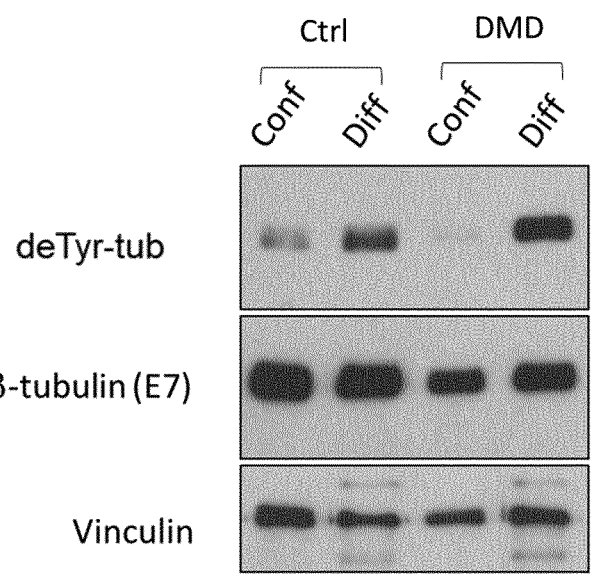

FIG. 14: Immunoblot analysis of detyrosinated tubulin (deTyr-tub) of Control and DMD cells that contain a causal genetic mutation for Duchenne Muscular Dystrophy.

Figure 15:
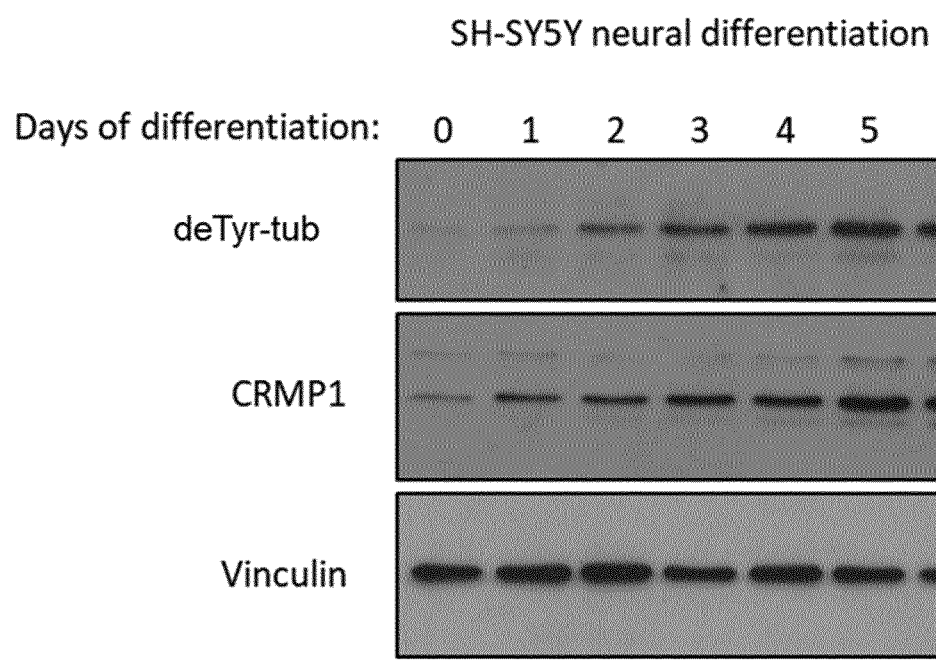

FIG. 15: Immunoblot analysis of detyrosinated tubulin (deTyr-tub) of Control and SH-SY5Y cells.

Figure 16:
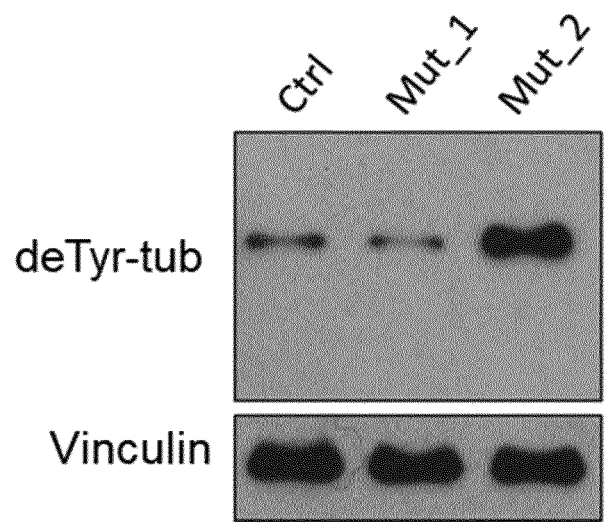

FIG. 16: Immunoblot analysis of detyrosinated tubulin (deTyr-tub) of Control and iPSC generated from skin fibroblasts from patients carrying two different familial Alzheimer's Disease mutations (Mut_1 and Mut_2).

Figure 17:
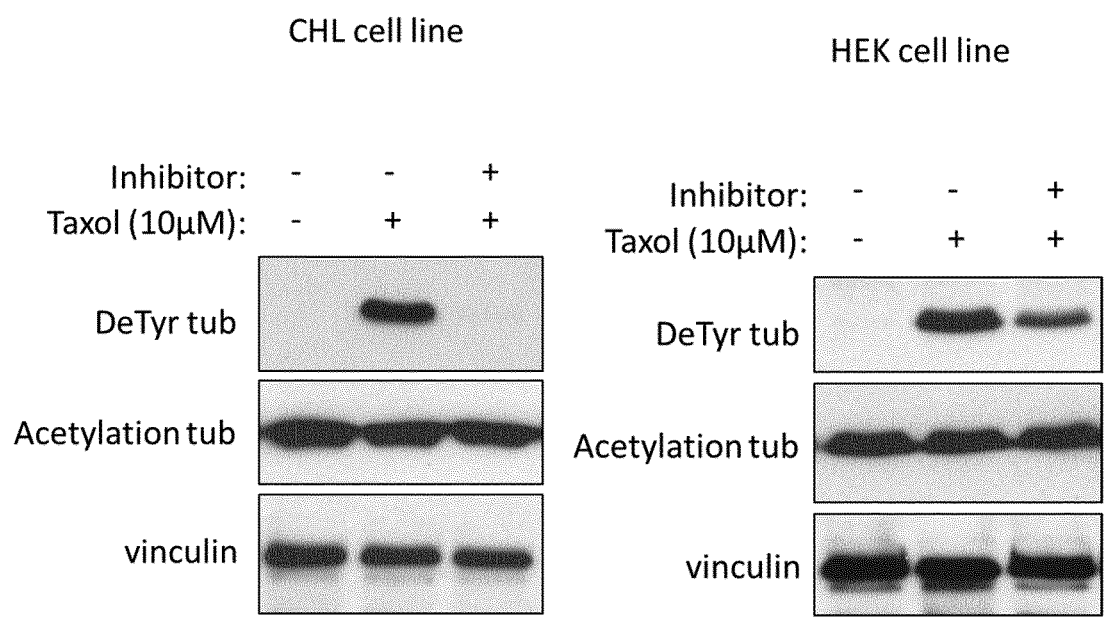

FIG. 17: Immunoblot analysis of detyrosinated tubulin (deTyr-tub) of Control and CHL-1 cells and HEK cells, in presence or absence of TCPase inhibitor (Eps-Y).

Figure 18:
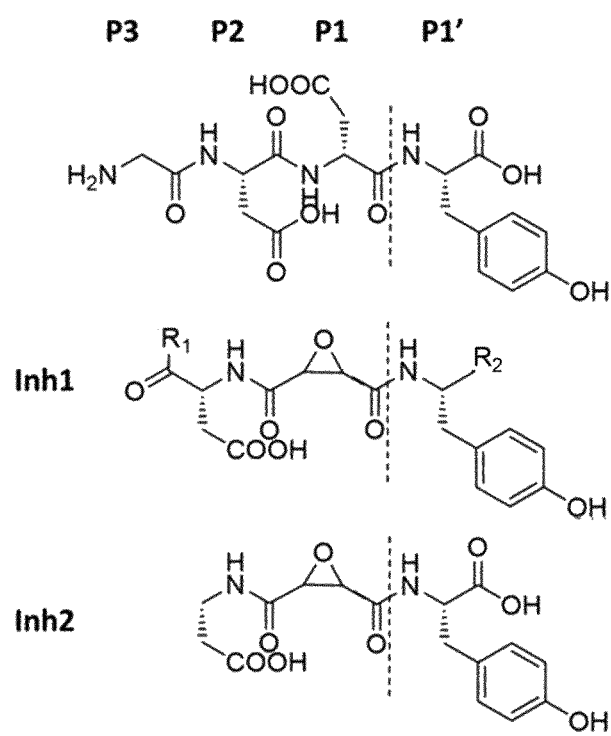

FIG. 18: Examples of peptide-based inhibitors comprising a peptidic moiety and a reactive group composed of, for example, an epoxyde group. A first general example illustrates a subtype of different inhibitors composed of a very C-terminal tyrosine (Y) attached to an epoxyde group and the C-terminal sequence of alpha tubulin such as GEepoxydeY (inh1). In the chemical formula, R1 represents the amino acid sequence of human alpha tubulin and R2 a wide variety of C-terminal modifications such as, but not limited to, COOH; CONH2, NH2, aldehyde, pNA, Amc, hydrazide, hydroxamic acid, CMK). Those modifications may contribute to preventing enzyme degradation, to mimic native proteins, and in some cases to remove hydrogen bonding at the C-terminal of the peptides, tools for studying structure-activity relationship (SAR), and more. The second molecule (inh2) represent the formula of a shorter version of the peptidic inhibitor.

DETAILED DESCRIPTION OF THE INVENTION

The present invention originally proposes to exploit the natural substrate of proteins with TCP activity, i.e., the very C-terminal sequence of α-tubulin, as pharmacological tool for inhibiting TCP activity. The inventors discovered several families of proteins possessing TCP activity in a controlled purified biochemical assay as well as in human cell cultures. In turn, the inventors have developed a method to design pharmacological compounds that specifically inhibit (either partially or irreversibly) detyrosinase activity in cellulo. A plethora of compounds that selectively act on TCP activity can be designed according to the invention, for applications as research tools and most promisingly in treatment for several disorders such as neurodegenerative diseases and psychiatric disorders.

Method for Purifying Proteins Having a Tubulin Carboxypeptidase Activity

The present invention proposes a method suitable for purifying proteins having a tubulin carboxypeptidase activity from a biological extract.

In the context of the present invention, the terms "protein having a tubulin carboxypeptidase activity" or "protein having a TCP activity" or "TCPase protein" or "TCP" are used for referring to a class of proteins that are able to cleave off the Glu-Tyr bond to release the C-terminal tyrosine residue from a native tyrosinated tubulin (FIG. 1).

The term "biological sample" means any sample derived from an animal, including multi- or uni-cellular organisms, which contains microtubules. Preferably, the biological sample derived from a mammal, preferably selected from pig, monkey, human, rat or mouse. Examples of such biological samples include fluids, tissues, cell samples, organs, biopsies, etc. Most preferred samples are brain extract, testis extract, and lung extract.

The biological sample may be treated prior to its use, e.g. in order to render the microtubules available. Techniques of cell lysis, concentration or dilution of microtubules, are known by the skilled person.

According to the invention, the method for purifying proteins having a tubulin carboxypeptidase activity from a biological extract, comprises:
(a) centrifuging the biological extract at a temperature comprised between 0 and 10° C., preferably between 2 and 5° C., more preferably at 2° C.;
(b) recovering the supernatant from step (a) and proceeding to a first microtubule polymerization cycle by adding GTP and incubating the mixture at a temperature between 35 and 40° C., preferably at 37° C., +/−2° C., then centrifuging;
(c) recovering the pellets of step (b), resuspending in ice-cold buffer, incubating at 4° C., +/−1° C., and proceeding to a second microtubule polymerization cycle by adding GTP and incubating the mixture at 37° C., +/−2° C., then centrifuging;
(d) recovering the pellets of step (c) resuspending in ice-cold buffer, incubating at 4° C.+/−1° C., and proceeding to a third microtubule polymerization cycle by adding GTP and incubating the mixture at 37° C., +/−2° C., then centrifuging;
(e) resuspending the pellets of step (d) and submitting the mixture to an ion exchange chromatography and recovering the flow through;
(f) precipitating the proteins of the flow through with a 60% saturated ammonium sulphate solution;

(g) submitting the precipitated fraction of step (f) to an hydrophobic chromatography and eluting by gradually decreasing ammonium sulphate concentration up to zero to recover the fraction of proteins with a tubulin carboxypeptidase activity.

In a particular embodiment, the first polymerization cycle comprises (i) adding GTP and incubating the mixture at 37° C., +/−2° C., for 30 minutes, +/−10 minutes; (ii) centrifuging at 22,000 g, +/−1,000 g, at 37° C., +/−2° C., for 45 minutes, +/−10 minutes.

Alternatively or in addition the second polymerization cycle may comprise (i) incubating the mixture on ice for 30 minutes, +/−10 minutes; (ii) centrifuging at 150,000 g+/−10,000 g, 30 minutes, +/−10 minutes; (iii) recovering the supernatant and adding GTP; (iv) incubating the mixture at 37° C., +/−2° C., for at 30 minutes, +/−10 minutes; (v) centrifuging at 50,000 g, +/−1,000 g at a temperature comprised between 30° C. and 37° C., for 30 minutes, +/−10 minutes.

Alternatively or in addition the third polymerization cycle may comprise (i) incubating the mixture on ice for 30 minutes, +/−10 minutes; (ii) centrifuging at 150,000 g, +/−10,000 g, 30 minutes, +/−10 minutes; (iii) recovering the supernatant and adding GTP; (iv) incubating the mixture at 37° C., +/−2° C., for at 30 minutes, +/−10 minutes; (v) centrifuging at 50,000 g, +/−1,000 g at a temperature comprised between 30° C. and 37° C., for 30 minutes, +/−10 minutes.

In a particular embodiment, the method further comprises a step of mass spectrometry characterization of the fraction of proteins of step (g).

In a particular embodiment, the method further comprises a step of selecting proteins that contain a protease domain. To determine what type of protease activity would be required for detyrosination, various inhibitors of cysteine, aspartic, serine, threonine proteases and metalloproteases may be tested.

In a particular embodiment, the fraction of proteins with a tubulin carboxypeptidase activity comprises at least one protein having at least 30%, 40%, 50%, 60%, 70%, 80%, 90%, 95%, 99% amino acid sequence identity with the amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11.

In a particular embodiment, the fraction of proteins with a tubulin carboxypeptidase activity is obtained from a brain extract, such as a brain extract from pigs, and the mass spectrometric data are aligned with human reference sequences, in order to identify corresponding human proteins.

Advantageously, such fraction of proteins comprises at least one protein selected from human Ubiquitin carboxyl-terminal hydrolase 14 (UBP14—SEQ ID NO: 1), human Ubiquitin carboxyl-terminal hydrolase 5 (UBP5—SEQ ID NO: 2), human Methionine aminopeptidase 2 (MAP2—SEQ ID NO: 3), human Xaa-Pro aminopeptidase 1 (XPP1—SEQ ID NO: 4), human Tripeptidyl-peptidase 2 (TPP2—SEQ ID NO: 5), human Vasohibin-1 (VASH1—SEQ ID NO: 6), human dihydropyrimidinase-related protein 1 (DPYL1—SEQ ID NO: 7), human dihydropyrimidinase-related protein 2 (DPYL2—SEQ ID NO: 8), human dihydropyrimidinase-related protein 3 (DPYL3—SEQ ID NO: 9), human dihydropyrimidinase-related protein 4 (DPYL4—SEQ ID NO: 10) and human dihydropyrimidinase-related protein 5 (DPYL5—SEQ ID NO: 11).

In another embodiment, the fraction of proteins comprises at least one protein selected from the proteins listed in Table 1.

Advantageously, the fraction of proteins with a tubulin carboxypeptidase activity is further contacted with microtubules and the level of isolated tyrosine (Y) is measured, thereby confirming the tubulin carboxypeptidase activity of the fraction of proteins. For instance, the microtubules comprise synthetic microtubules and/or α-tubulins, with labeled C-terminal Y.

After a time of contact of the fraction of proteins with putative TCP activity with microtubules, under conditions suitable for the proteins with putative TCP activity to perform detyrosination of the microtubules and/or α-tubulin, the amount of isolated Y, or free Y, in the sample is measured. For instance, tubulin tyrosine ligase (TTL) enzyme incorporates radioactively labeled $^3$H-tyrosine at the very C-terminus of detyrosinated soluble tubulin obtained from e.g. brain extracts. The radioactively labeled tubulin is incorporated in MT during a polymerization cycle to obtain radioactively labeled MTs. TCP activity contained by the biological sample will cut off the radioactively marked tyrosine which can be quantified by scintillation analysis. Alternatively, TCP activity can be monitored by comparing the ratio of detyrosinated versus tyrosinated tubulin before and after exposure to the biological sample by immunoblot analysis.

Several factors may affect the rate at which enzymatic reactions proceed: temperature, pH, enzyme concentration, substrate concentration, and the presence of any inhibitors or activators.

In some embodiments, it is possible to employ a buffer containing a nucleoside triphosphate, such as ATP, potassium chloride, magnesium chloride, and a reducing agent such as DTT in order to provide optimal conditions for the enzymes with putative TCP activity to detyrosinate the microtubules and/or α-tubulin.

The pH value is preferably in the range of 5 to 9, in order to provide suitable conditions for the enzymes with putative TCP activity to detyrosinate the microtubules and/or α-tubulin. More preferably, the pH value is between 5.5 and 8.5, even more preferably between 6 and 8.

A suitable reaction time for enzymes with putative TCP activity to detyrosinate the microtubules and/or α-tubulin may be in the range of 5 minutes to 10 hours, preferably 10 minutes to 5 hours, more preferably 1 hour to 3 hours.

In a particular embodiment, the concentration of fraction of proteins with a tubulin carboxypeptidase activity contacted with microtubules and/or α-tubulin is in the range of 0.1 μm to 1 mM, preferably 0.25 μM to 500 μM, more preferably 0.5 μM to 300 μM, and even more preferably 1 μM to 200 μM, in order to provide optimal conditions for detyrosination of the microtubules and/or α-tubulin.

In a particular embodiment, the fraction of proteins with a tubulin carboxypeptidase activity is contacted with at least α-tubulin. In another particular embodiment, the fraction of proteins with a tubulin carboxypeptidase activity is contacted with a polypeptide corresponding to the C-terminus of α-tubulin. In another embodiment, the fraction of proteins with a tubulin carboxypeptidase activity is contacted with a mixture of microtubules and α-tubulin.

Advantageously, the microtubules and/or α-tubulin comprise synthetic microtubules/peptides and/or α-tubulins, wherein the α-tubulin comprises labeled C-terminal Y, so that step of measuring free Y may be easily implemented.

According to the invention, the tubulin carboxypeptidase activity of the fraction of proteins is confirmed if detectable isolated Y in the sample/microtubules and/or α-tubulin in the sample is observed and compared to a fraction of protein that lacks TCP activity (negative control).

By "synthetic microtubules/peptides and/or α-tubulin" it is intended a microtubule or α-tubulin that has been chemically constructed. The synthetic microtubules or α-tubulin may be artificially constructed by methods of synthetic biology, including solid phase peptide synthesis (SPPS), prior thiol capture strategy, native chemical ligation (NCL). The term "Synthetic microtubules and/or α-tubulin" also encompasses natural microtubule or α-tubulin that has been treated to change its C-terminal amino acid by a labeled -Y.

According to the invention, the labeled -Y consists of a tyrosine that is labeled with a molecule or material that can produce a detectable (such as visually, electronically, radioactively, or otherwise) signal that indicates the presence and/or concentration of the tyrosine in a sample. Thereby, e.g., the presence, location and/or concentration of the tyrosine in a sample can be detected by detecting the signal produced by the detectable molecule or material. The labeled -Y can be detected directly or indirectly. In certain embodiments, the label, or detectable molecule or material, may react with a suitable substrate (e.g., a luciferin) to generate a detectable signal. In particular, the detectable label can be a fluorophore, an enzyme (peroxidase, luciferase), a radioisotope, a fluorescent protein, or a fluorescent dye. Other detectable molecule or material including chemiluminescent labels, electrochemiluminescent labels, bioluminescent labels, polymers, polymer particles, metal particles, haptens, and dyes.

In a particular embodiment, the level of isolated Y in the sample is compared to the level of isolated Y in a control sample comprising solely microtubules and/or α-tubulin. The control sample is free of the fraction of proteins with a tubulin carboxypeptidase activity, so that the difference between both amounts of isolated Y can be attributed to said compound.

Peptidic Based Inhibitors Able to Inhibit Tubulin Carboxypeptidase Activity

According to the invention, the peptidic based inhibitors block or reduce the tubulin carboxypeptidase activity of an enzyme. A peptidic inhibitor can act with competitive, uncompetitive or noncompetitive inhibition. A peptidic inhibitor of the invention can bind reversibly or irreversibly, and therefore the term includes compounds that are suicide substrates of an enzyme with TCP activity.

The present invention relates to a method for selecting a peptidic based inhibitor able to inhibit a tubulin carboxypeptidase activity that has been selected and designed based on the natural C-terminal sequence of α-tubulin.

More particularly, the inventors have developed a method, wherein a peptidic inhibitor containing a peptidic moiety constituted of 1 to 20 amino acids, wherein the most C-terminal amino acid is selected from Y or F, is contacted with a biological extract from an animal, in order to identify and isolate a peptide having a tubulin carboxypeptidase activity.

Therefore, it is an object of the invention to provide a method for selecting a peptidic based inhibitor able to inhibit a tubulin carboxypeptidase activity among peptidic based inhibitor candidates that comprise a peptidic moiety constituted of 1 to 20 amino acids, said peptidic moiety having at the C-terminal position an amino acid selected from Y or F, wherein the method comprises a step (a) of contacting the peptidic based inhibitor candidate with a mixture containing both a fraction of protein with a tubulin carboxypeptidase activity and microtubules; and a step (b) of measuring the level of isolated Y and/or detyrosinated microtubules.

As used herein, the terms "tubulin carboxypeptidase inhibitor" or "peptidic based inhibitor" refers to a class of molecules that target and inhibit, at least partially, the activity of proteins having a tubulin carboxypeptidase activity, and thereby inhibit microtubule detyrosination.

The amino acid sequences defined herein use the one letter code as following: A: Ala (alanine); R: Arg (arginine); N: Asn (asparagine); D: Asp (aspartic acid); C: Cys (cysteine); Q: Gln (glutamine); E: Glu (glutamic acid); G: Gly (glycine); H: His (histidine); I: Ile (isoleucine); L: Leu (leucine); K: Lys (lysine); M: Met (methionine); F: Phe (phenylalanine); P: Pro (proline); S: Ser (serine); T: Thr (threonine); W: Trp (tryptophan); Y: Tyr (tyrosine); V: Val (valine).

The amino acid sequences may also comprise non-naturally-occurring amino acid such as azetidinecarboxylic acid, 2-aminoadipic acid, 3-aminoadipic acid, beta-alanine, aminopropionic acid, 2-aminobutyric acid, A-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, selenocysteine, nitrotyrosine, dihydroxyphenylalanine, and pipecolic acid.

The term "peptide" refers herein to a polymer of amino acid residues linked together by peptide (amide) bonds. Said term also encompasses fragments of polypeptides. Said fragments have preferably biological activity. Said fragments may have a length of 10, 20, 30, 40, 50, 60, 70, 80, 90, 100, 150, 200, 250, 300, 350, 400, 450 or more amino acids.

The term "peptidic moiety" refers to a moiety containing at least one amino acid and at most 20 amino acids. When the peptidic moiety comprises two or more amino acids, said amino acids are linked together by peptide bonds and chemically modified or not.

According to the method of the invention for selecting a peptidic based inhibitor able to inhibit a tubulin carboxypeptidase activity, the peptidic based inhibitor candidate is contacted with a mixture containing both a fraction of protein with a tubulin carboxypeptidase activity and microtubules (step a), and the rate of inhibition of TCP activity is calculated by measuring the level of isolated Y and/or detyrosinated microtubules (step b).

In some embodiments, said method for selecting a peptidic based inhibitor able to inhibit a tubulin carboxypeptidase activity among peptidic based inhibitor candidates that comprise a peptidic moiety constituted of 1 to 20 amino acids, said peptidic moiety having at the C-terminal position an amino acid selected from Y or F, wherein the method comprises: (a) contacting the peptidic based inhibitor candidate with a mixture containing both a fraction of native or recombinant proteins with a tubulin carboxypeptidase activity and microtubules, which preferably comprise synthetic microtubules and/or α-tubulins, with labeled C-terminal Y; (b) measuring the level of isolated Y and/or detyrosinated microtubules.

In a particular embodiment, the reaction temperature is maintained in the range of 1° C. to 70° C., preferably 5° C. to 65° C., more preferably 10° C. to 60° C., even more preferably 15° C. to 55° C., most preferably 19° C. to 43° C., and for example 19° C. to 37° C. in order to provide optimal conditions for the putative TCPase enzyme to detyrosinate the microtubules and/or α-tubulin.

The method of the invention may be implemented with a large kind of peptidic based inhibitors that share sequence identity or homology with the C-terminal amino acid sequence of α-tubulin.

More particularly, the peptidic based inhibitor of the invention comprises a peptidic moiety constituted of 1 to 20 amino acids, said peptidic moiety having at the C-terminal position an amino acid selected from Y or F.

According to the invention, in the three-dimensional conformation of the peptidic moiety the C-terminal Y or F is accessible to enzymes, and more particularly to proteins having a TCP activity.

In a preferred embodiment, the peptidic moiety is constituted of the 1 to 20 amino acid of the most C-terminal amino acid part of alpha-tubulin.

In a particular embodiment, the peptidic moiety is constituted of between 1 and 16 of the most C-terminal amino acids of the amino acid sequence Nter-X1-X2-X3-X4-X5-X6-X7-X8-X9-X10-X11-X12-X13-X14-X15-X16-Cter (SEQ ID NO: 20), wherein X1, X2, X5, X7, X9 and X13 are hydrophobic amino acids, preferably selected from G, A or V, X3, X6, X8, X10, X11, X12, X14 and X15 are negatively charged amino acids, preferably selected from E or D, X4 is an amino acid with a polar uncharged side chain, preferably selected from S, T, N or Q, and X16 is a large hydrophobic amino acid, preferably selected from Y or F.

In general, "X" can denote any amino acid unless indicated otherwise herein.

The physicochemical groups are generally defined as following: the non-polar or hydrophobic amino acids including A, V, I, L, P, F, M, and W, but more narrowly the non-aromatic hydrophobic amino acids as including A, V, I, L, P, and M; the uncharged polar group including G, S, T, C, Y, N and Q; the negatively charged polar group including E and D; and the positively charged polar group including R and K.

X16 refers to the ultimate C-terminal amino acid in the peptidic moiety. Preferably, X16 is Y. The other amino acids are optional. The peptidic moiety may comprise all or part of the amino acids of SEQ ID NO: 12, with respect of the numeration, wherein X1, if present is the N-terminal amino acid in the peptidic moiety, and so on.

In a particular embodiment, the amino acid sequence of the peptidic moiety consists on Y (X16).

In another particular embodiment, the amino acid sequence of the peptidic moiety consists on EDY.

In another particular embodiment, the amino acid sequence of the peptidic moiety consists on EEY.

In another particular embodiment, the amino acid sequence of the peptidic moiety consists on EAY.

In another embodiment, the amino acid sequence of the peptidic moiety comprises or consists on the amino acid sequence selected from SEQ ID NO: 13, SEQ ID NO: 14, SEQ ID NO: 15, SEQ ID NO: 16, SEQ ID NO: 17, SEQ ID NO: 18.

The peptidic inhibitor may inhibit irreversibly or reversibly a tubulin carboxypeptidase activity. As an example, a chemically modified amino acid that may irreversibly react with the cysteine contained by the protein with TCP activity, such as a catalytic triad, is considered to be irreversible. On the other hand a peptide, or chemically modified peptide, that does not covalently react or form reversible bonds with the thiol group contained by the enzyme may be washed off and is considered as reversible. Iodoacetamide is an irreversible inhibitor of all cysteine peptidases, with the mechanism of inhibition occurring from alkylation of the catalytic cysteine residue.

According to the invention, the activity of the peptidic inhibitor may be modulated by expanding the number of amino acid residues and/or by use of a reactive moiety, preferably selected from epoxysuccinyl (Eps), acyloxymethyl, aldehydes and ketones. Such reactive moiety that further functionalizes the peptide may be linked to the peptidic inhibitor by use of known methods in the art, such as, example given, methods of synthetic medicinal chemistry, synthesis of various intermediates, deuterated forms of the compounds and stereoisomers thereof (FIG. 18).

For instance, the peptidic inhibitors is Eps-EEY. Such peptidic inhibitor act as a reversible inhibitor of TCPase activity.

The present invention thus provides a method to design plethora of peptidic inhibitors able to inhibit a tubulin carboxypeptidase activity.

Therapeutic Use of Peptidic Based Inhibitors

As well exposed above, detyrosination of microtubules is associated with cancer progression, aberrant neuronal networks, weak neuronal remodeling, plasticity and/or adaptation. Accordingly, the use of such peptidic inhibitors may have a positive impact in the treatment of disorders involving microtubule detyrosination. For instance, peptidic inhibitors of the present invention may be used for increasing the microtubule dynamics and thereby impacting neuroregeneration.

The present invention thus relates to peptidic based inhibitor for use in the treatment of heart disorder, vascular disorder, cancers, neurodegenerative disorders, muscle disorders, infertility, ciliopathies, more generally a disorder involving altered microtubule detyrosination in an animal, preferably but not limited to a mammal, wherein the peptidic based inhibitor comprises a peptidic moiety constituted of 1 to 20 amino acids, said peptidic moiety having an amino acid selected from Y or F at the C-terminal position, and wherein the peptidic based inhibitor inhibits at least partially a tubulin carboxypeptidase activity. In a particular embodiment, the peptidic based inhibitor comprises GVDSVEAEAEEGEEY (SEQ ID NO: 19). In another embodiment, the peptidic based inhibitor comprises GEEY.

Thus, peptidic inhibitors of the present invention are good candidate for treating neurodegenerative diseases, preferably selected from Alzheimer disease, Parkinson disease, psychiatric disorders, and neural disorders, neuronal regeneration disorders, cancers, preferably selected from colon cancer and neuroblastoma, muscle disorders such as muscular dystrophies, retinal degeneration, heart diseases, vascular disorders, infertility, and ciliopathies.

It is an object of the present invention to provide peptidic based inhibitor for use for treating neurodegenerative diseases. In a particular embodiment, the neurodegenerative disease is Alzheimer disease.

It is a further embodiment to provide peptidic based inhibitor for use for treating cancers.

It is a further embodiment to provide peptidic based inhibitor for use for treating muscular dystrophies, particularly Duchenne muscular dystrophy.

The invention additionally provides a pharmaceutical composition comprising a therapeutically effective amount of a peptidic inhibitors according of the invention.

By "therapeutically effective amount" is meant an amount of the peptidic inhibitor of the invention that elicits a desired therapeutic effect. The exact amount dose will depend on the purpose of the treatment and will be ascertainable by one skilled in the art using known techniques. As is known in the art, adjustments for age, body weight, general health, sex, diet, drug interaction and the severity of the condition may be necessary, and will be ascertainable with routine experimentation by those skilled in the art.

A pharmaceutical composition according to the present invention may further comprise one or more pharmaceutically acceptable carriers. In a specific embodiment, the term "pharmaceutically acceptable" means approved by a regulatory agency or other generally recognized pharmacopoeia for use in animals, and more particularly in humans.

Pharmaceutically acceptable carriers are well known in the art and include, for example, aqueous solutions such as water, 5% dextrose, or physiologically buffered saline or other solvents or vehicles such as glycols, glycerol, oils such as olive oil, or injectable organic esters that are suitable for administration to a human or non-human subject. In some embodiments, a pharmaceutically acceptable carrier or composition is sterile. A pharmaceutical composition can comprise, in addition to the active agent, physiologically acceptable compounds that act, for example, as bulking agents, fillers, solubilizers, stabilizers, osmotic agents, uptake enhancers, etc. Physiologically acceptable compounds include, for example, carbohydrates, such as glucose, sucrose, lactose, dextrans, polyols such as mannitol, antioxidants, such as ascorbic acid or glutathione, preservatives, chelating agents, buffers, or other stabilizers or excipients.

The choice of a pharmaceutically acceptable carrier(s) and/or physiologically acceptable compound(s) can depend for example, on the nature of the active agent, e.g., solubility, compatibility (meaning that the substances can be present together in the composition without interacting in a manner that would substantially reduce the pharmaceutical efficacy of the pharmaceutical composition under ordinary use situations) and/or route of administration of the composition.

Pharmaceutical compositions of the invention comprise a therapeutically effective amount of one or several peptidic inhibitors according to the invention and can be formulated in various forms, e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for topical or oral administration. A variety of routes are applicable for administration of the polypeptide of the invention, including, but not limited to, orally, topically, transdermal, subcutaneously, intravenously, intraperitoneally, intramuscularly or intraocularly. However, any other route may readily be chosen by the person skilled in the art if desired.

The pharmaceutical compositions can be used for the treatment of a wide variety of different diseases and disorders. Thus the invention also encompasses methods of treatment comprising administering a therapeutically effective amount of a peptidic inhibitors of the invention to a subject in need thereof. The subject is typically a mammal, e.g., a human. In some embodiments the subject is a non-human animal that serves as a model for a disease or disorder that affects humans. The animal model may be used, e.g., in preclinical studies, e.g., to assess efficacy and/or determine a suitable dose.

In some embodiments, a peptidic inhibitor of the invention is administered prophylactically, e.g., to a subject who does not exhibit signs or symptoms of the disease or disorder (but may be at increased risk of developing the disorder or is expected to develop the disease or disorder).

EXAMPLES

Example 1: Isolation of Native TCP Activity from Brain Extract

The method for purifying proteins having a tubulin carboxypeptidase activity of the invention has been performed on porcine brain extract. More particularly, microtubule associated proteins (MAPS) were isolated from the crude brain extract (FIG. 2) as exposed below.

Material & Method

PEM-Buffer Composition:

| concentration | chemical | stock |
|---|---|---|
| 50 mM | PIPES/NaOH, pH 6.8 | 400 mM, 4° C. |
| 1 mM | EGTA | 100 mM, RT |
| 1 mM | $MgCl_2$ | 1 M, RT |

Experimental Procedure

Pig brains were quickly removed from the skull and cooled down in ice-cold water by shaking and they were kept on ice. For each 10 g of brain material, 15 ml of PEM buffer containing 1 µl β-mercaptoethanol were added. The brains were pre-homogenised in a mixer and then transferred into a Potter homogeniser (on ice). The extract was spun for 1 h at 22,000 g at 2° C. and the supernatant was removed carefully.

1st Polymerization Cycle:

The supernatant was supplemented with 1 mM GTP and incubated at 37° C. for 30 minutes while the solution was stirred smoothly. Following the incubation, sample was spun down at 22,000 g for 45 min. The pellet containing microtubules and Microtubule Associated Proteins (MAPs) was kept while the supernatant was discarded.

$2^{nd}$ and 3rd Polymerization Cycle:

The pellet was re-suspended in 0.1 vol. of the initial volume in ice-cold PEM buffer containing 0.1 mM GTP and re-homogenised in an ice-cold Potter homogeniser. Next, the suspension was incubated on ice for 30 min and centrifuged for 30 min at 150,000 g at 2° C. (41,000 rpm in a 50-2Ti rotor). The pellet was discarded.

The supernatant was adjusted to 1 mM GTP and incubated in pre-weighted centrifuge tubes for 30 min at 37° C. and after spun for 30 min at 30-37° C., 50,000 g (24,000 rpm in a 50-2Ti rotor). The supernatant was discarded while the pellet, which contains microtubules and MAPs was re-suspended in PEM buffer supplemented with 1 mM GTP and subjected to $3^{rd}$ polymerization cycle.

Following the third cycle the pellet containing microtubules and MAPs was re-suspended and subjected to DEAE-Sephadex ion exchange chromatography. This step serves to separate the tubulin (microtubules), which was found associated with the column while MAPs containing the TCP activity were found in the flow through.

The flow through from the DEAE column was collected and the MAPs were concentrated. Differential ammonium sulphate precipitation was used. The majority of the TCP activity was recovered at 60% of saturated ammonium sulphate solution. This is a critical step experimentally obtained to yield a MAP fraction containing native TCP activity.

To further enrich for TCP activity an additional inventive step consisting of chromatography based on hydrophobic interactions was added. The MAP fraction recovered from ammonium sulphate precipitation was loaded on phenyl sepharose chromatography and eluted by gradually decreasing ammonium sulphate concentration in order to optimize the recovery of native TCP activity from brain extracts. The presence of ammonium sulphate strongly increases surface tension in aqueous solutions and promotes hydrophobic interactions.

Following the elution, the fraction with the highest TCP activity (FIG. 3) was subjected to characterization by mass spectrometry. Importantly the fraction was analyzed in a detyrosination assay to confirm the presence of TCPase activity (FIG. 4). Mass spectrometry analysis of the enriched fraction (FIG. 3) yielded a total of 584 identified proteins, as listed in Table 1 below, which were analyzed by functional homology search to specifically identify TCP candidates based on the presence of protease domain. TCP candidates are peptidases, enzymes that hydrolysis peptide bonds. In the context of the invention, proteases, proteinases and proteolytic enzymes are used interchangeably. To search for potential candidates that contain a protease domain, the obtained list of peptides was analysed for Conserved Domain. This was performed using Conserved Domain Database (CDD) a curated database that annotates functional units in proteins (hosted by NCBI). The collection of domain models includes a set curated by NCBI, which utilizes 3D structure to provide insights into sequence/structure/function relationships. In as such to shorten the list of proteins obtained after specific enrichment down to potential candidates having at least one potential protease domain, enquiries were performed. Besides, further description of the candidates was obtained using MEROPS database a second independent resource for information on peptidases (merops-s.sanger.ac.uk/about/index.shtml). Additionally, proteins with newly identified protease domain were also screened in literature. This resulted in a selection of 11 potential TCP candidates (SEQ ID NO: 1 to SEQ ID NO: 11), among which the family of proteins consisted of collapsin response mediator protein (CRMPs) has been characterized as example.

TABLE 1

List of microtubules associated proteins obtained after purification steps (>2 peptides per hit)

| UNIPROT ID | PROTEINS | GENES | Mol weight [kDa] | Sequence coverage [%] |
|---|---|---|---|---|
| A2AGT5 | Cytoskeleton-associated protein 5 | Ckap5 | 226 | 16.3 |
| A2AJI0 | MAP7 domain-containing protein 1 | Map7d1 | 93 | 3.4 |
| D3Z2H9 | Uncharacterized protein | Tpm3-rs7 | 29 | 23.8 |
| E9PY16 | ArfGAP with dual PH domains 1 | Adap1 | 43 | 15.8 |
| E9Q557 | Desmoplakin | Dsp | 333 | 0.7 |
| E9Q912 | RAP1, GTP-GDP dissociation stimulator 1 | Rap1gds1 | 66 | 15.3 |
| E9QAS7 | Inositol polyphosphate-5-phosphatase A | Inpp5a | 49 | 14.5 |
| F8VPN4 | Amylo-1,6-glucosidase, 4-alpha-glucanotransferase | Agl | 174 | 1.4 |
| O08532 | Voltage-dependent calcium channel subunit alpha-2/delta-1 | Cacna2d1 | 125 | 3.4 |
| O08539 | Myc box-dependent-interacting protein 1 | Bin1 | 64 | 5.4 |
| O08553 | Dihydropyrimidinase-related protein 2 | Dpysl2 | 62 | 49.7 |
| O08599 | Syntaxin-binding protein 1 | Stxbp1 | 68 | 35.4 |
| O08663 | Methionine aminopeptidase 2 | Metap2 | 53 | 13.2 |
| O08749 | Dihydrolipoyl dehydrogenase, mitochondrial | Dld | 54 | 11 |
| O08788 | Dynactin subunit 1 | Dctn1 | 142 | 17.7 |
| O08848 | 60 kDa SS-A/Ro ribonucleoprotein | Trove2 | 60 | 5.4 |
| O09061 | Proteasome subunit beta type-1 | Psmb1 | 26 | 33.3 |
| O35098 | Dihydropyrimidinase-related protein 4 | Dpysl4 | 62 | 15.7 |
| O35136 | Neural cell adhesion molecule 2 | Ncam2 | 93 | 4.8 |
| O35226 | 26S proteasome non-ATPase regulatory subunit 4 | Psmd4 | 41 | 14.4 |
| O35286 | Pre-mRNA-splicing factor ATP-dependent RNA helicase DHX15 | Dhx15 | 91 | 2.9 |
| O35464 | Semaphorin-6A | Sema6a | 114 | 4.8 |
| O35593 | 26S proteasome non-ATPase regulatory subunit 14 | Psmd14 | 35 | 9.4 |
| O35685 | Nuclear migration protein nudC | Nudc | 38 | 19.6 |
| O35841 | Apoptosis inhibitor 5 | Api5 | 57 | 16.3 |
| O35864 | COP9 signalosome complex subunit 5 | Cops5 | 38 | 17.7 |
| O54829 | Regulator of G-protein signaling 7 | Rgs7 | 55 | 5.1 |
| O55013 | Trafficking protein particle complex subunit 3 | Trappc3 | 20 | 10 |
| O55100 | Synaptogyrin-1 | Syngr1 | 26 | 10.3 |
| O55131 | Septin-7 | Sept7 | 51 | 17.2 |
| O55234 | Proteasome subunit beta type-5 | Psmb5 | 29 | 20.8 |
| O70194 | Eukaryotic translation initiation factor 3 subunit D | Eif3d | 64 | 4 |
| O70310 | Glycylpeptide N-tetradecanoyltransferase 1 | Nmt1 | 57 | 22.8 |
| O70311 | Glycylpeptide N-tetradecanoyltransferase 2 | Nmt2 | 60 | 8.3 |
| O70435 | Proteasome subunit alpha type-3 | Psma3 | 28 | 30.6 |
| O70493 | Sorting nexin-12 | Snx12 | 19 | 12.7 |
| O88342 | WD repeat-containing protein 1 | Wdr1 | 66 | 30.5 |
| O88447 | Kinesin light chain 1 | Klc1 | 61 | 6.7 |
| O88485 | Cytoplasmic dynein 1 intermediate chain 1 | Dync1i1 | 71 | 12.7 |
| O88487 | Cytoplasmic dynein 1 intermediate chain 2 | Dync1i2 | 68 | 7.2 |
| O88543 | COP9 signalosome complex subunit 3 | Cops3 | 48 | 9 |
| O88544 | COP9 signalosome complex subunit 4 | Cops4 | 46 | 14 |
| O88569 | Heterogeneous nuclear ribonucleoproteins A2/B1 | Hnrnpa2b1 | 37 | 21.8 |

TABLE 1-continued

List of microtubules associated proteins obtained after purification steps (>2 peptides per hit)

| UNIPROT ID | PROTEINS | GENES | Mol weight [kDa] | Sequence coverage [%] |
|---|---|---|---|---|
| O88643 | Serine/threonine-protein kinase PAK 1 | Pak1 | 61 | 20.9 |
| O88685 | 26S protease regulatory subunit 6A | Psmc3 | 50 | 27.6 |
| O88735 | Ensconsin | Map7 | 82 | 5.2 |
| O88844 | Isocitrate dehydrogenase [NADP] cytoplasmic | Idh1 | 47 | 23.9 |
| O88935 | Synapsin-1 | Syn1 | 74 | 10.3 |
| P00920 | Carbonic anhydrase 2 | Ca2 | 29 | 5.4 |
| P01027 | Complement C3 | C3 | 186 | 2.9 |
| P01869 | Ig gamma-1 chain C region, membrane-bound form | Ighg1 | 43 | 5.6 |
| P02088 | Hemoglobin subunit beta-1 | Hbb-b1 | 16 | 12.2 |
| P03995 | Glial fibrillary acidic protein | Gfap | 50 | 15.8 |
| P04370 | Myelin basic protein | Mbp | 27 | 8 |
| P05063 | Fructose-bisphosphate aldolase C | Aldoc | 39 | 41 |
| P05064 | Fructose-bisphosphate aldolase A | Aldoa | 39 | 35.4 |
| P05132 | cAMP-dependent protein kinase catalytic subunit alpha | Prkaca | 41 | 29.1 |
| P05202 | Aspartate aminotransferase, mitochondrial | Got2 | 47 | 15.1 |
| P06151 | F-lactate dehydrogenase A chain | Ldha | 36 | 8.7 |
| P06745 | Glucose-6-phosphate isomerase | Gpi | 63 | 26 |
| P07356 | Annexin A2 | Anxa2 | 39 | 34.5 |
| P07901 | Heat shock protein HSP 90-alpha | Hsp90aa1 | 85 | 15.3 |
| P08113 | Endoplasmin | Hsp90b1 | 92 | 23.2 |
| P08249 | Malate dehydrogenase, mitochondrial | Mdh2 | 36 | 26.9 |
| P08551 | Neurofilament light polypeptide | Nefl | 62 | 35.5 |
| P08553 | Neurofilament medium polypeptide | Nefm | 96 | 20.5 |
| P09041 | Phosphoglycerate kinase 2 | Pgk2 | 45 | 25.9 |
| P09405 | Nucleolin | Ncl | 77 | 3.3 |
| P09411 | Phosphoglycerate kinase 1 | Pgk1 | 45 | 47.2 |
| P0CG49 | Polyubiquitin-B | Ubb | 9 | 44.2 |
| P10107 | Annexin A1 | Anxa1 | 39 | 7.8 |
| P10126 | Elongation factor 1-alpha 1 | Eef1a1 | 50 | 37.7 |
| P10630 | Eukaryotic initiation factor 4A-II | Eif4a2 | 46 | 33.4 |
| P10637 | Microtubule-associated protein tau | Mapt | 76 | 17.6 |
| P10711 | Transcription elongation factor A protein 1 | Tcea1 | 34 | 26.9 |
| P11103 | Poly [ADP-ribose] polymerase 1 | Parp1 | 113 | 7.6 |
| P11247 | Myeloperoxidase | Mpo | 81 | 3.3 |
| P11499 | Heat shock protein HSP 90-beta | Hsp90ab1 | 83 | 17.1 |
| P11798 | Calcium/calmodulin-dependent protein kinase type II subunit alpha | Camk2a | 54 | 6.9 |
| P11983 | T-complex protein 1 subunit alpha | Tcp1 | 60 | 10.4 |
| P12367 | cAMP-dependent protein kinase type II-alpha regulatory subunit | Prkar2a | 45 | 12.2 |
| P12382 | ATP-dependent 6-phosphofructokinase, liver type | Pfkl | 85 | 15.5 |
| P12960 | Contactin-1 | Cntn1 | 113 | 11.9 |
| P14152 | Malate dehydrogenase, cytoplasmic | Mdh1 | 37 | 9 |
| P14211 | Calreticulin | Calr | 48 | 11.5 |
| P14685 | 26S proteasome non-ATPase regulatory subunit 3 | Psmd3 | 61 | 16.8 |
| P14824 | Annexin A6 | Anxa6 | 76 | 20.5 |
| P14873 | Microtubule-associated protein 1B | Map1b | 270 | 11.5 |
| P15105 | Glutamine synthetase | Glul | 42 | 8.3 |
| P16330 | 2',3'-cyclic-nucleotide 3'-phosphodiesterase | Cnp | 47 | 8.1 |
| P16546 | Spectrin alpha chain, non-erythrocytic 1 | Sptan1 | 285 | 6 |
| P16627 | Heat shock 70 kDa protein 1-like | Hspa1l | 71 | 23.4 |
| P16858 | Glyceraldehyde-3-phosphate dehydrogenase | Gapdh | 36 | 26.4 |
| P17095 | High mobility group protein HMG-I/HMG-Y | Hmga1 | 12 | 26.2 |
| P17156 | Heat shock-related 70 kDa protein 2 | Hspa2 | 70 | 45 |
| P17182 | Alpha-enolase | Eno1 | 47 | 35.5 |
| P17183 | Gamma-enolase | Eno2 | 47 | 11.8 |
| P17426 | AP-2 complex subunit alpha-1 | Ap2a1 | 108 | 11.4 |
| P17427 | AP-2 complex subunit alpha-2 | Ap2a2 | 104 | 3 |
| P17742 | Peptidyl-prolyl cis-trans isomerase A | Ppia | 18 | 23.2 |
| P17751 | Triosephosphate isomerase | Tpi1 | 32 | 14 |
| P18760 | Cofilin-1 | Cfl1 | 19 | 25.9 |
| P19246 | Neurofilament heavy polypeptide | Nefh | 117 | 5.8 |
| P20029 | 78 kDa glucose-regulated protein | Hspa5 | 72 | 40.3 |
| P20357 | Microtubule-associated protein 2 | Map2 | 199 | 15.9 |
| P21550 | Beta-enolase | Eno3 | 47 | 24.2 |
| P24369 | Peptidyl-prolyl cis-trans isomerase B | Ppib | 24 | 30.1 |
| P26040 | Ezrin | Ezr | 69 | 15.5 |
| P26041 | Moesin | Msn | 68 | 39 |
| P26043 | Radixin | Rdx | 69 | 38.6 |
| P26443 | Glutamate dehydrogenase 1, mitochondrial | Glud1 | 61 | 10 |
| P26516 | 26S proteasome non-ATPase regulatory subunit 7 | Psmd7 | 37 | 13.1 |
| P26638 | Serine--tRNA ligase, cytoplasmic | Sars | 58 | 20.1 |
| P27546 | Microtubule-associated protein 4 | Map4 | 117 | 3.6 |
| P27773 | Protein disulfide-isomerase A3 | Pdia3 | 57 | 19.6 |

TABLE 1-continued

List of microtubules associated proteins obtained after purification steps (>2 peptides per hit)

| UNIPROT ID | PROTEINS | GENES | Mol weight [kDa] | Sequence coverage [%] |
|---|---|---|---|---|
| P28271 | Cytoplasmic aconitate hydratase | Aco1 | 98 | 2.9 |
| P28352 | DNA-(apurinic or apyrimidinic site) lyase | Apex1 | 35 | 18.9 |
| P28481 | Collagen alpha-1(II) chain | Col2a1 | 142 | 1.6 |
| P28650 | Adenylosuccinate synthetase isozyme 1 | Adssl1 | 50 | 24.9 |
| P28652 | Calcium/calmodulin-dependent protein kinase type II subunit beta | Camk2b | 60 | 3.9 |
| P28660 | Nck-associated protein 1 | Nckap1 | 129 | 11.8 |
| P28663 | Beta-soluble NSF attachment protein | Napb | 34 | 17.8 |
| P28738 | Kinesin heavy chain isoform 5C | Kif5c | 109 | 25 |
| P28740 | Kinesin-like protein KIF2A | Kif2a | 80 | 19.7 |
| P30416 | Peptidyl-prolyl cis-trans isomerase FKBP4 | Fkbp4 | 52 | 9 |
| P31230 | Aminoacyl tRNA synthase complex-interacting multifunctional protein 1 | Aimp1 | 34 | 9.7 |
| P31324 | cAMP-dependent protein kinase type II-beta regulatory subunit | Prkar2b | 46 | 29.1 |
| P31938 | Dual specificity mitogen-activated protein kinase kinase 1 | Map2k1 | 43 | 24.2 |
| P32883 | GTPase KRas | Kras | 22 | 21.2 |
| P32921 | Tryptophan--tRNA ligase, cytoplasmic | Wars | 54 | 11.2 |
| P34152 | Focal adhesion kinase 1 | Ptk2 | 124 | 2 |
| P35235 | Tyrosine-protein phosphatase non-receptor type 11 | Ptpn11 | 68 | 25.8 |
| P35700 | Peroxiredoxin-1 | Prdx1 | 22 | 27.1 |
| P36916 | Guanine nucleotide-binding protein-like 1 | Gnl1 | 69 | 8.4 |
| P37804 | Transgelin | Tagln | 23 | 17.4 |
| P38647 | Stress-70 protein, mitochondrial | Hspa9 | 73 | 12.8 |
| P39053 | Dynamin-1 | Dnm1 | 98 | 19.7 |
| P39054 | Dynamin-2 | Dnm2 | 98 | 7 |
| P39749 | Flap endonuclease 1 | Fen1 | 42 | 8.5 |
| P40124 | Adenylyl cyclase-associated protein 1 | Cap1 | 52 | 16.7 |
| P40142 | Transketolase | Tkt | 68 | 17.3 |
| P42669 | Transcriptional activator protein Pur-alpha | Pura | 35 | 15.3 |
| P42932 | T-complex protein 1 subunit theta | Cct8 | 60 | 13.1 |
| P45591 | Cofilin-2 | Cfl2 | 19 | 18.7 |
| P45878 | Peptidyl-prolyl cis-trans isomerase FKBP2 | Fkbp2 | 15 | 17.1 |
| P46096 | Synaptotagmin-1 | Syt1 | 47 | 33 |
| P46460 | Vesicle-fusing ATPase | Nsf | 83 | 14 |
| P46471 | 26S protease regulatory subunit 7 | Psmc2 | 49 | 4.8 |
| P46660 | Alpha-internexin | Ina | 55 | 23.8 |
| P46664 | Adenylosuccinate synthetase isozyme 2 | Adss | 50 | 6.4 |
| P47199 | Quinone oxidoreductase | Cryz | 35 | 5.7 |
| P47708 | Rabphilin-3A | Rph3a | 75 | 4 |
| P47753 | F-actin-capping protein subunit alpha-1 | Capza1 | 33 | 22.4 |
| P47754 | F-actin-capping protein subunit alpha-2 | Capza2 | 33 | 51.7 |
| P47757 | F-actin-capping protein subunit beta | Capzb | 31 | 20.9 |
| P47857 | ATP-dependent 6-phosphofructokinase, muscle type | Pfkm | 85 | 17.7 |
| P47934 | Carnitine O-acetyltransferase | Crat | 71 | 2.7 |
| P48024 | Eukaryotic translation initiation factor 1 | Eif1 | 13 | 55.8 |
| P48036 | Annexin A5 | Anxa5 | 36 | 6.3 |
| P48722 | Heat shock 70 kDa protein 4L | Hspa4l | 94 | 8.5 |
| P48758 | Carbonyl reductase [NADPH] 1 | Cbr1 | 31 | 8.3 |
| P49182 | Heparin cofactor 2 | Serpind1 | 54 | 2.9 |
| P49312 | Heterogeneous nuclear ribonucleoprotein A1 | Hnrnpa1 | 34 | 17.2 |
| P49615 | Cyclin-dependent-like kinase 5 | Cdk5 | 33 | 44.9 |
| P49722 | Proteasome subunit alpha type-2 | Psma2 | 26 | 42.7 |
| P50516 | V-type proton ATPase catalytic subunit A | Atp6v1a | 68 | 29.5 |
| P50518 | V-type proton ATPase subunit E 1 | Atp6v1e1 | 26 | 29.2 |
| P50580 | Proliferation-associated protein 2G4 | Pa2g4 | 44 | 33.5 |
| P51174 | Long-chain specific acyl-CoA dehydrogenase, mitochondrial | Acadl | 48 | 6 |
| P51432 | 1-phosphatidylinositol 4,5-bisphosphate phosphodiesterase beta-3 | Plcb3 | 139 | 1.6 |
| P51859 | Hepatoma-derived growth factor | Hdgf | 26 | 14.8 |
| P52196 | Thiosulfate sulfurtransferase | Tst | 33 | 8.8 |
| P52480 | Pyruvate kinase PKM | Pkm | 58 | 35.6 |
| P54071 | Isocitrate dehydrogenase [NADP], mitochondrial | Idh2 | 51 | 22.6 |
| P54227 | Stathmin | Stmn1 | 17 | 14.8 |
| P54823 | Probable ATP-dependent RNA helicase DDX6 | Ddx6 | 54 | 4.8 |
| P55066 | Neurocan core protein | Ncan | 137 | 1.5 |
| P55821 | Stathmin-2 | Stmn2 | 21 | 10.6 |
| P56212 | cAMP-regulated phosphoprotein 19 | Arpp19 | 12 | 49.1 |
| P56399 | Ubiquitin carboxyl-terminal hydrolase 5 | Usp5 | 96 | 2.4 |
| P57759 | Endoplasmic reticulum resident protein 29 | Erp29 | 29 | 6.9 |
| P58252 | Elongation factor 2 | Eef2 | 95 | 22.7 |
| P59325 | Eukaryotic translation initiation factor 5 | Eif5 | 49 | 23.8 |

TABLE 1-continued

List of microtubules associated proteins obtained after purification steps (>2 peptides per hit)

| UNIPROT ID | PROTEINS | GENES | Mol weight [kDa] | Sequence coverage [%] |
|---|---|---|---|---|
| P60521 | Gamma-aminobutyric acid receptor-associated protein-like 2 | Gabarapl2 | 14 | 36.8 |
| P60710 | Actin, cytoplasmic 1 | Actb | 42 | 48 |
| P60840 | Alpha-endosulfine | Ensa | 13 | 30.6 |
| P60843 | Eukaryotic initiation factor 4A-I | Eif4a1 | 46 | 17.5 |
| P61082 | NEDD8-conjugating enzyme Ubc12 | Ube2m | 21 | 16.4 |
| P61089 | Ubiquitin-conjugating enzyme E2 N | Ube2n | 17 | 43.4 |
| P61148 | Fibroblast growth factor 1 | Fgf1 | 17 | 20 |
| P61161 | Actin-related protein 2 | Actr2 | 45 | 22.8 |
| P61164 | Alpha-centractin | Actr1a | 43 | 28.7 |
| P61202 | COP9 signalosome complex subunit 2 | Cops2 | 52 | 13.5 |
| P61222 | ATP-binding cassette sub-family E member 1 | Abce1 | 67 | 23.7 |
| P61329 | Fibroblast growth factor 12 | Fgf12 | 27 | 22.2 |
| P61961 | Ubiquitin-fold modifier 1 | Ufm1 | 9 | 50.6 |
| P61965 | WD repeat-containing protein 5 | Wdr5 | 37 | 13.5 |
| P61982 | 14-3-3 protein gamma | Ywhag | 28 | 33.2 |
| P62082 | 40S ribosomal protein S7 | Rps7 | 22 | 32.8 |
| P62137 | Serine/threonine-protein phosphatase PP1-alpha catalytic subunit | Ppp1ca | 38 | 13 |
| P62141 | Serine/threonine-protein phosphatase PP1-beta catalytic subunit | Ppp1cb | 37 | 17.7 |
| P62196 | 26S protease regulatory subunit 8 | Psmc5 | 46 | 9.6 |
| P62204 | Calmodulin | Calm1 | 17 | 33.6 |
| P62245 | 40S ribosomal protein S15a | Rps15a | 15 | 23.8 |
| P62334 | 26S protease regulatory subunit 10B | Psmc6 | 44 | 7.5 |
| P62627 | Dynein light chain roadblock-type 1 | Dynlrb1 | 11 | 21.9 |
| P62631 | Elongation factor 1-alpha 2 | Eef1a2 | 50 | 55.3 |
| P62806 | Histone H4 | Hist1h4a | 11 | 17.5 |
| P62814 | V-type proton ATPase subunit B, brain isoform | Atp6v1b2 | 57 | 5.1 |
| P62827 | GTP-binding nuclear protein Ran | Ran | 24 | 19.9 |
| P62852 | 40S ribosomal protein S25 | Rps25 | 14 | 14.4 |
| P62858 | 40S ribosomal protein S28 | Rps28 | 8 | 30.4 |
| P62881 | Guanine nucleotide-binding protein subunit beta-5 | Gnb5 | 44 | 8.4 |
| P63001 | Ras-related C3 botulinum toxin substrate 1 | Rac1 | 21 | 16.7 |
| P63005 | Platelet-activating factor acetylhydrolase IB subunit alpha | Pafah1b1 | 47 | 39.8 |
| P63017 | Heat shock cognate 71 kDa protein | Hspa8 | 71 | 56.7 |
| P63028 | Translationally-controlled tumor protein | Tpt1 | 19 | 18.6 |
| P63046 | Sulfotransferase 4A1 | Sult4a1 | 33 | 14.1 |
| P63085 | Mitogen-activated protein kinase 1 | Mapk1 | 41 | 37.4 |
| P63087 | Serine/threonine-protein phosphatase PP1-gamma catalytic subunit | Ppp1cc | 37 | 12.1 |
| P63101 | 14-3-3 protein zeta/delta | Ywhaz | 28 | 22.4 |
| P63158 | High mobility group protein B1 | Hmgb1 | 25 | 21.9 |
| P63242 | Eukaryotic translation initiation factor 5A-1 | Eif5a | 17 | 34.4 |
| P63280 | SUMO-conjugating enzyme UBC9 | Ube2i | 18 | 16.5 |
| P63328 | Serine/threonine-protein phosphatase 2B catalytic subunit alpha isoform | Ppp3ca | 59 | 3.5 |
| P68033 | Actin, alpha cardiac muscle 1 | Actc1 | 42 | 27.3 |
| P68037 | Ubiquitin-conjugating enzyme E2 L3 | Ube2l3 | 18 | 51.9 |
| P68181 | cAMP-dependent protein kinase catalytic subunit beta | Prkacb | 41 | 22.8 |
| P68254 | 14-3-3 protein theta | Ywhaq | 28 | 11.8 |
| P68368 | Tubulin alpha-4A chain | Tuba4a | 50 | 33.3 |
| P68372 | Tubulin beta-4B chain | Tubb4b | 50 | 48.8 |
| P68373 | Tubulin alpha-1C chain | Tuba1c | 50 | 43 |
| P70122 | Ribosome maturation protein SBDS | Sbds | 29 | 40.4 |
| P70236 | Dual specificity mitogen-activated protein kinase kinase 6 | Map2k6 | 37 | 20.1 |
| P70296 | Phosphatidylethanolamine-binding protein 1 | Pebp1 | 21 | 17.6 |
| P70336 | Rho-associated protein kinase 2 | Rock2 | 161 | 9.1 |
| P70441 | Na(+)/H(+) exchange regulatory cofactor NHE-RF1 | Slc9a3r1 | 39 | 7 |
| P70670 | Nascent polypeptide-associated complex subunit alpha, muscle-specific form | Naca | 221 | 2.6 |
| P70695 | Fructose-1,6-bisphosphatase isozyme 2 | Fbp2 | 37 | 6.8 |
| P80313 | T-complex protein 1 subunit eta | Cct7 | 60 | 16.4 |
| P80314 | T-complex protein 1 subunit beta | Cct2 | 57 | 25 |
| P80315 | T-complex protein 1 subunit delta | Cct4 | 58 | 7.4 |
| P80316 | T-complex protein 1 subunit epsilon | Cct5 | 60 | 9.6 |
| P80317 | T-complex protein 1 subunit zeta | Cct6a | 58 | 18.6 |
| P80318 | T-complex protein 1 subunit gamma | Cct3 | 61 | 25.5 |
| P84078 | ADP-ribosylation factor 1 | Arf1 | 21 | 43.6 |
| P84091 | AP-2 complex subunit mu | Ap2m1 | 50 | 4.8 |
| P97376 | Protein FRG1 | Frg1 | 29 | 15.5 |
| P97390 | Vacuolar protein sorting-associated protein 45 | Vps45 | 65 | 7.2 |

TABLE 1-continued

List of microtubules associated proteins obtained after purification steps (>2 peptides per hit)

| UNIPROT ID | PROTEINS | GENES | Mol weight [kDa] | Sequence coverage [%] |
|---|---|---|---|---|
| P97427 | Dihydropyrimidinase-related protein 1 | Crmp1 | 62 | 21.7 |
| P97807 | Fumarate hydratase, mitochondrial | Fh | 54 | 13 |
| P99024 | Tubulin beta-5 chain | Tubb5 | 50 | 48.9 |
| P99026 | Proteasome subunit beta type-4 | Psmb4 | 29 | 8.7 |
| Q00PI9 | Heterogeneous nuclear ribonucleoprotein U-like protein 2 | Hnrnpul2 | 85 | 2.6 |
| Q01730 | Ras suppressor protein 1 | Rsu1 | 32 | 27.8 |
| Q02053 | Ubiquitin-like modifier-activating enzyme 1 | Uba1 | 118 | 4 |
| Q04447 | Creatine kinase B-type | Ckb | 43 | 13.6 |
| Q05BC3 | Echinoderm microtubule-associated protein-like 1 | Eml1 | 90 | 18.7 |
| Q06138 | Calcium-binding protein 39 | Cab39 | 40 | 24.9 |
| Q08642 | Protein-arginine deiminase type-2 | Padi2 | 76 | 8.3 |
| Q2NL51 | Glycogen synthase kinase-3 alpha | Gsk3a | 52 | 7.1 |
| Q2PFD7 | PH and SEC7 domain-containing protein 3 | Psd3 | 115 | 5.2 |
| Q3TGF2 | Protein FAM107B | Fam107b | 16 | 16 |
| Q3THG9 | Alanyl-tRNA editing protein Aarsd1 | Aarsd1 | 61 | 4.4 |
| Q3THK3 | General transcription factor IIF subunit 1 | Gtf2f1 | 57 | 6.7 |
| Q3THK7 | GMP synthase [glutamine-hydrolyzing] | Gmps | 77 | 6.2 |
| Q3TKT4 | Transcription activator BRG1 | Smarca4 | 181 | 1.4 |
| Q3TXS7 | 26S proteasome non-ATPase regulatory subunit 1 | Psmd1 | 106 | 9.4 |
| Q3UGR5 | Haloacid dehalogenase-like hydrolase domain-containing protein 2 | Hdhd2 | 29 | 11.2 |
| Q3UHF1 | CaM kinase-like vesicle-associated protein | Camkv | 55 | 20.1 |
| Q3UHX2 | 28 kDa heat- and acid-stable phosphoprotein | Pdap1 | 21 | 27.1 |
| Q3ULJ0 | Glycerol-3-phosphate dehydrogenase 1-like protein | Gpd1l | 38 | 4.6 |
| Q3UM45 | Protein phosphatase 1 regulatory subunit 7 | Ppp1r7 | 41 | 10.2 |
| Q3UMU9 | Hepatoma-derived growth factor-related protein 2 | Hdgfrp2 | 74 | 9.3 |
| Q3UMY5 | Echinoderm microtubule-associated protein-like 4 | Eml4 | 110 | 2.8 |
| Q3UV17 | Keratin, type II cytoskeletal 2 oral | Krt76 | 63 | 2.7 |
| Q3UX10 | Tubulin alpha chain-like 3 | Tubal3 | 50 | 6.3 |
| Q3V1L4 | Cytosolic purine 5'-nucleotidase | Nt5c2 | 65 | 4.8 |
| Q4KMM3 | Oxidation resistance protein 1 | Oxr1 | 96 | 4.7 |
| Q5M8N0 | CB1 cannabinoid receptor-interacting protein 1 | Cnrip1 | 19 | 5.5 |
| Q5SQX6 | Cytoplasmic FMR1-interacting protein 2 | Cyfip2 | 146 | 12.8 |
| Q5SSL4 | Active breakpoint cluster region-related protein | Abr | 98 | 2.2 |
| Q60668 | Heterogeneous nuclear ribonucleoprotein D0 | Hnrnpd | 38 | 32.1 |
| Q60676 | Serine/threonine-protein phosphatase 5 | Ppp5c | 57 | 24.2 |
| Q60692 | Proteasome subunit beta type-6 | Psmb6 | 25 | 8 |
| Q60864 | Stress-induced-phosphoprotein 1 | Stip1 | 63 | 23.4 |
| Q60872 | Eukaryotic translation initiation factor 1A | Eif1a | 16 | 18.1 |
| Q60875 | Rho guanine nucleotide exchange factor 2 | Arhgef2 | 112 | 4.3 |
| Q60900 | ELAV-like protein 3 | Elavl3 | 40 | 4.4 |
| Q60972 | Histone-binding protein RBBP4 | Rbbp4 | 48 | 16.2 |
| Q61035 | Histidine--tRNA ligase, cytoplasmic | Hars | 57 | 14.9 |
| Q61036 | Serine/threonine-protein kinase PAK 3 | Pak3 | 62 | 11.1 |
| Q61142 | Spindlin-1 | Spin1 | 30 | 10.3 |
| Q61166 | Microtubule-associated protein RP/EB family member 1 | Mapre1 | 30 | 21.3 |
| Q61316 | Heat shock 70 kDa protein 4 | Hspa4 | 94 | 2.9 |
| Q61425 | Hydroxyacyl-coenzyme A dehydrogenase, mitochondrial | Hadh | 34 | 6.7 |
| Q61548 | Clathrin coat assembly protein AP180 | Snap91 | 92 | 12.7 |
| Q61553 | Fascin | Fscn1 | 55 | 19.3 |
| Q61644 | Protein kinase C and casein kinase substrate in neurons protein 1 | Pacsin1 | 51 | 12.5 |
| Q61646 | Haptoglobin | Hp | 39 | 4.9 |
| Q61696 | Heat shock 70 kDa protein 1A | Hspa1a | 70 | 32.3 |
| Q61753 | D-3-phosphoglycerate dehydrogenase | Phgdh | 57 | 7.3 |
| Q61768 | Kinesin-1 heavy chain | Kif5b | 110 | 15.9 |
| Q61879 | Myosin-10 | Myh10 | 229 | 3.8 |
| Q62165 | Dystroglycan | Dag1 | 97 | 3.1 |
| Q62188 | Dihydropyrimidinase-related protein 3 | Dpysl3 | 62 | 24.7 |
| Q62261 | Spectrin beta chain, non-erythrocytic 1 | Sptbn1 | 274 | 1.2 |
| Q62420 | Endophilin-A1 | Sh3gl2 | 40 | 15.3 |
| Q62446 | Peptidyl-prolyl cis-trans isomerase FKBP3 | Fkbp3 | 25 | 25.9 |
| Q63844 | Mitogen-activated protein kinase 3 | Mapk3 | 43 | 15.5 |
| Q63912 | Oligodendrocyte-myelin glycoprotein | Omg | 49 | 9.5 |
| Q64152 | Transcription factor BTF3 | Btf3 | 22 | 32.4 |
| Q641P0 | Actin-related protein 3B | Actr3b | 48 | 12.9 |
| Q64467 | Glyceraldehyde-3-phosphate dehydrogenase, testis-specific | Gapdhs | 48 | 4.1 |
| Q64514 | Tripeptidyl-peptidase 2 | Tpp2 | 140 | 3.7 |
| Q64669 | NAD(P)H dehydrogenase [quinone] 1 | Nqo1 | 31 | 6.9 |
| Q68FL6 | Methionine--tRNA ligase, cytoplasmic | Mars | 101 | 3.2 |

TABLE 1-continued

List of microtubules associated proteins obtained after purification steps (>2 peptides per hit)

| UNIPROT ID | PROTEINS | GENES | Mol weight [kDa] | Sequence coverage [%] |
|---|---|---|---|---|
| Q69ZS7 | HBS1-like protein | Hbs1l | 75 | 8.4 |
| Q6A028 | Switch-associated protein 70 | Swap70 | 69 | 12.6 |
| Q6DIC0 | Probable global transcription activator SNF2L2 | Smarca2 | 180 | 1.6 |
| Q6NZB0 | DnaJ homolog subfamily C member 8 | Dnajc8 | 30 | 36 |
| Q6P1B1 | Xaa-Pro aminopeptidase 1 | Xpnpep1 | 70 | 14.6 |
| Q6PDI5 | Proteasome-associated protein ECM29 homolog | Ecm29 | 204 | 5.9 |
| Q6PDL0 | Cytoplasmic dynein 1 light intermediate chain 2 | Dync1li2 | 54 | 8.9 |
| Q6PER3 | Microtubule-associated protein RP/EB family member 3 | Mapre3 | 32 | 35.6 |
| Q6PGN3 | Serine/threonine-protein kinase DCLK2 | Dclk2 | 83 | 6.1 |
| Q6WVG3 | BTB/POZ domain-containing protein KCTD12 | Kctd12 | 36 | 7.3 |
| Q6ZPJ3 | (E3-independent) E2 ubiquitin-conjugating enzyme UBE2O | Ube2o | 141 | 1.8 |
| Q6ZQ38 | Cullin-associated NEDD8-dissociated protein 1 | Cand1 | 136 | 12.1 |
| Q6ZWX6 | Eukaryotic translation initiation factor 2 subunit 1 | Eif2s1 | 36 | 44.8 |
| Q71LX4 | Talin-2 | Tln2 | 254 | 1 |
| Q78JW9 | Ubiquitin domain-containing protein UBFD1 | Ubfd1 | 40 | 11.4 |
| Q78PG9 | Coiled-coil domain-containing protein 25 | Ccdc25 | 24 | 17.3 |
| Q78ZA7 | Nucleosome assembly protein 1-like 4 | Nap1l4 | 43 | 7.5 |
| Q792Z1 | MCG140784 | Try10 | 26 | 8.1 |
| Q7M6Y3 | Phosphatidylinositol-binding clathrin assembly protein | Picalm | 72 | 6.7 |
| Q7TMB8 | Cytoplasmic FMR1-interacting protein 1 | Cyfip1 | 145 | 7.7 |
| Q7TMK9 | Heterogeneous nuclear ribonucleoprotein Q | Syncrip | 70 | 8.2 |
| Q7TMM9 | Tubulin beta-2A chain | Tubb2a | 50 | 50.8 |
| Q7TNG5 | Echinoderm microtubule-associated protein-like 2 | Eml2 | 71 | 4.5 |
| Q7TNV0 | Protein DEK | Dek | 43 | 6.6 |
| Q7TQD2 | Tubulin polymerization-promoting protein | Tppp | 24 | 16.1 |
| Q7TSJ2 | Microtubule-associated protein 6 | Map6 | 96 | 3.9 |
| Q80TV8 | CLIP-associating protein 1 | Clasp1 | 169 | 10.2 |
| Q80UG5 | Septin-9 | Sept9 | 66 | 4.3 |
| Q80UM3 | N-alpha-acetyltransferase 15, NatA auxiliary subunit | Naa15 | 101 | 9.9 |
| Q80VP1 | Epsin-1 | Epn1 | 60 | 3.8 |
| Q80XU3 | Nuclear ubiquitous casein and cyclin-dependent kinase substrate 1 | Nucks1 | 26 | 19.7 |
| Q810S1 | Calcium uniporter regulatory subunit MCUb, mitochondrial | Mcub | 40 | 5.5 |
| Q810U3 | Neurofascin | Nfasc | 138 | 6 |
| Q8BFR5 | Elongation factor Tu, mitochondrial | Tufm | 50 | 5.8 |
| Q8BFZ3 | Beta-actin-like protein 2 | Actbl2 | 42 | 22.1 |
| Q8BG05 | Heterogeneous nuclear ribonucleoprotein A3 | Hnrnpa3 | 40 | 24.8 |
| Q8BG32 | 26S proteasome non-ATPase regulatory subunit 11 | Psmd11 | 47 | 32 |
| Q8BGA3 | Leucine-rich repeat transmembrane neuronal protein 2 | Lrrtm2 | 59 | 5.4 |
| Q8BGQ7 | Alanine--tRNA ligase, cytoplasmic | Aars | 107 | 2.4 |
| Q8BGR9 | Ubiquitin-like domain-containing CTD phosphatase 1 | Ublcp1 | 37 | 20.1 |
| Q8BGT8 | Phytanoyl-CoA hydroxylase-interacting protein-like | Phyhipl | 42 | 14.7 |
| Q8BGY2 | Eukaryotic translation initiation factor 5A-2 | Eif5a2 | 17 | 19 |
| Q8BH57 | WD repeat-containing protein 48 | Wdr48 | 76 | 11.2 |
| Q8BJ37 | Tyrosyl-DNA phosphodiesterase 1 | Tdp1 | 69 | 5.1 |
| Q8BJD1 | Inter-alpha-trypsin inhibitor heavy chain H5 | Itih5 | 107 | 3.2 |
| Q8BK63 | Casein kinase I isoform alpha | Csnk1a1 | 39 | 10.4 |
| Q8BK64 | Activator of 90 kDa heat shock protein ATPase homolog 1 | Ahsa1 | 38 | 18.9 |
| Q8BK67 | Protein RCC2 | Rcc2 | 56 | 14.8 |
| Q8BKG3 | Inactive tyrosine-protein kinase 7 | Ptk7 | 118 | 2.8 |
| Q8BKX1 | Brain-specific angiogenesis inhibitor 1-associated protein 2 | Baiap2 | 59 | 6.7 |
| Q8BLJ3 | PI-PLC X domain-containing protein 3 | Plcxd3 | 36 | 10.3 |
| Q8BMF3 | NADP-dependent malic enzyme, mitochondrial | Me3 | 67 | 3.1 |
| Q8BMJ2 | Leucine--tRNA ligase, cytoplasmic | Lars | 134 | 2.6 |
| Q8BP47 | Asparagine--tRNA ligase, cytoplasmic | Nars | 64 | 5.5 |
| Q8BRT1 | CLIP-associating protein 2 | Clasp2 | 141 | 9.3 |
| Q8BU30 | Isoleucine--tRNA ligase, cytoplasmic | Iars | 144 | 2.9 |
| Q8BVI4 | Dihydropteridine reductase | Qdpr | 26 | 15.8 |
| Q8BVQ5 | Protein phosphatase methylesterase 1 | Ppme1 | 42 | 8.8 |
| Q8BVU5 | ADP-ribose pyrophosphatase, mitochondrial | Nudt9 | 39 | 6.6 |
| Q8BW96 | Calcium/calmodulin-dependent protein kinase type 1D | Camk1d | 43 | 16.1 |
| Q8BWG8 | Beta-arrestin-1 | Arrb1 | 47 | 10.8 |
| Q8BWR2 | PITH domain-containing protein 1 | Pithd1 | 24 | 28.4 |
| Q8BWY3 | Eukaryotic peptide chain release factor subunit 1 | Etf1 | 49 | 10.1 |
| Q8BWZ3 | N-alpha-acetyltransferase 25, NatB auxiliary subunit | Naa25 | 112 | 6.8 |
| Q8BYB9 | Protein O-glucosyltransferase 1 | Poglut1 | 46 | 11.7 |
| Q8BZ98 | Dynamin-3 | Dnm3 | 97 | 8.8 |
| Q8C1B1 | Calmodulin-regulated spectrin-associated protein 2 | Camsap2 | 164 | 1.6 |
| Q8C1B7 | Septin-11 | Sept11 | 50 | 18.8 |

TABLE 1-continued

List of microtubules associated proteins obtained after purification steps (>2 peptides per hit)

| UNIPROT ID | PROTEINS | GENES | Mol weight [kDa] | Sequence coverage [%] |
|---|---|---|---|---|
| Q8C1W1 | Vasohibin-1 | Vash1 | 42 | 12.8 |
| Q8C4Q6 | Axin interactor, dorsalization-associated protein | Aida | 35 | 16.4 |
| Q8C5R8 | Phosphoribosyl pyrophosphate synthetase 1-like 1 | Prps1l1 | 35 | 11.6 |
| Q8C8R3 | Ankyrin-2 | Ank2 | 426 | 1.2 |
| Q8CBY8 | Dynactin subunit 4 | Dctn4 | 53 | 7.3 |
| Q8CDN6 | Thioredoxin-like protein 1 | Txnl1 | 32 | 30.1 |
| Q8CGC7 | Bifunctional glutamate/proline--tRNA ligase | Eprs | 170 | 2 |
| Q8CGF7 | Transcription elongation regulator 1 | Tcerg1 | 124 | 3.9 |
| Q8CHC4 | Synaptojanin-1 | Synj1 | 173 | 13 |
| Q8CIB5 | Fermitin family homolog 2 | Fermt2 | 78 | 3.2 |
| Q8CIN4 | Serine/threonine-protein kinase PAK 2 | Pak2 | 58 | 11.5 |
| Q8JZK9 | Hydroxymethylglutaryl-CoA synthase, cytoplasmic | Hmgcs1 | 58 | 6.9 |
| Q8JZQ9 | Eukaryotic translation initiation factor 3 subunit B | Eif3b | 91 | 3.9 |
| Q8K0S0 | Phytanoyl-CoA hydroxylase-interacting protein | Phyhip | 38 | 8.2 |
| Q8K0U4 | Heat shock 70 kDa protein 12A | Hspa12a | 75 | 9.6 |
| Q8K1J6 | CCA tRNA nucleotidyltransferase 1, mitochondrial | Trnt1 | 50 | 9.2 |
| Q8K1M6 | Dynamin-1-like protein | Dnm1l | 83 | 11.7 |
| Q8K2T1 | NmrA-like family domain-containing protein 1 | Nmral1 | 34 | 8.1 |
| Q8K409 | DNA polymerase beta | Polb | 38 | 13.7 |
| Q8QZT1 | Acetyl-CoA acetyltransferase, mitochondrial | Acat1 | 45 | 9.9 |
| Q8QZY1 | Eukaryotic translation initiation factor 3 subunit L | Eif3l | 67 | 8.2 |
| Q8R001 | Microtubule-associated protein RP/EB family member 2 | Mapre2 | 37 | 21.2 |
| Q8R050 | Eukaryotic peptide chain release factor GTP-binding subunit ERF3A | Gspt1 | 69 | 9 |
| Q8R0F6 | Integrin-linked kinase-associated serine/threonine phosphatase 2C | Ilkap | 43 | 18.1 |
| Q8R0Y6 | Cytosolic 10-formyltetrahydrofolate dehydrogenase | Aldh1l1 | 99 | 3.1 |
| Q8R1B4 | Eukaryotic translation initiation factor 3 subunit C | Eif3c | 106 | 7.7 |
| Q8R1Q8 | Cytoplasmic dynein 1 light intermediate chain 1 | Dync1li1 | 57 | 5.4 |
| Q8R3R8 | Gamma-aminobutyric acid receptor-associated protein-like 1 | Gabarapl1 | 14 | 35 |
| Q8R574 | Phosphoribosyl pyrophosphate synthase-associated protein 2 | Prpsap2 | 41 | 28.2 |
| Q8R5C5 | Beta-centractin | Actr1b | 42 | 20.5 |
| Q8R5H6 | Wiskott-Aldrich syndrome protein family member 1 | Wasf1 | 62 | 3.6 |
| Q8VDD5 | Myosin-9 | Myh9 | 226 | 5 |
| Q8VDM4 | 26S proteasome non-ATPase regulatory subunit 2 | Psmd2 | 100 | 13.4 |
| Q8VE37 | Regulator of chromosome condensation | Rcc1 | 45 | 18.3 |
| Q8VED9 | Galectin-related protein | Lgalsl | 19 | 25.6 |
| Q8VEK3 | Heterogeneous nuclear ribonucleoprotein U | Hnrnpu | 88 | 11.4 |
| Q8VHM5 | Heterogeneous nuclear ribonucleoprotein R | Hnrnpr | 71 | 6 |
| Q91UZ1 | Phosphoinositide phospholipase C | Plcb4 | 135 | 6.7 |
| Q91V09 | WD repeat-containing protein 13 | Wdr13 | 54 | 7.8 |
| Q91V12 | Cytosolic acyl coenzyme A thioeste hydrolase | Acot7 | 43 | 18.6 |
| Q91V57 | N-chimaerin | Chn1 | 53 | 6.1 |
| Q91V89 | Protein phosphatase 2, regulatory subunit B (B56), delta isoform | Ppp2r5d | 69 | 4.2 |
| Q91V92 | ATP-citrate synthase | Acly | 120 | 15.4 |
| Q91VK1 | Basic leucine zipper and W2 domain-containing protein 2 | Bzw2 | 48 | 19.8 |
| Q91VR5 | ATP-dependent RNA helicase DDX1 | Ddx1 | 82 | 8.4 |
| Q91VR7 | Microtubule-associated proteins 1A/1B light chain 3A | Map1lc3a | 14 | 23.1 |
| Q91VZ6 | Stromal membrane-associated protein 1 | Smap1 | 48 | 4.5 |
| Q91WC0 | Histone-lysine N-methyltransferase setd3 | Setd3 | 67 | 3 |
| Q91WQ3 | Tyrosine--tRNA ligase, cytoplasmic | Yars | 59 | 37.7 |
| Q91XL9 | Oxysterol-binding protein-related protein 1 | Osbpl1a | 108 | 7.2 |
| Q91XM9 | Disks large homolog 2 | Dlg2 | 95 | 16.2 |
| Q91YE3 | Egl nine homolog 1 | Egln1 | 43 | 5.2 |
| Q91YJ3 | Thymocyte nuclear protein 1 | Thyn1 | 26 | 7.5 |
| Q91YP2 | Neurolysin, mitochondrial | Nln | 80 | 6.4 |
| Q91YR1 | Twinfilin-1 | Twf1 | 40 | 15.4 |
| Q91ZJ5 | UTP--glucose-1-phosphate uridylyltransferase | Ugp2 | 57 | 22 |
| Q91ZW3 | SWI/SNF-related matrix-associated actin-dependent regulator of chromatin subfamily A member 5 | Smarca5 | 122 | 2 |
| Q921M7 | Protein FAM49B | Fam49b | 37 | 38 |
| Q921W0 | Charged multivesicular body protein 1a | Chmp1a | 22 | 12.8 |
| Q921X9 | Protein disulfide-isomerase A5 | Pdia5 | 59 | 6.6 |
| Q922B2 | Aspartate--tRNA ligase, cytoplasmic | Dars | 57 | 5.6 |
| Q922D8 | C-1-tetrahydrofolate synthase, cytoplasmic | Mthfd1 | 101 | 7.1 |
| Q922F4 | Tubulin beta-6 chain | Tubb6 | 50 | 26.8 |
| Q922J3 | CAP-Gly domain-containing linker protein 1 | Clip1 | 156 | 12.9 |
| Q923D2 | Flavin reductase (NADPH) | Blvrb | 22 | 21.4 |
| Q924Y0 | Gamma-butyrobetaine dioxygenase | Bbox1 | 45 | 6.5 |

TABLE 1-continued

List of microtubules associated proteins obtained after purification steps (>2 peptides per hit)

| UNIPROT ID | PROTEINS | GENES | Mol weight [kDa] | Sequence coverage [%] |
|---|---|---|---|---|
| Q99020 | Heterogeneous nuclear ribonucleoprotein A/B | Hnrnpab | 31 | 20 |
| Q99104 | Unconventional myosin-Va | Myo5a | 216 | 1.1 |
| Q99J08 | SEC14-like protein 2 | Sec14l2 | 46 | 5.2 |
| Q99J36 | THUMP domain-containing protein 1 | Thumpd1 | 39 | 19.1 |
| Q99J77 | Sialic acid synthase | Nans | 40 | 8.9 |
| Q99JF8 | PC4 and SFRS1-interacting protein | Psip1 | 60 | 14.8 |
| Q99JI4 | 26S proteasome non-ATPase regulatory subunit 6 | Psmd6 | 46 | 11.8 |
| Q99JY9 | Actin-related protein 3 | Actr3 | 47 | 30.1 |
| Q99K85 | Phosphoserine aminotransferase | Psat1 | 40 | 7.8 |
| Q99KB8 | Hydroxyacylglutathione hydrolase, mitochondrial | Hagh | 34 | 17.2 |
| Q99KI0 | Aconitate hydratase, mitochondrial | Aco2 | 85 | 27.2 |
| Q99KJ8 | Dynactin subunit 2 | Dctn2 | 44 | 17.7 |
| Q99KK2 | N-acylneuraminate cytidylyltransferase | Cmas | 48 | 4.6 |
| Q99L45 | Eukaryotic translation initiation factor 2 subunit 2 | Eif2s2 | 38 | 24.2 |
| Q99LC8 | Translation initiation factor eIF-2B subunit alpha | Eif2b1 | 34 | 9.2 |
| Q99LD4 | COP9 signalosome complex subunit 1 | Gps1 | 53 | 5.5 |
| Q99LF4 | tRNA-splicing ligase RtcB homolog | Rtcb | 55 | 24.2 |
| Q99LU0 | Charged multivesicular body protein 1b-1 | Chmp1b1 | 22 | 6 |
| Q99NF3 | Centrosomal protein of 41 kDa | Cep41 | 41 | 7 |
| Q99PT1 | Rho GDP-dissociation inhibitor 1 | Arhgdia | 23 | 38.2 |
| Q9CQ65 | S-methyl-5'-thioadenosine phosphorylase | Mtap | 31 | 10.2 |
| Q9CQC6 | Basic leucine zipper and W2 domain-containing protein 1 | Bzw1 | 48 | 27 |
| Q9CQH7 | Transcription factor BTF3 homolog 4 | Btf3l4 | 17 | 55.7 |
| Q9CQJ6 | Density-regulated protein | Denr | 22 | 20.7 |
| Q9CQV6 | Microtubule-associated proteins 1A/1B light chain 3B | Map1lc3b | 15 | 29.6 |
| Q9CQV8 | 14-3-3 protein beta/alpha | Ywhab | 28 | 21.1 |
| Q9CR16 | Peptidyl-prolyl cis-trans isomerase D | Ppid | 41 | 26.5 |
| Q9CR29 | Coiled-coil domain-containing protein 43 | Ccdc43 | 25 | 12.2 |
| Q9CRB6 | Tubulin polymerization-promoting protein family member 3 | Tppp3 | 19 | 29 |
| Q9CRC8 | Leucine-rich repeat-containing protein 40 | Lrrc40 | 68 | 2.8 |
| Q9CRD2 | ER membrane protein complex subunit 2 | Emc2 | 35 | 10.1 |
| Q9CS42 | Ribose-phosphate pyrophosphokinase 2 | Prps2 | 35 | 23.3 |
| Q9CVB6 | Actin-related protein 2/3 complex subunit 2 | Arpc2 | 34 | 29.7 |
| Q9CWJ9 | Bifunctional purine biosynthesis protein PURH | Atic | 64 | 11.3 |
| Q9CX34 | Protein SGT1 homolog | Sugt1 | 38 | 18.8 |
| Q9CXU9 | Eukaryotic translation initiation factor 1b | Eif1b | 13 | 44.2 |
| Q9CXW3 | Calcyclin-binding protein | Cacybp | 27 | 21.8 |
| Q9CXW4 | 60S ribosomal protein L11 | Rpl11 | 20 | 12.6 |
| Q9CY64 | Biliverdin reductase A | Blvra | 34 | 7.1 |
| Q9CYR6 | Phosphoacetylglucosamine mutase | Pgm3 | 59 | 4.6 |
| Q9CYT6 | Adenylyl cyclase-associated protein 2 | Cap2 | 53 | 4.8 |
| Q9CZ30 | Obg-like ATPase 1 | Ola1 | 45 | 39.6 |
| Q9CZ44 | NSFL1 cofactor p47 | Nsfl1c | 41 | 7 |
| Q9CZD3 | Glycine--tRNA ligase | Gars | 82 | 9.6 |
| Q9CZT6 | Protein CMSS1 | Cmss1 | 32 | 7.6 |
| Q9CZU6 | Citrate synthase, mitochondrial | Cs | 52 | 7.8 |
| Q9CZW5 | Mitochondrial import receptor subunit TOM70 | Tomm70 | 68 | 8.3 |
| Q9CZX8 | 40S ribosomal protein S19 | Rps19 | 16 | 23.4 |
| Q9D051 | Pyruvate dehydrogenase E1 component subunit beta, mitochondrial | Pdhb | 39 | 12.3 |
| Q9D0I9 | Arginine--tRNA ligase, cytoplasmic | Rars | 76 | 5 |
| Q9D0K2 | Succinyl-CoA: 3-ketoacid coenzyme A transferase 1, mitochondrial | Oxct1 | 56 | 7.9 |
| Q9D0L8 | mRNA cap guanine-N7 methyltransferase | Rnmt | 53 | 5.6 |
| Q9D0M1 | Phosphoribosyl pyrophosphate synthase-associated protein 1 | Prpsap1 | 39 | 22.8 |
| Q9D0R2 | Threonine--tRNA ligase, cytoplasmic | Tars | 83 | 12.6 |
| Q9D1J3 | SAP domain-containing ribonucleoprotein | Sarnp | 24 | 20.5 |
| Q9D1P4 | Cysteine and histidine-rich domain-containing protein 1 | Chordc1 | 37 | 18.7 |
| Q9D2M8 | Ubiquitin-conjugating enzyme E2 variant 2 | Ube2v2 | 16 | 60 |
| Q9D2R0 | Acetoacetyl-CoA synthetase | Aacs | 75 | 11.8 |
| Q9D358 | Low molecular weight phosphotyrosine protein phosphatase | Acp1 | 18 | 12.7 |
| Q9D6F9 | Tubulin beta-4A chain | Tubb4a | 50 | 48.9 |
| Q9D708 | Putative uncharacterized protein | S100a16 | 14 | 10.5 |
| Q9D7G0 | Ribose-phosphate pyrophosphokinase 1 | Prps1 | 35 | 15.1 |
| Q9D7H3 | RNA 3'-terminal phosphate cyclase | RtcA | 39 | 11.2 |
| Q9D8B3 | Charged multivesicular body protein 4b | Chmp4b | 25 | 13.4 |
| Q9D8N0 | Elongation factor 1-gamma | Eef1g | 50 | 22.2 |
| Q9D8W5 | 26S proteasome non-ATPase regulatory subunit 12 | Psmd12 | 53 | 16.9 |
| Q9D8Y0 | EF-hand domain-containing protein D2 | Efhd2 | 27 | 15.8 |

TABLE 1-continued

List of microtubules associated proteins obtained after purification steps (>2 peptides per hit)

| UNIPROT ID | PROTEINS | GENES | Mol weight [kDa] | Sequence coverage [%] |
|---|---|---|---|---|
| Q9DB16 | Calcium-binding protein 39-like | Cab39l | 39 | 13.1 |
| Q9DB27 | Malignant T-cell-amplified sequence 1 | Mcts1 | 21 | 21 |
| Q9DBG3 | AP-2 complex subunit beta | Ap2b1 | 105 | 9.2 |
| Q9DBP5 | UMP-CMP kinase | Cmpk1 | 22 | 23.5 |
| Q9DCD0 | 6-phosphogluconate dehydrogenase, decarboxylating | Pgd | 53 | 18 |
| Q9DCD6 | Gamma-aminobutyric acid receptor-associated protein | Gabarap | 14 | 34.2 |
| Q9DCL9 | Multifunctional protein ADE2 | Paics | 47 | 5.9 |
| Q9DCN2 | NADH-cytochrome b5 reductase 3 | Cyb5r3 | 34 | 8 |
| Q9DD18 | D-tyrosyl-tRNA(Tyr) deacylase 1 | Dtd1 | 23 | 18.2 |
| Q9EQF6 | Dihydropyrimidinase-related protein 5 | Dpysl5 | 62 | 15.6 |
| Q9EQX4 | Allograft inflammatory factor 1-like | Aif1l | 17 | 21.3 |
| Q9ERD7 | Tubulin beta-3 chain | Tubb3 | 50 | 52.2 |
| Q9ERE7 | LDLR chaperone MESD | Mesdc2 | 25 | 26.3 |
| Q9ERQ8 | Carbonic anhydrase 7 | Ca7 | 30 | 12.9 |
| Q9ESN6 | Tripartite motif-containing protein 2 | Trim2 | 81 | 26.6 |
| Q9JHQ5 | Leucine zipper transcription factor-like protein 1 | Lztfl1 | 35 | 7.4 |
| Q9JHU4 | Cytoplasmic dynein 1 heavy chain 1 | Dync1h1 | 532 | 3.7 |
| Q9JIF0 | Protein arginine N-methyltransferase 1 | Prmt1 | 42 | 6.2 |
| Q9JJK2 | LanC-like protein 2 | Lancl2 | 51 | 8.4 |
| Q9JJZ2 | Tubulin alpha-8 chain | Tuba8 | 50 | 22.3 |
| Q9JKK7 | Tropomodulin-2 | Tmod2 | 40 | 20.8 |
| Q9JLM8 | Serine/threonine-protein kinase DCLK1 | Dclk1 | 84 | 12.3 |
| Q9JLV5 | Cullin-3 | Cul3 | 89 | 17.8 |
| Q9JM76 | Actin-related protein 2/3 complex subunit 3 | Arpc3 | 21 | 24.7 |
| Q9JMA1 | Ubiquitin carboxyl-terminal hydrolase 14 | Usp14 | 56 | 17.6 |
| Q9JMG1 | Endothelial differentiation-related factor 1 | Edf1 | 16 | 31.8 |
| Q9JMG7 | Hepatoma-derived growth factor-related protein 3 | Hdgfrp3 | 22 | 32.2 |
| Q9QUM9 | Proteasome subunit alpha type-6 | Psma6 | 27 | 31.3 |
| Q9QUP5 | Hyaluronan and proteoglycan link protein 1 | Hapln1 | 40 | 7.6 |
| Q9QUR7 | Peptidyl-prolyl cis-trans isomerase NIMA-interacting 1 | Pin1 | 18 | 37 |
| Q9QX11 | Cytohesin-1 | Cyth1 | 46 | 5 |
| Q9QXL2 | Kinesin-like protein KIF21A | Kif21a | 187 | 4.6 |
| Q9QY36 | N-alpha-acetyltransferase 10 | Naa10 | 27 | 9.4 |
| Q9QY76 | Vesicle-associated membrane protein-associated protein B | Vapb | 27 | 16 |
| Q9QYB8 | Beta-adducin | Add2 | 81 | 11.7 |
| Q9QYC0 | Alpha-adducin | Add1 | 81 | 6.9 |
| Q9QYR6 | Microtubule-associated protein 1A | Map1a | 300 | 10.7 |
| Q9QZ73 | DCN1-like protein 1 | Dcun1d1 | 30 | 10.8 |
| Q9QZD9 | Eukaryotic translation initiation factor 3 subunit I | Eif3i | 36 | 12.6 |
| Q9R0P4 | Small acidic protein | Smap | 20 | 21.5 |
| Q9R0Q6 | Actin-related protein 2/3 complex subunit 1A | Arpc1a | 42 | 17.6 |
| Q9R0Y5 | Adenylate kinase isoenzyme 1 | Ak1 | 22 | 12.9 |
| Q9R1P1 | Proteasome subunit beta type-3 | Psmb3 | 23 | 34.1 |
| Q9R1P3 | Proteasome subunit beta type-2 | Psmb2 | 23 | 12.9 |
| Q9R1P4 | Proteasome subunit alpha type-1 | Psma1 | 30 | 21.7 |
| Q9R1Q8 | Transgelin-3 | Tagln3 | 22 | 38.2 |
| Q9R1R2 | Tripartite motif-containing protein 3 | Trim3 | 81 | 14.9 |
| Q9WTN0 | Geranylgeranyl pyrophosphate synthase | Ggps1 | 35 | 9.7 |
| Q9WTX5 | S-phase kinase-associated protein 1 | Skp1 | 19 | 15.3 |
| Q9WTX6 | Cullin-1 | Cul1 | 90 | 11.1 |
| Q9WUA2 | Phenylalanine--tRNA ligase beta subunit | Farsb | 66 | 7.8 |
| Q9WUA3 | ATP-dependent 6-phosphofructokinase, platelet type | Pfkp | 85 | 9.6 |
| Q9WUA6 | RAC-gamma serine/threonine-protein kinase | Akt3 | 56 | 4.6 |
| Q9WUK2 | Eukaryotic translation initiation factor 4H | Eif4h | 27 | 16.9 |
| Q9WUM3 | Coronin-1B | Coro1b | 54 | 3.7 |
| Q9WUM4 | Coronin-1C | Coro1c | 53 | 13.7 |
| Q9WV32 | Actin-related protein 2/3 complex subunit 1B | Arpc1b | 41 | 11 |
| Q9WV55 | Vesicle-associated membrane protein-associated protein A | Vapa | 28 | 8.4 |
| Q9WV60 | Glycogen synthase kinase-3 beta | Gsk3b | 47 | 19.5 |
| Q9WVA3 | Mitotic checkpoint protein BUB3 | Bub3 | 37 | 15.6 |
| Q9WVA4 | Transgelin-2 | Tagln2 | 22 | 27.1 |
| Q9Z0H8 | CAP-Gly domain-containing linker protein 2 | Clip2 | 116 | 4.8 |
| Q9Z0N2 | Eukaryotic translation initiation factor 2 subunit 3, Y-linked | Eif2s3y | 51 | 16.7 |
| Q9Z0P5 | Twinfilin-2 | Twf2 | 39 | 5.2 |
| Q9Z130 | Heterogeneous nuclear ribonucleoprotein D-like | Hnrpdl | 34 | 10.6 |
| Q9Z140 | Copine-6 | Cpne6 | 62 | 9.3 |
| Q9Z172 | Small ubiquitin-related modifier 3 | Sumo3 | 12 | 19.1 |
| Q9Z1B3 | 1-phosphatidylinositol 4,5-bisphosphate phosphodiesterase beta-1 | Plcb1 | 138 | 19 |
| Q9Z1B7 | Mitogen-activated protein kinase 13 | Mapk13 | 42 | 5.5 |
| Q9Z1G3 | V-type proton ATPase subunit C 1 | Atp6v1c1 | 44 | 7.9 |

TABLE 1-continued

List of microtubules associated proteins obtained after purification steps (>2 peptides per hit)

| UNIPROT ID | PROTEINS | GENES | Mol weight [kDa] | Sequence coverage [%] |
|---|---|---|---|---|
| Q9Z1G4 | V-type proton ATPase 116 kDa subunit a isoform 1 | Atp6v0a1 | 96 | 2.4 |
| Q9Z1N5 | Spliceosome RNA helicase Ddx39b | Ddx39b | 49 | 26.4 |
| Q9Z1S5 | Neuronal-specific septin-3 | Sept3 | 40 | 17.7 |
| Q9Z1Z2 | Serine-threonine kinase receptor-associated protein | Strap | 38 | 12.3 |
| Q9Z2H5 | Band 4.1-like protein 1 | Epb41l1 | 98 | 3 |
| Q9Z2U0 | Proteasome subunit alpha type-7 | Psma7 | 28 | 29 |
| Q9Z2U1 | Proteasome subunit alpha type-5 | Psma5 | 26 | 27 |
| Q9Z2Y8 | Proline synthase co-transcribed bacterial homolog protein | Prosc | 30 | 12 |

One important object of the invention is the possibility of testing candidate inhibitors in crude protein extracts containing native inherent TCP activity. By native inherent activity is understood the naturally obtained enzymatic activity contained within the biological sample and which has been obtained solely by described extraction method from a specific tissue, organ of biological sample. It is important to clarify that native activity is in a natural, unadorned or unchanged state. It has not been engineered nor adapted and reflects physiologically present activity in the studied biological sample such as but not limited to a specific tissue/organ. On the other hand, purified recombinant proteins of the different identified TCPase can also be tested in the detyrosination assay.

Example 2: Validation of the TCP Activity

Before testing the different compounds of the fraction of proteins having a TCP activity (MAPs fraction), the TCP activity was assessed by use of a detyrosination assay (FIG. 4).

Material & Method

An assay involving radioactively labelled tyrosine ($^3$H—Y) was used to quantitatively determine the TCPase activity. Brain tubulin was isolated and purified and radioactively labelled with *Y by recombinant TTL. To do so, recombinant bacterially expressed purified TTL (>90% purity) was put in contact with micrograms of pig brain purified tubulin. The reaction sample was incubated for one hour at 37° C. in presence of radioactively labelled $^3$H—Y and ATP. Following incorporation of $^3$H—Y to tubulin, a polymerization cycle was performed by adding GTP and incubating for 30 min at 37° C. Next the samples are centrifuged and the obtained pellet was washed twice with PEM buffer. The resulting radioactively labelled MTs were store at −80° C. until further testing. The candidate TCPase protein was expressed and purified from bacteria using His-tagged purification strategy to at least 80% purity. After obtaining both purified recombinant TCPase candidate and radioactively labelled MTs, the proteins were put into contact and various amounts of TCPase were presented to MTs. Removal of the radioactive tyrosine by the candidate detyrosinase was measured by quantification of radioactivity in both the soluble and insoluble fraction of the reaction using a liquid scintillator counter.

To further gain insights in the potential protease that could embody the TCPase activity, the isolated MAPs from crude brain extracts were exposed to a selection of specific Cysteine, Aspartic, Metallo and Serine proteinase inhibitors were tested on the extract.

Results

As expected, when MAPs fraction was added to the microtubule sample, increased detyrosination could be observed by western blot (Δ1-tubulin), showing that the MAPs fraction contains detyrosination activity (FIG. 4). In line with previous observation, TCPase activity was found in protein extracts obtained from pig brain confirming that brain has high endogenous TCPase activity, likely in part originating from neurones.

While Serine proteases inhibitors did hardly reduce native TCPase activity in brain MAPs, metallo proteases inhibitors, such as the EDTA and EGTA chelators, all led to significant inhibition up to 50% of the total TCPase activity contained in the brain MAPs. However, cysteine protease inhibitor treatment with compounds as E64 and Iodoacetamide (irreversible cysteine inhibitor) led to a complete inhibition of TCPase activity (FIG. 5). Of note, based on these data it seems likely that various specific proteins contain TCPase activity.

Example 3: Study of the CRMP Family

As part of the identified proteins in Table I, the family of collapsing response mediator proteins (CRMPs) was found. The CRMPs family has not yet been associated with regulation of TCPase activity.

In order to establish the involvement in regulation of TCP activity of these proteins, an assay was performed with a protein extract obtained from HEK293 ectopically expressing individual HA-tagged CRMP family members. All five members of the CRMP family were cloned into pRK5-HA vector and equal amounts of plasmids were transfected into HEK293 cells in a 6-wells plate. Two days after transfection cells were collected in Laemmli lysis buffer and subjected to immunoblotting analysis using a specific Δ1-tubulin antibody. Overexpression of CRMP1 drastically increased tubulin detyrosination, whereas the other CRMPs showed no detyrosination activity (FIG. 6).

To further validate the TCPase activity observed in the overexpression experiment for CRMP1, we performed immunofluorescence analysis on U2OS cells. Equal amounts of pRK5 plasmid containing all the 5 members of the CRMP family were transfected using a polyethylenimine derivative transfection reagent. Two days after transfection cells were ethanol fixed and subjected to immunofluorescence labelling of HA tag and Δ1-tubulin (FIG. 7). All ectopically expressed CRMP proteins are labeled with HA but only CRMP1 transfected cells showed increased Δ1-tubulin staining.

An assay for evaluating knockdown of endogenous CRMP1 expression in U2OS cells by siRNA interference was also performed. U2OS cells were routinely cultured in the laboratory under standard conditions. Knockdown was obtained by transfection using INTERFERin (Polyplus) of specific RNAi sequences targeting CRMP1. Seventy two hours post-transfection, cells were collected and lysed in Laemmli buffer. Equal amounts of proteins were subjected to immunoblotting protocol. A decrease in posttranslational modification of tubulin as detyrosination and acetylation are shown to correlate with decrease in CRMP1 expression (FIG. 8).

To further validate the loss of TCPase activity observed by knockdown of CRMP1 in U2OS cells, routinely cultured cells were plated in 6-wells plate, ethanol fixed and analysed by immunofluorescence labelling. As anticipated, knockdown of CRMP1 resulted in reduction of Δ1-tubulin staining (FIG. 9).

Interestingly, depletion of CRMP1 by transfection with specific RNAi sequences resulted in cell cycle arrest in the human U2OS cells. This was observed by western blot analysis of depleted cells. Knockdown of CRMP1 resulted in increase of p21 and p53 protein levels, a marker for cell cycle arrest (FIG. 10A). This was further validated by flow cytometry analysis. Indeed, CRMP1 depleted cells showed an increase of cells with 2n bulk DNA content, indicative for a G1 arrest (FIG. 10B-C). This is particularly interesting in the context of cancerous cells that have uncontrolled cell division.

Example 4: Inhibitor Activity of Peptidic Based Inhibitors

One important object of the invention is the possibility of testing candidate inhibitor in crude protein extracts containing native inherent TCP activity. By native inherent activity is understood the naturally obtained enzymatic activity contained within the biological sample and which has been obtained solely by described extraction method from a specific tissue, organ of biological sample. According to the invention, "native activity" corresponds to natural, unadorned or unchanged state; it has not been engineered nor adapted and reflects physiologically present activity in the studied biological sample, such as but not limited to a specific tissue/organ.

The natural protruding alpha tubulin tail on the surface of the MT's was used as a base for the development of peptidic inhibitors. Among the various peptides that could be tested to validate the inhibitor activity of the peptidic inhibitors of the invention, a representative set of two peptides composed of EDY and EEY was evaluated.

Material & Method

Recombinant bacterially expressed purified TTL (>90% purity) was put in contact with micrograms of pig brain purified tubulin. The reaction sample was incubated for one hour at 37° C. in presence of radioactively labeled $^3$H—Y and ATP. Following incorporation of $^3$H—Y to tubulin, a polymerization cycle was performed by adding GTP and incubating for 30 min at 37° C. Next, the samples were centrifuged and the obtained pellet was washed twice with PEM buffer. The resulting radioactively labeled MTs were store at −80° C. until further testing. The isolated MAPs from crude brain extracts (as obtained in example 1) were contacted to the radioactively labeled MTs in absence or presence of different peptidic inhibitors or an increasing concentration of peptidic inhibitor. Release of radioactive tyrosine by native TCPase containing brain MAPs was measured by quantification of radioactivity in both the soluble and insoluble fraction of the reaction using a liquid scintillator counter.

Results

This method for selecting and designing peptidic inhibitors with different properties allows differential applications of the inhibitors based on selectivity and potency criteria. We observed that the three amino acid peptide EDY already partially blocked TCP activity in the MAPs fraction (FIG. 11A). Most interestingly, the tripeptide EEY almost fully inhibited TCP activity in this setting (FIG. 11A). To further pharmacologically describe the peptide inhibitor, a dose-response curve analysis was performed (FIG. 11B). The obtained inhibition reflected specific inhibition of TCPase by the peptidic inhibitor (FIGS. 11A and 11B).

Example 5: In Cellulo Inhibition of TCPase Activity with a Peptidic Inhibitor

To further explore the in cellulo efficacy of EEY peptide to inhibit TCP activity in a relevant model, C2C12 muscle cells were cultured and differentiated.

Myogenesis is a complex phenomenon and mechanistically linked to detyrosination status of the microtubules. Duchenne muscular dystrophy (DMD) is a severe type of muscular dystrophy and some of the altered biochemical processes are mimicked in the C2C12 muscle cell model.

Material & Method

C2C12 cells is an immortal cell line of mouse skeletal myoblasts originally derived from satellite cells from the thigh muscle cells. C2C12 cells were routinely grown at 37° C. in a CO2 incubator. Myogenic differentiation is initiated upon reaching confluence by switching the cells to medium containing 2% horse serum. Cells were collected at start of the myogenic differentiation and every two days over a period of 6 days for molecular analysis.

In addition, to assess the role of TCPase in a different model, analysis of TCPase expression in a neuronal differentiation process using neuroblastoma cell line (SH-SY5Y) was tested. SH-SY5Y cells were routinely cultured at 37° C. in a CO2 incubator prior to differentiation. Cells were resuspended in growing media and plated at low density in culture plates. The differentiation process was followed by light microscopy and clear neural phenotype could be observed at day 8. Post-mitotic SH-SY5Y cells displayed increasing number of outgrowth and neurites. Cells were collected during the neuronal differentiation process at day 0, 2, 3, 6, 7 and 10 for gene expression analysis by quantitative PCR. qPCR probes were designed using primer3 software and CRMP1 gene expression was analyzed.

Results

To further study the use of a TCPase inhibitor, C2C12 cells were treated with or without EEY peptide (FIG. 12). The protein expression of Myosin was monitored by western blotting as control for muscle differentiation. Vinculin acts as loading control. Acetylation and detyrosination of the microtubules was assessed. Whereas acetylation increases during differentiation (Ac-Tubulin) no difference in the status could be observed in the treated cells. Interestingly, detyrosination levels were increased already at day after onset of myogenic differentiation. Besides, the presence of the TCPase inhibitor clearly inhibited detyrosination (Δ-1 Tubulin), further supporting the notion that the TCPase inhibitor is cell permeable and acts on intrinsic TCPase activity.

As expected a strong induction of DDC was measured during the neural differentiation process. DDC is a marker of dopaminergic neurons and validates the neural differentiation process during the experiment (FIG. 13). As anticipated, the level of CRMP1 also increased as TCPase activity also increases during the process. This is in line with the critical role of TCPase activity in the maintenance of axonal projection. The SH-SY5Y differentiation process recapitulates many molecular mechanisms known to be dysregulated in Parkinson disease and other neurodegenerative disorders.

Example 6: Study of the Detyrosination Process of Microtubules in Muscular Dystrophy Myoblast cells were obtained from a healthy control (Ctrl) and from a patient diagnosed with Duchenne muscular dystrophy (DMD), a genetic disorder characterized by progressive muscle degeneration and weakness. DMD is caused by an absence of dystrophin, a protein that helps keep muscle cells intact.

The cells obtained from DMD patients have been sequenced and due to a genetic mutation, they lack dystrophin protein. After isolation and purification of the myoblast cells from the explants, the cells were cultured in a standard humidified tissue culture incubator at 37° C. in presence of 5% CO2. The cells were amplified in Dulbecco's Modified Eagle Medium (Gibco) supplemented with 20% fetal bovine serum (FBS), 10% horse serum, purified growth factors and antibiotics (100 U/mL penicillin and 100 µg/mL streptomycin). The serum-rich growth medium supports both proliferation and differentiation of myogenic cells. The cells were plated in a 6 cm culture dish and grown to confluency prior to myogenic differentiation. Cells were collected at indicated steps by scrapping in PBS and mild centrifugation. The PBS buffer was removed and samples were snap frozen in liquid nitrogen and kept in −80° C. freezer until analysis. All the samples contained a similar amount of cells. A denaturating Laemmli buffer (containing 2% SDS, 2,5% 2-mercaptoethanol, 10% glycerol, 0.002% bromophenol blue, 0.125 M Tris HCl, pH adjusted to 6.8) was added and the samples were boiled at 95° C. to further to denature the proteins present. After cooling, the samples were loaded on a 10% polyacrylamide gel and subjected to electrophoresis for separation and transferred to a nitrocellulose membrane (GE Healthcare). The Antibodies recognizing detyrosinated tubulin (deTyr-tub), beta tubulin (E7, hybridoma) and vinculin (Sigma) were used to detect protein levels. A secondary antibody coupled to HRP (Cell Signaling) was used for detection of the protein of interest.

The basal level of detyrosination was lower in DMD cells in the basal condition whereas after differentiation detyrosination was much higher (FIG. 14.). The observed increase in tubulin detyrosination in cells originating from a DMD patient could represent a new therapeutic opportunity.

Example 7: Study of the Detyrosination Process of Microtubules in Neurodegenerative Diseases a) Tauopathies belong to a class of neurodegenerative diseases associated with the pathological aggregation of the microtubule-associated protein (MAP) known as Tau protein in neurofibrillary tangles in the human brain. Tangles results from hyperphosphorylation of Tau protein, causing the protein to dissociate from microtubules and to form insoluble aggregates. Altered detyrosination will lead to exposure of negatively charged glutamate residues.

The human cell line SH-SY5Y is a widely used model for studying the molecular events in the pathophysiology of Alzheimer, Parkinson disease and more generally neurodegenerative diseases. Using SH-SY5Y, it is possible to drive differentiation in order to obtain neuronal morphology with long, extensively branched neurites that express neurospecific markers. The cells were cultured in Dulbecco's Modified Eagle Medium: Nutrient Mixture F-12 (DMEM/F-12) supplemented with 10% fetal bovine serum (FBS) in presence of antibiotics (100 U/mL penicillin and 100 µg/mL streptomycin). The cells were routinely passaged and cultured in a standard humidified tissue culture incubator at 37° C. in presence of 5% CO2. Prior to differentiation cells were trypsinized and counted twice using an automated cell counter (Countess II; Thermo Scientific) and 0.8×105 were plated in a 6-wells plate (Nunc). Next day, cells were washed twice with PBS and B-27 (Gibco) supplemented medium containing all-trans-retinoic acid (RA: Sigma R 2625) at 10 µM. Samples of SH-SY5Y cells ongoing neural differentiation were collected every day in a RIPA buffer (50 mM Tris HCl, 150 mM NaCl, 1.0% (v/v) NP-40, 0.5% (w/v) Sodium Deoxycholate, 1.0 mM EDTA, at a pH of 7.4), and quantitation of total protein performed using BCA kit (Thermo Fisher Scientific). A 20 µg protein sample of a total cell extract was run on 10% SDS-PAGE, transferred to nitrocellulose, and probed with each antibody.

As observed by western blot analysis, tubulin detyrosination increases during neural differentiation. By reducing the level of detyrosination, displacement of Tau from the MT's may be hampered as such reducing intracellular aggregates. b) Recent evidences converge to the essential role of the microtubule-associated proteins known as Tau that builds up in the brain during the course of the disease but acting on microtubule modifications have so far been neglected.

To further understand the role of detyrosination in the pathophysiology of Alzheimer Disease skin fibroblasts from patients carrying familial Alzheimer's Disease mutations were obtained and induced pluripotent stem cell (iPSC) generated.

The cells were maintained at the neural progenitor stage and samples were collected every day in a RIPA buffer (50 mM Tris HCl, 150 mM NaCl, 1.0% (v/v) NP-40, 0.5% (w/v) Sodium Deoxycholate, 1.0 mM EDTA, at a pH of 7.4), and quantitation of total protein performed using BCA kit (Thermo Fisher Scientific). A 20 µg protein sample of a total cell extract was run on 10% SDS-PAGE, transferred to nitrocellulose, and probed with each antibody.

Western blot analysis showed a striking increase of tubulin detyrosination in one of the cell-line carrying a genetic mutation (FIG. 16). Whereas current pharmaceutical efforts target the phosphorylation status of Tau protein itself, this observation opens a complete new window for therapeutic intervention. Pharmacological inhibition of detyrosinase act by directly regulating the level of microtubule detyrosination and as such may restore Tau binding to microtubules as well as endosomal-lysosomal processing efficiency, which is known to be defective during neurodegeneration.

Overall inhibition of detyrosination will 1) restore axonal transport which is essential for the clearance of Tau aggregates and other aggregates, and 2) reduce the level of negatively charged amino acid at the microtubule surface (detyrosinated microtubules exposed a negatively charged glutamate) leading to improved trapping of hyperphosphorylated Tau proteins. The bulky hydrophobic aromatic residues such as tyrosine have the ability to obscure the negative charges of glutamates.

Example 8: Study of the Detyrosination Process of Microtubules in Cancers

Despite the major advances in therapeutic approaches and personalized medicine, the spread of primary tumors toward distant organs and the subsequent metastatic colonization is still responsible for 90% of cancer-associated mortality. Tumors arising from epithelial tissues represent the vast majority of life-threatening cancers because of their ability to metastasize in different secondary organs. Therefore, a pressing concern in tumor biology has been the elucidation of factors and mechanisms regulating the migratory activity of these cells, tumor vascularization and colonization.

Accumulating data point out that increased tumor aggressiveness is associated with misregulation of the tyrosination/detyrosination cycle of tubulin. Increased level of tubulin detyrosination has been observed during cell migration, intravasation and in colonization suggesting a key role of this modification in metastasis.

By using CHL-1 cells that is a human melanoma cell line and HEK cells that have been demonstrated the ability to form colonies in soft agar and tumors of different size with varying frequencies in immunocompromised mice, we analyzed the use of a peptidic inhibitor to reduced taxol induced detyrosination. Cells were routinely cultured in a standard humidified tissue culture incubator at 37° C. in presence of 5% CO2 and plated in a 6-wells culture dish. The cells were treated for 2 hours with 10 µM Taxol in absence or presence of 50 µM peptidic inhibitor.

The cells were collected in a RIPA buffer (of 50 mM Tris HCl, 150 mM NaCl, 1.0% (v/v) NP-40, 0.5% (w/v) Sodium Deoxycholate, 1.0 mM EDTA, at a pH of 7.4), and quantitation of total protein performed using BCA kit (Thermo Fisher Scientific). A 20 µg protein sample of a total cell extract was run on 10% SDS-PAGE, transferred to nitrocellulose, and probed with each antibody.

Western blot analysis showed a striking decrease of taxol treated (2 hours) and consequent tubulin detyrosination in both CHL-1 and HEK cells (FIG. 17).

The invention claimed is:

1. A method of treatment of a disorder involving altered microtubule detyrosination in a subject in need thereof comprising administering to the subject in need thereof an amino-acid or peptidic based inhibitor that inhibits, at least partially, a tubulin carboxypeptidase activity, wherein the amino acid or peptidic based inhibitor is selected from the group consisting of:

- a Tyr amino-acid (Y) modified with an epoxysuccinyl group, or a peptidic moiety consisting of an amino acid sequence selected from the group consisting of EDY, and EEY, where the tyrosine residue is chemically modified with an epoxysuccinyl group;
- a peptidic moiety of 2 to 19 amino acids of the most C-terminal amino acids of SEQ ID NO:12 where the C-terminal position is a tyrosine residue chemically modified with an epoxysuccinyl group; and
- a peptidic moiety consisting of an amino acid sequence selected from the group consisting of SEQ ID NO: 12, SEQ ID NO:13, SEQ ID NO: 14, SEQ ID NO: 15, SEQ ID NO:17, and SEQ ID NO: 18, where the C-terminal position is a tyrosine residue chemically modified with an epoxysuccinyl group.

2. The method of claim 1, wherein the amino-acid based inhibitor is Epoxysuccinyl-Y (Eps-Y).

3. The method of claim 1, wherein the disorder is selected from neurodegenerative diseases, cancers, muscular dystrophies, heart diseases, vascular disorders, infertility, retinal degeneration and ciliopathies.

4. The method of claim 2, wherein the disorder is selected from neurodegenerative diseases, cancers, muscular dystrophies, heart diseases, vascular disorders, infertility, retinal degeneration and ciliopathies.

5. The method of claim 4, wherein the neurodegenerative diseases are selected from Alzheimer's disease, Parkinson's disease, psychiatric disorders, and neural disorders, and cancers are selected from colon cancer and neuroblastoma.

6. The method of claim 4, wherein the neurodegenerative diseases are selected from Alzheimer's disease and neural disorders and cancers are selected from colon cancer and neuroblastoma.

* * * * *

```
SEQUENCE LISTING

<160> NUMBER OF SEQ ID NOS: 20

<210> SEQ ID NO 1
<211> LENGTH: 494
<212> TYPE: PRT
<213> ORGANISM: Homo sapiens

<400> SEQUENCE: 1

Met Pro Leu Tyr Ser Val Thr Val Lys Trp Gly Lys Glu Lys Phe Glu
1               5                   10                  15

Gly Val Glu Leu Asn Thr Asp Glu Pro Pro Met Val Phe Lys Ala Gln
            20                  25                  30

Leu Phe Ala Leu Thr Gly Val Gln Pro Ala Arg Gln Lys Val Met Val
        35                  40                  45

Lys Gly Gly Thr Leu Lys Asp Asp Asp Trp Gly Asn Ile Lys Ile Lys
    50                  55                  60

Asn Gly Met Thr Leu Leu Met Met Gly Ser Ala Asp Ala Leu Pro Glu
65                  70                  75                  80

Glu Pro Ser Ala Lys Thr Val Phe Val Glu Asp Met Thr Glu Glu Gln
                85                  90                  95

Leu Ala Ser Ala Met Glu Leu Pro Cys Gly Leu Thr Asn Leu Gly Asn
            100                 105                 110

Thr Cys Tyr Met Asn Ala Thr Val Gln Cys Ile Arg Ser Val Pro Glu
        115                 120                 125

Leu Lys Asp Ala Leu Lys Arg Tyr Ala Gly Ala Leu Arg Ala Ser Gly
    130                 135                 140

Glu Met Ala Ser Ala Gln Tyr Ile Thr Ala Ala Leu Arg Asp Leu Phe
145                 150                 155                 160

Asp Ser Met Asp Lys Thr Ser Ser Ser Ile Pro Pro Ile Ile Leu Leu
                165                 170                 175

Gln Phe Leu His Met Ala Phe Pro Gln Phe Ala Glu Lys Gly Glu Gln
            180                 185                 190

Gly Gln Tyr Leu Gln Gln Asp Ala Asn Glu Cys Trp Ile Gln Met Met
        195                 200                 205
```

```
Arg Val Leu Gln Gln Lys Leu Glu Ala Ile Glu Asp Asp Ser Val Lys
    210             215                 220
Glu Thr Asp Ser Ser Ala Ser Ala Thr Pro Ser Lys Lys
225             230             235             240
Ser Leu Ile Asp Gln Phe Phe Gly Val Glu Phe Glu Thr Thr Met Lys
                245                 250                 255
Cys Thr Glu Ser Glu Glu Glu Val Thr Lys Gly Lys Glu Asn Gln
            260                 265             270
Leu Gln Leu Ser Cys Phe Ile Asn Gln Glu Val Lys Tyr Leu Phe Thr
        275                 280                 285
Gly Leu Lys Leu Arg Leu Gln Glu Glu Ile Thr Lys Gln Ser Pro Thr
290                 295                 300
Leu Gln Arg Asn Ala Leu Tyr Ile Lys Ser Ser Lys Ile Ser Arg Leu
305             310                 315                 320
Pro Ala Tyr Leu Thr Ile Gln Met Val Arg Phe Phe Tyr Lys Glu Lys
                325                 330                 335
Glu Ser Val Asn Ala Lys Val Leu Lys Asp Val Lys Phe Pro Leu Met
            340                 345                 350
Leu Asp Met Tyr Glu Leu Cys Thr Pro Glu Leu Gln Glu Lys Met Val
        355                 360                 365
Ser Phe Arg Ser Lys Phe Lys Asp Leu Glu Asp Lys Lys Val Asn Gln
370                 375                 380
Gln Pro Asn Thr Ser Asp Lys Lys Ser Ser Pro Gln Lys Glu Val Lys
385                 390                 395                 400
Tyr Glu Pro Phe Ser Phe Ala Asp Asp Ile Gly Ser Asn Asn Cys Gly
                405                 410                 415
Tyr Tyr Asp Leu Gln Ala Val Leu Thr His Gln Gly Arg Ser Ser Ser
            420                 425                 430
Ser Gly His Tyr Val Ser Trp Val Lys Arg Lys Gln Asp Glu Trp Ile
        435                 440                 445
Lys Phe Asp Asp Asp Lys Val Ser Ile Val Thr Pro Glu Asp Ile Leu
450                 455                 460
Arg Leu Ser Gly Gly Gly Asp Trp His Ile Ala Tyr Val Leu Leu Tyr
465                 470                 475                 480
Gly Pro Arg Arg Val Glu Ile Met Glu Glu Glu Ser Glu Gln
                485                 490

<210> SEQ ID NO 2
<211> LENGTH: 858
<212> TYPE: PRT
<213> ORGANISM: Homo sapiens

<400> SEQUENCE: 2

Met Ala Glu Leu Ser Glu Ala Leu Leu Ser Val Leu Pro Thr Ile
1               5                   10                  15
Arg Val Pro Lys Ala Gly Asp Arg Val His Lys Asp Glu Cys Ala Phe
                20                  25                  30
Ser Phe Asp Thr Pro Glu Ser Glu Gly Gly Leu Tyr Ile Cys Met Asn
            35                  40                  45
Thr Phe Leu Gly Phe Gly Lys Gln Tyr Val Arg His Phe Asn Lys
        50                  55                  60
Thr Gly Gln Arg Val Tyr Leu His Leu Arg Arg Thr Arg Arg Pro Lys
65                  70                  75                  80
Glu Glu Asp Pro Ala Thr Gly Thr Gly Asp Pro Pro Arg Lys Lys Pro
                85                  90                  95
```

```
Thr Arg Leu Ala Ile Gly Val Glu Gly Gly Phe Asp Leu Ser Glu Glu
            100                 105                 110

Lys Phe Glu Leu Asp Glu Asp Val Lys Ile Val Ile Leu Pro Asp Tyr
            115                 120                 125

Leu Glu Ile Ala Arg Asp Gly Leu Gly Gly Leu Pro Asp Ile Val Arg
            130                 135                 140

Asp Arg Val Thr Ser Ala Val Glu Ala Leu Leu Ser Ala Asp Ser Ala
145                 150                 155                 160

Ser Arg Lys Gln Glu Val Gln Ala Trp Asp Gly Glu Val Arg Gln Val
            165                 170                 175

Ser Lys His Ala Phe Ser Leu Lys Gln Leu Asp Asn Pro Ala Arg Ile
            180                 185                 190

Pro Pro Cys Gly Trp Lys Cys Ser Lys Cys Asp Met Arg Glu Asn Leu
            195                 200                 205

Trp Leu Asn Leu Thr Asp Gly Ser Ile Leu Cys Gly Arg Arg Tyr Phe
            210                 215                 220

Asp Gly Ser Gly Gly Asn Asn His Ala Val Glu His Tyr Arg Glu Thr
225                 230                 235                 240

Gly Tyr Pro Leu Ala Val Lys Leu Gly Thr Ile Thr Pro Asp Gly Ala
            245                 250                 255

Asp Val Tyr Ser Tyr Asp Glu Asp Met Val Leu Asp Pro Ser Leu
            260                 265                 270

Ala Glu His Leu Ser His Phe Gly Ile Asp Met Leu Lys Met Gln Lys
            275                 280                 285

Thr Asp Lys Thr Met Thr Glu Leu Glu Ile Asp Met Asn Gln Arg Ile
290                 295                 300

Gly Glu Trp Glu Leu Ile Gln Glu Ser Gly Val Pro Leu Lys Pro Leu
305                 310                 315                 320

Phe Gly Pro Gly Tyr Thr Gly Ile Arg Asn Leu Gly Asn Ser Cys Tyr
            325                 330                 335

Leu Asn Ser Val Val Gln Val Leu Phe Ser Ile Pro Asp Phe Gln Arg
            340                 345                 350

Lys Tyr Val Asp Lys Leu Glu Lys Ile Phe Gln Asn Ala Pro Thr Asp
            355                 360                 365

Pro Thr Gln Asp Phe Ser Thr Gln Val Ala Lys Leu Gly His Gly Leu
            370                 375                 380

Leu Ser Gly Glu Tyr Ser Lys Pro Val Pro Glu Ser Gly Asp Gly Glu
385                 390                 395                 400

Arg Val Pro Glu Gln Lys Glu Val Gln Asp Gly Ile Ala Pro Arg Met
            405                 410                 415

Phe Lys Ala Leu Ile Gly Lys Gly His Pro Glu Phe Ser Thr Asn Arg
            420                 425                 430

Gln Gln Asp Ala Gln Glu Phe Phe Leu His Leu Ile Asn Met Val Glu
            435                 440                 445

Arg Asn Cys Arg Ser Ser Glu Asn Pro Asn Glu Val Phe Arg Phe Leu
            450                 455                 460

Val Glu Glu Lys Ile Lys Cys Leu Ala Thr Glu Lys Val Lys Tyr Thr
465                 470                 475                 480

Gln Arg Val Asp Tyr Ile Met Gln Leu Pro Val Pro Met Asp Ala Ala
            485                 490                 495

Leu Asn Lys Glu Glu Leu Leu Glu Tyr Glu Lys Lys Arg Gln Ala
            500                 505                 510
```

Glu Glu Glu Lys Met Ala Leu Pro Glu Leu Val Arg Ala Gln Val Pro
            515                 520                 525

Phe Ser Ser Cys Leu Glu Ala Tyr Gly Ala Pro Glu Gln Val Asp Asp
            530                 535                 540

Phe Trp Ser Thr Ala Leu Gln Ala Lys Ser Val Ala Val Lys Thr Thr
545                 550                 555                 560

Arg Phe Ala Ser Phe Pro Asp Tyr Leu Val Ile Gln Ile Lys Lys Phe
                565                 570                 575

Thr Phe Gly Leu Asp Trp Val Pro Lys Lys Leu Asp Val Ser Ile Glu
            580                 585                 590

Met Pro Glu Glu Leu Asp Ile Ser Gln Leu Arg Gly Thr Gly Leu Gln
            595                 600                 605

Pro Gly Glu Glu Glu Leu Pro Asp Ile Ala Pro Pro Leu Val Thr Pro
            610                 615                 620

Asp Glu Pro Lys Gly Ser Leu Gly Phe Tyr Gly Asn Glu Asp Glu Asp
625                 630                 635                 640

Ser Phe Cys Ser Pro His Phe Ser Pro Thr Ser Pro Met Leu Asp
                645                 650                 655

Glu Ser Val Ile Ile Gln Leu Val Glu Met Gly Phe Pro Met Asp Ala
            660                 665                 670

Cys Arg Lys Ala Val Tyr Tyr Thr Gly Asn Ser Gly Ala Glu Ala Ala
            675                 680                 685

Met Asn Trp Val Met Ser His Met Asp Asp Pro Asp Phe Ala Asn Pro
            690                 695                 700

Leu Ile Leu Pro Gly Ser Ser Pro Gly Ser Thr Ser Ala Ala Ala
705                 710                 715                 720

Asp Pro Pro Pro Glu Asp Cys Val Thr Thr Ile Val Ser Met Gly Phe
                725                 730                 735

Ser Arg Asp Gln Ala Leu Lys Ala Leu Arg Ala Thr Asn Asn Ser Leu
            740                 745                 750

Glu Arg Ala Val Asp Trp Ile Phe Ser His Ile Asp Asp Leu Asp Ala
            755                 760                 765

Glu Ala Ala Met Asp Ile Ser Glu Gly Arg Ser Ala Ala Asp Ser Ile
            770                 775                 780

Ser Glu Ser Val Pro Val Gly Pro Lys Val Arg Asp Gly Pro Gly Lys
785                 790                 795                 800

Tyr Gln Leu Phe Ala Phe Ile Ser His Met Gly Thr Ser Thr Met Cys
                805                 810                 815

Gly His Tyr Val Cys His Ile Lys Lys Glu Gly Arg Trp Val Ile Tyr
            820                 825                 830

Asn Asp Gln Lys Val Cys Ala Ser Glu Lys Pro Pro Lys Asp Leu Gly
            835                 840                 845

Tyr Ile Tyr Phe Tyr Gln Arg Val Ala Ser
850                 855

<210> SEQ ID NO 3
<211> LENGTH: 478
<212> TYPE: PRT
<213> ORGANISM: Homo sapiens

<400> SEQUENCE: 3

Met Ala Gly Val Glu Glu Val Ala Ala Ser Gly Ser His Leu Asn Gly
1               5                   10                  15

Asp Leu Asp Pro Asp Asp Arg Glu Glu Gly Ala Ala Ser Thr Ala Glu
            20                  25                  30

```
Glu Ala Ala Lys Lys Arg Arg Lys Lys Lys Ser Lys Gly Pro
         35                  40                  45
Ser Ala Ala Gly Glu Gln Glu Pro Asp Lys Glu Ser Gly Ala Ser Val
 50                  55                  60
Asp Glu Val Ala Arg Gln Leu Glu Arg Ser Ala Leu Glu Asp Lys Glu
 65                  70                  75                  80
Arg Asp Glu Asp Asp Glu Asp Gly Asp Gly Asp Gly Asp Gly Ala Thr
                 85                  90                  95
Gly Lys Lys Lys Lys Lys Lys Lys Arg Gly Pro Lys Val Gln
             100                 105                 110
Thr Asp Pro Pro Ser Val Pro Ile Cys Asp Leu Tyr Pro Asn Gly Val
             115                 120                 125
Phe Pro Lys Gly Gln Glu Cys Glu Tyr Pro Pro Thr Gln Asp Gly Arg
         130                 135                 140
Thr Ala Ala Trp Arg Thr Thr Ser Glu Glu Lys Lys Ala Leu Asp Gln
145                 150                 155                 160
Ala Ser Glu Glu Ile Trp Asn Asp Phe Arg Glu Ala Ala Glu Ala His
                 165                 170                 175
Arg Gln Val Arg Lys Tyr Val Met Ser Trp Ile Lys Pro Gly Met Thr
             180                 185                 190
Met Ile Glu Ile Cys Glu Lys Leu Glu Asp Cys Ser Arg Lys Leu Ile
             195                 200                 205
Lys Glu Asn Gly Leu Asn Ala Gly Leu Ala Phe Pro Thr Gly Cys Ser
         210                 215                 220
Leu Asn Asn Cys Ala Ala His Tyr Thr Pro Asn Ala Gly Asp Thr Thr
225                 230                 235                 240
Val Leu Gln Tyr Asp Asp Ile Cys Lys Ile Asp Phe Gly Thr His Ile
                 245                 250                 255
Ser Gly Arg Ile Ile Asp Cys Ala Phe Thr Val Thr Phe Asn Pro Lys
             260                 265                 270
Tyr Asp Thr Leu Leu Lys Ala Val Lys Asp Ala Thr Asn Thr Gly Ile
         275                 280                 285
Lys Cys Ala Gly Ile Asp Val Arg Leu Cys Asp Val Gly Glu Ala Ile
         290                 295                 300
Gln Glu Val Met Glu Ser Tyr Glu Val Glu Ile Asp Gly Lys Thr Tyr
305                 310                 315                 320
Gln Val Lys Pro Ile Arg Asn Leu Asn Gly His Ser Ile Gly Gln Tyr
                 325                 330                 335
Arg Ile His Ala Gly Lys Thr Val Pro Ile Val Lys Gly Gly Glu Ala
             340                 345                 350
Thr Arg Met Glu Glu Gly Glu Val Tyr Ala Ile Glu Thr Phe Gly Ser
             355                 360                 365
Thr Gly Lys Gly Val Val His Asp Asp Met Glu Cys Ser His Tyr Met
         370                 375                 380
Lys Asn Phe Asp Val Gly His Val Pro Ile Arg Leu Pro Arg Thr Lys
385                 390                 395                 400
His Leu Leu Asn Val Ile Asn Glu Asn Phe Gly Thr Leu Ala Phe Cys
                 405                 410                 415
Arg Arg Trp Leu Asp Arg Leu Gly Glu Ser Lys Tyr Leu Met Ala Leu
             420                 425                 430
Lys Asn Leu Cys Asp Leu Gly Ile Val Asp Pro Tyr Pro Pro Leu Cys
             435                 440                 445
```

Asp Ile Lys Gly Ser Tyr Thr Ala Gln Phe Glu His Thr Ile Leu Leu
450                 455                 460

Arg Pro Thr Cys Lys Glu Val Val Ser Arg Gly Asp Asp Tyr
465                 470                 475

<210> SEQ ID NO 4
<211> LENGTH: 623
<212> TYPE: PRT
<213> ORGANISM: Homo sapiens

<400> SEQUENCE: 4

Met Pro Pro Lys Val Thr Ser Glu Leu Leu Arg Gln Leu Arg Gln Ala
1               5                   10                  15

Met Arg Asn Ser Glu Tyr Val Thr Glu Pro Ile Gln Ala Tyr Ile Ile
                20                  25                  30

Pro Ser Gly Asp Ala His Gln Ser Glu Tyr Ile Ala Pro Cys Asp Cys
            35                  40                  45

Arg Arg Ala Phe Val Ser Gly Phe Asp Gly Ser Ala Gly Thr Ala Ile
        50                  55                  60

Ile Thr Glu Glu His Ala Ala Met Trp Thr Asp Gly Arg Tyr Phe Leu
65                  70                  75                  80

Gln Ala Ala Lys Gln Met Asp Ser Asn Trp Thr Leu Met Lys Met Gly
                85                  90                  95

Leu Lys Asp Thr Pro Thr Gln Glu Asp Trp Leu Val Ser Val Leu Pro
            100                 105                 110

Glu Gly Ser Arg Val Gly Val Asp Pro Leu Ile Ile Pro Thr Asp Tyr
        115                 120                 125

Trp Lys Lys Met Ala Lys Val Leu Arg Ser Ala Gly His His Leu Ile
130                 135                 140

Pro Val Lys Glu Asn Leu Val Asp Lys Ile Trp Thr Asp Arg Pro Glu
                145                 150                 155                 160

Arg Pro Cys Lys Pro Leu Leu Thr Leu Gly Leu Asp Tyr Thr Gly Ile
            165                 170                 175

Ser Trp Lys Asp Lys Val Ala Asp Leu Arg Leu Lys Met Ala Glu Arg
        180                 185                 190

Asn Val Met Trp Phe Val Val Thr Ala Leu Asp Glu Ile Ala Trp Leu
    195                 200                 205

Phe Asn Leu Arg Gly Ser Asp Val Glu His Asn Pro Val Phe Phe Ser
210                 215                 220

Tyr Ala Ile Ile Gly Leu Glu Thr Ile Met Leu Phe Ile Asp Gly Asp
225                 230                 235                 240

Arg Ile Asp Ala Pro Ser Val Lys Glu His Leu Leu Leu Asp Leu Gly
                245                 250                 255

Leu Glu Ala Glu Tyr Arg Ile Gln Val His Pro Tyr Lys Ser Ile Leu
            260                 265                 270

Ser Glu Leu Lys Ala Leu Cys Ala Asp Leu Ser Pro Arg Glu Lys Val
        275                 280                 285

Trp Val Ser Asp Lys Ala Ser Tyr Ala Val Ser Glu Thr Ile Pro Lys
    290                 295                 300

Asp His Arg Cys Cys Met Pro Tyr Thr Pro Ile Cys Ile Ala Lys Ala
305                 310                 315                 320

Val Lys Asn Ser Ala Glu Ser Glu Gly Met Arg Arg Ala His Ile Lys
                325                 330                 335

Asp Ala Val Ala Leu Cys Glu Leu Phe Asn Trp Leu Glu Lys Glu Val
            340                 345                 350

```
Pro Lys Gly Gly Val Thr Glu Ile Ser Ala Ala Asp Lys Ala Glu
            355                 360                 365
Phe Arg Arg Gln Gln Ala Asp Phe Val Asp Leu Ser Phe Pro Thr Ile
370                 375                 380
Ser Ser Thr Gly Pro Asn Gly Ala Ile Ile His Tyr Ala Pro Val Pro
385                 390                 395                 400
Glu Thr Asn Arg Thr Leu Ser Leu Asp Glu Val Tyr Leu Ile Asp Ser
                405                 410                 415
Gly Ala Gln Tyr Lys Asp Gly Thr Thr Asp Val Thr Arg Thr Met His
            420                 425                 430
Phe Gly Thr Pro Thr Ala Tyr Glu Lys Glu Cys Phe Thr Tyr Val Leu
        435                 440                 445
Lys Gly His Ile Ala Val Ser Ala Ala Val Phe Pro Thr Gly Thr Lys
    450                 455                 460
Gly His Leu Leu Asp Ser Phe Ala Arg Ser Ala Leu Trp Asp Ser Gly
465                 470                 475                 480
Leu Asp Tyr Leu His Gly Thr Gly His Gly Val Gly Ser Phe Leu Asn
                485                 490                 495
Val His Glu Gly Pro Cys Gly Ile Ser Tyr Lys Thr Phe Ser Asp Glu
            500                 505                 510
Pro Leu Glu Ala Gly Met Ile Val Thr Asp Glu Pro Gly Tyr Tyr Glu
        515                 520                 525
Asp Gly Ala Phe Gly Ile Arg Ile Glu Asn Val Val Leu Val Val Pro
    530                 535                 540
Val Lys Thr Lys Tyr Asn Phe Asn Asn Arg Gly Ser Leu Thr Phe Glu
545                 550                 555                 560
Pro Leu Thr Leu Val Pro Ile Gln Thr Lys Met Ile Asp Val Asp Ser
                565                 570                 575
Leu Thr Asp Lys Glu Cys Asp Trp Leu Asn Asn Tyr His Leu Thr Cys
            580                 585                 590
Arg Asp Val Ile Gly Lys Glu Leu Gln Lys Gln Gly Arg Gln Glu Ala
        595                 600                 605
Leu Glu Trp Leu Ile Arg Glu Thr Gln Pro Ile Ser Lys Gln His
    610                 615                 620

<210> SEQ ID NO 5
<211> LENGTH: 1249
<212> TYPE: PRT
<213> ORGANISM: Homo sapiens

<400> SEQUENCE: 5

Met Ala Thr Ala Ala Thr Glu Glu Pro Phe Pro Phe His Gly Leu Leu
1               5                   10                  15
Pro Lys Lys Glu Thr Gly Ala Ala Ser Phe Leu Cys Arg Tyr Pro Glu
            20                  25                  30
Tyr Asp Gly Arg Gly Val Leu Ile Ala Val Leu Asp Thr Gly Val Asp
        35                  40                  45
Pro Gly Ala Pro Gly Met Gln Val Thr Thr Asp Gly Lys Pro Lys Ile
    50                  55                  60
Val Asp Ile Ile Asp Thr Thr Gly Ser Gly Asp Val Asn Thr Ala Thr
65                  70                  75                  80
Glu Val Glu Pro Lys Asp Gly Glu Ile Val Gly Leu Ser Gly Arg Val
                85                  90                  95
Leu Lys Ile Pro Ala Ser Trp Thr Asn Pro Ser Gly Lys Tyr His Ile
```

```
                100                 105                 110
Gly Ile Lys Asn Gly Tyr Asp Phe Tyr Pro Lys Ala Leu Lys Glu Arg
            115                 120                 125

Ile Gln Lys Glu Arg Lys Glu Lys Ile Trp Asp Pro Val His Arg Val
    130                 135                 140

Ala Leu Ala Glu Ala Cys Arg Lys Gln Glu Glu Phe Asp Val Ala Asn
145                 150                 155                 160

Asn Gly Ser Ser Gln Ala Asn Lys Leu Ile Lys Glu Glu Leu Gln Ser
                165                 170                 175

Gln Val Glu Leu Leu Asn Ser Phe Glu Lys Lys Tyr Ser Asp Pro Gly
            180                 185                 190

Pro Val Tyr Asp Cys Leu Val Trp His Asp Gly Glu Val Trp Arg Ala
        195                 200                 205

Cys Ile Asp Ser Asn Glu Asp Gly Asp Leu Ser Lys Ser Thr Val Leu
    210                 215                 220

Arg Asn Tyr Lys Glu Ala Gln Glu Tyr Gly Ser Phe Gly Thr Ala Glu
225                 230                 235                 240

Met Leu Asn Tyr Ser Val Asn Ile Tyr Asp Asp Gly Asn Leu Leu Ser
                245                 250                 255

Ile Val Thr Ser Gly Gly Ala His Gly Thr His Val Ala Ser Ile Ala
            260                 265                 270

Ala Gly His Phe Pro Glu Glu Pro Glu Arg Asn Gly Val Ala Pro Gly
        275                 280                 285

Ala Gln Ile Leu Ser Ile Lys Ile Gly Asp Thr Arg Leu Ser Thr Met
    290                 295                 300

Glu Thr Gly Thr Gly Leu Ile Arg Ala Met Ile Glu Val Ile Asn His
305                 310                 315                 320

Lys Cys Asp Leu Val Asn Tyr Ser Tyr Gly Glu Ala Thr His Trp Pro
                325                 330                 335

Asn Ser Gly Arg Ile Cys Glu Val Ile Asn Glu Ala Val Trp Lys His
            340                 345                 350

Asn Ile Ile Tyr Val Ser Ser Ala Gly Asn Asn Gly Pro Cys Leu Ser
        355                 360                 365

Thr Val Gly Cys Pro Gly Gly Thr Thr Ser Ser Val Ile Gly Val Gly
    370                 375                 380

Ala Tyr Val Ser Pro Asp Met Met Val Ala Glu Tyr Ser Leu Arg Glu
385                 390                 395                 400

Lys Leu Pro Ala Asn Gln Tyr Thr Trp Ser Ser Arg Gly Pro Ser Ala
                405                 410                 415

Asp Gly Ala Leu Gly Val Ser Ile Ser Ala Pro Gly Gly Ala Ile Ala
            420                 425                 430

Ser Val Pro Asn Trp Thr Leu Arg Gly Thr Gln Leu Met Asn Gly Thr
        435                 440                 445

Ser Met Ser Ser Pro Asn Ala Cys Gly Gly Ile Ala Leu Ile Leu Ser
    450                 455                 460

Gly Leu Lys Ala Asn Asn Ile Asp Tyr Thr Val His Ser Val Arg Arg
465                 470                 475                 480

Ala Leu Glu Asn Thr Ala Val Lys Ala Asp Asn Ile Glu Val Phe Ala
                485                 490                 495

Gln Gly His Gly Ile Ile Gln Val Asp Lys Ala Tyr Asp Tyr Leu Val
            500                 505                 510

Gln Asn Thr Ser Phe Ala Asn Lys Leu Gly Phe Thr Val Thr Val Gly
        515                 520                 525
```

```
Asn Asn Arg Gly Ile Tyr Leu Arg Asp Pro Val Gln Val Ala Ala Pro
            530                 535                 540
Ser Asp His Gly Val Gly Ile Glu Pro Val Phe Pro Glu Asn Thr Glu
545                 550                 555                 560
Asn Ser Glu Lys Ile Ser Leu Gln Leu His Leu Ala Leu Thr Ser Asn
                565                 570                 575
Ser Ser Trp Val Gln Cys Pro Ser His Leu Glu Leu Met Asn Gln Cys
            580                 585                 590
Arg His Ile Asn Ile Arg Val Asp Pro Arg Gly Leu Arg Glu Gly Leu
        595                 600                 605
His Tyr Thr Glu Val Cys Gly Tyr Asp Ile Ala Ser Pro Asn Ala Gly
    610                 615                 620
Pro Leu Phe Arg Val Pro Ile Thr Ala Val Ile Ala Ala Lys Val Asn
625                 630                 635                 640
Glu Ser Ser His Tyr Asp Leu Ala Phe Thr Asp Val His Phe Lys Pro
                645                 650                 655
Gly Gln Ile Arg Arg His Phe Ile Glu Val Pro Glu Gly Ala Thr Trp
            660                 665                 670
Ala Glu Val Thr Val Cys Ser Cys Ser Glu Val Ser Ala Lys Phe
        675                 680                 685
Val Leu His Ala Val Gln Leu Val Lys Gln Arg Ala Tyr Arg Ser His
    690                 695                 700
Glu Phe Tyr Lys Phe Cys Ser Leu Pro Glu Lys Gly Thr Leu Thr Glu
705                 710                 715                 720
Ala Phe Pro Val Leu Gly Gly Lys Ala Ile Glu Phe Cys Ile Ala Arg
                725                 730                 735
Trp Trp Ala Ser Leu Ser Asp Val Asn Ile Asp Tyr Thr Ile Ser Phe
            740                 745                 750
His Gly Ile Val Cys Thr Ala Pro Gln Leu Asn Ile His Ala Ser Glu
        755                 760                 765
Gly Ile Asn Arg Phe Asp Val Gln Ser Ser Leu Lys Tyr Glu Asp Leu
    770                 775                 780
Ala Pro Cys Ile Thr Leu Lys Asn Trp Val Gln Thr Leu Arg Pro Val
785                 790                 795                 800
Ser Ala Lys Thr Lys Pro Leu Gly Ser Arg Asp Val Leu Pro Asn Asn
                805                 810                 815
Arg Gln Leu Tyr Glu Met Val Leu Thr Tyr Asn Phe His Gln Pro Lys
            820                 825                 830
Ser Gly Glu Val Thr Pro Ser Cys Pro Leu Leu Cys Glu Leu Leu Tyr
        835                 840                 845
Glu Ser Glu Phe Asp Ser Gln Leu Trp Ile Ile Phe Asp Gln Asn Lys
    850                 855                 860
Arg Gln Met Gly Ser Gly Asp Ala Tyr Pro His Gln Tyr Ser Leu Lys
865                 870                 875                 880
Leu Glu Lys Gly Asp Tyr Thr Ile Arg Leu Gln Ile Arg His Glu Gln
                885                 890                 895
Ile Ser Asp Leu Glu Arg Leu Lys Asp Leu Pro Phe Ile Val Ser His
            900                 905                 910
Arg Leu Ser Asn Thr Leu Ser Leu Asp Ile His Glu Asn His Ser Phe
        915                 920                 925
Ala Leu Leu Gly Lys Lys Ser Ser Asn Leu Thr Leu Pro Pro Lys
    930                 935                 940
```

-continued

Tyr Asn Gln Pro Phe Phe Val Thr Ser Leu Pro Asp Asp Lys Ile Pro
945                 950                 955                 960

Lys Gly Ala Gly Pro Gly Cys Tyr Leu Ala Gly Ser Leu Thr Leu Ser
            965                 970                 975

Lys Thr Glu Leu Gly Lys Lys Ala Asp Val Ile Pro Val His Tyr Tyr
        980                 985                 990

Leu Ile Pro Pro Thr Lys Thr Lys Asn Gly Ser Lys Asp Lys Glu
        995                 1000                1005

Lys Asp Ser Glu Lys Glu Lys Asp Leu Lys Glu Glu Phe Thr Glu
    1010                1015                1020

Ala Leu Arg Asp Leu Lys Ile Gln Trp Met Thr Lys Leu Asp Ser
    1025                1030                1035

Ser Asp Ile Tyr Asn Glu Leu Lys Glu Thr Tyr Pro Asn Tyr Leu
    1040                1045                1050

Pro Leu Tyr Val Ala Arg Leu His Gln Leu Asp Ala Glu Lys Glu
    1055                1060                1065

Arg Met Lys Arg Leu Asn Glu Ile Val Asp Ala Ala Asn Ala Val
    1070                1075                1080

Ile Ser His Ile Asp Gln Thr Ala Leu Ala Val Tyr Ile Ala Met
    1085                1090                1095

Lys Thr Asp Pro Arg Pro Asp Ala Ala Thr Ile Lys Asn Asp Met
    1100                1105                1110

Asp Lys Gln Lys Ser Thr Leu Val Asp Ala Leu Cys Arg Lys Gly
    1115                1120                1125

Cys Ala Leu Ala Asp His Leu Leu His Thr Gln Ala Gln Asp Gly
    1130                1135                1140

Ala Ile Ser Thr Asp Ala Glu Gly Lys Glu Glu Gly Glu Ser
    1145                1150                1155

Pro Leu Asp Ser Leu Ala Glu Thr Phe Trp Glu Thr Thr Lys Trp
    1160                1165                1170

Thr Asp Leu Phe Asp Asn Lys Val Leu Thr Phe Ala Tyr Lys His
    1175                1180                1185

Ala Leu Val Asn Lys Met Tyr Gly Arg Gly Leu Lys Phe Ala Thr
    1190                1195                1200

Lys Leu Val Glu Glu Lys Pro Thr Lys Glu Asn Trp Lys Asn Cys
    1205                1210                1215

Ile Gln Leu Met Lys Leu Leu Gly Trp Thr His Cys Ala Ser Phe
    1220                1225                1230

Thr Glu Asn Trp Leu Pro Ile Met Tyr Pro Pro Asp Tyr Cys Val
    1235                1240                1245

Phe

<210> SEQ ID NO 6
<211> LENGTH: 365
<212> TYPE: PRT
<213> ORGANISM: Homo sapiens

<400> SEQUENCE: 6

Met Pro Gly Gly Lys Lys Val Ala Gly Gly Ser Ser Gly Ala Thr
1               5                   10                  15

Pro Thr Ser Ala Ala Ala Thr Ala Pro Ser Gly Val Arg Arg Leu Glu
            20                  25                  30

Thr Ser Glu Gly Thr Ser Ala Gln Arg Asp Glu Glu Pro Glu Glu Glu
        35                  40                  45

Gly Glu Glu Asp Leu Arg Asp Gly Val Pro Phe Val Asn Arg
 50                  55                  60

Gly Gly Leu Pro Val Asp Glu Ala Thr Trp Glu Arg Met Trp Lys His
 65                  70                  75                  80

Val Ala Lys Ile His Pro Asp Gly Glu Lys Val Ala Gln Arg Ile Arg
                 85                  90                  95

Gly Ala Thr Asp Leu Pro Lys Ile Pro Ile Pro Ser Val Pro Thr Phe
            100                 105                 110

Gln Pro Ser Thr Pro Val Pro Glu Arg Leu Glu Ala Val Gln Arg Tyr
        115                 120                 125

Ile Arg Glu Leu Gln Tyr Asn His Thr Gly Thr Gln Phe Phe Glu Ile
130                 135                 140

Lys Lys Ser Arg Pro Leu Thr Gly Leu Met Asp Leu Ala Lys Glu Met
145                 150                 155                 160

Thr Lys Glu Ala Leu Pro Ile Lys Cys Leu Glu Ala Val Ile Leu Gly
                165                 170                 175

Ile Tyr Leu Thr Asn Ser Met Pro Thr Leu Glu Arg Phe Pro Ile Ser
            180                 185                 190

Phe Lys Thr Tyr Phe Ser Gly Asn Tyr Phe Arg His Ile Val Leu Gly
        195                 200                 205

Val Asn Phe Ala Gly Arg Tyr Gly Ala Leu Gly Met Ser Arg Arg Glu
210                 215                 220

Asp Leu Met Tyr Lys Pro Ala Phe Arg Thr Leu Ser Glu Leu Val
225                 230                 235                 240

Leu Asp Phe Glu Ala Ala Tyr Gly Arg Cys Trp His Val Leu Lys Lys
                245                 250                 255

Val Lys Leu Gly Gln Ser Val Ser His Asp Pro His Ser Val Glu Gln
            260                 265                 270

Ile Glu Trp Lys His Ser Val Leu Asp Val Glu Arg Leu Gly Arg Asp
        275                 280                 285

Asp Phe Arg Lys Glu Leu Glu Arg His Ala Arg Asp Met Arg Leu Lys
290                 295                 300

Ile Gly Lys Gly Thr Gly Pro Pro Ser Pro Thr Lys Asp Arg Lys Lys
305                 310                 315                 320

Asp Val Ser Ser Pro Gln Arg Ala Gln Ser Ser Pro His Arg Asn
                325                 330                 335

Ser Arg Ser Glu Arg Arg Pro Ser Gly Asp Lys Lys Thr Ser Glu Pro
            340                 345                 350

Lys Ala Met Pro Asp Leu Asn Gly Tyr Gln Ile Arg Val
        355                 360                 365

<210> SEQ ID NO 7
<211> LENGTH: 572
<212> TYPE: PRT
<213> ORGANISM: Homo sapiens

<400> SEQUENCE: 7

Met Ser Tyr Gln Gly Lys Lys Ser Ile Pro His Ile Thr Ser Asp Arg
 1                   5                  10                  15

Leu Leu Ile Lys Gly Gly Arg Ile Ile Asn Asp Asp Gln Ser Leu Tyr
                 20                  25                  30

Ala Asp Val Tyr Leu Glu Asp Gly Leu Ile Lys Gln Ile Gly Glu Asn
            35                  40                  45

Leu Ile Val Pro Gly Gly Val Lys Thr Ile Glu Ala Asn Gly Arg Met
 50                  55                  60

Val Ile Pro Gly Gly Ile Asp Val Asn Thr Tyr Leu Gln Lys Pro Ser
65                  70                  75                  80

Gln Gly Met Thr Ala Asp Asp Phe Phe Gln Gly Thr Arg Ala Ala
            85                  90                  95

Leu Val Gly Gly Thr Thr Met Ile Ile Asp His Val Pro Glu Pro
            100                 105                 110

Gly Ser Ser Leu Leu Thr Ser Phe Glu Lys Trp His Glu Ala Ala Asp
            115                 120                 125

Thr Lys Ser Cys Cys Asp Tyr Ser Leu His Val Asp Ile Thr Ser Trp
130                 135                 140

Tyr Asp Gly Val Arg Glu Glu Leu Glu Val Leu Val Gln Asp Lys Gly
145                 150                 155                 160

Val Asn Ser Phe Gln Val Tyr Met Ala Tyr Lys Asp Val Tyr Gln Met
                165                 170                 175

Ser Asp Ser Gln Leu Tyr Glu Ala Phe Thr Phe Leu Lys Gly Leu Gly
                180                 185                 190

Ala Val Ile Leu Val His Ala Glu Asn Gly Asp Leu Ile Ala Gln Glu
            195                 200                 205

Gln Lys Arg Ile Leu Glu Met Gly Ile Thr Gly Pro Glu Gly His Ala
210                 215                 220

Leu Ser Arg Pro Glu Glu Leu Glu Ala Glu Ala Val Phe Arg Ala Ile
225                 230                 235                 240

Thr Ile Ala Gly Arg Ile Asn Cys Pro Val Tyr Ile Thr Lys Val Met
                245                 250                 255

Ser Lys Ser Ala Ala Asp Ile Ile Ala Leu Ala Arg Lys Lys Gly Pro
            260                 265                 270

Leu Val Phe Gly Glu Pro Ile Ala Ala Ser Leu Gly Thr Asp Gly Thr
            275                 280                 285

His Tyr Trp Ser Lys Asn Trp Ala Lys Ala Ala Ala Phe Val Thr Ser
    290                 295                 300

Pro Pro Leu Ser Pro Asp Pro Thr Thr Pro Asp Tyr Leu Thr Ser Leu
305                 310                 315                 320

Leu Ala Cys Gly Asp Leu Gln Val Thr Gly Ser Gly His Cys Pro Tyr
                325                 330                 335

Ser Thr Ala Gln Lys Ala Val Gly Lys Asp Asn Phe Thr Leu Ile Pro
            340                 345                 350

Glu Gly Val Asn Gly Ile Glu Glu Arg Met Thr Val Val Trp Asp Lys
            355                 360                 365

Ala Val Ala Thr Gly Lys Met Asp Glu Asn Gln Phe Val Ala Val Thr
            370                 375                 380

Ser Thr Asn Ala Ala Lys Ile Phe Asn Leu Tyr Pro Arg Lys Gly Arg
385                 390                 395                 400

Ile Ala Val Gly Ser Asp Ala Asp Val Val Ile Trp Asp Pro Asp Lys
                405                 410                 415

Leu Lys Thr Ile Thr Ala Lys Ser His Lys Ser Ala Val Glu Tyr Asn
                420                 425                 430

Ile Phe Glu Gly Met Glu Cys His Gly Ser Pro Leu Val Val Ile Ser
                435                 440                 445

Gln Gly Lys Ile Val Phe Glu Asp Gly Asn Ile Asn Val Asn Lys Gly
            450                 455                 460

Met Gly Arg Phe Ile Pro Arg Lys Ala Phe Pro Glu His Leu Tyr Gln
465                 470                 475                 480

```
Arg Val Lys Ile Arg Asn Lys Val Phe Gly Leu Gln Gly Val Ser Arg
                485                 490                 495

Gly Met Tyr Asp Gly Pro Val Tyr Glu Val Pro Ala Thr Pro Lys Tyr
            500                 505                 510

Ala Thr Pro Ala Pro Ser Ala Lys Ser Ser Pro Ser Lys His Gln Pro
            515                 520                 525

Pro Pro Ile Arg Asn Leu His Gln Ser Asn Phe Ser Leu Ser Gly Ala
            530                 535                 540

Gln Ile Asp Asp Asn Pro Arg Arg Thr Gly His Arg Ile Val Ala
545                 550                 555                 560

Pro Pro Gly Gly Arg Ser Asn Ile Thr Ser Leu Gly
                565                 570
```

<210> SEQ ID NO 8
<211> LENGTH: 572
<212> TYPE: PRT
<213> ORGANISM: Homo sapiens

<400> SEQUENCE: 8

```
Met Ser Tyr Gln Gly Lys Lys Asn Ile Pro Arg Ile Thr Ser Asp Arg
1               5                   10                  15

Leu Leu Ile Lys Gly Gly Lys Ile Val Asn Asp Asp Gln Ser Phe Tyr
                20                  25                  30

Ala Asp Ile Tyr Met Glu Asp Gly Leu Ile Lys Gln Ile Gly Glu Asn
            35                  40                  45

Leu Ile Val Pro Gly Gly Val Lys Thr Ile Glu Ala His Ser Arg Met
50                  55                  60

Val Ile Pro Gly Gly Ile Asp Val His Thr Arg Phe Gln Met Pro Asp
65                  70                  75                  80

Gln Gly Met Thr Ser Ala Asp Asp Phe Phe Gln Gly Thr Lys Ala Ala
                85                  90                  95

Leu Ala Gly Gly Thr Thr Met Ile Ile Asp His Val Val Pro Glu Pro
            100                 105                 110

Gly Thr Ser Leu Leu Ala Ala Phe Asp Gln Trp Arg Glu Trp Ala Asp
            115                 120                 125

Ser Lys Ser Cys Cys Asp Tyr Ser Leu His Val Asp Ile Ser Glu Trp
130                 135                 140

His Lys Gly Ile Gln Glu Glu Met Glu Ala Leu Val Lys Asp His Gly
145                 150                 155                 160

Val Asn Ser Phe Leu Val Tyr Met Ala Phe Lys Asp Arg Phe Gln Leu
                165                 170                 175

Thr Asp Cys Gln Ile Tyr Glu Val Leu Ser Val Ile Arg Asp Ile Gly
            180                 185                 190

Ala Ile Ala Gln Val His Ala Glu Asn Gly Asp Ile Ile Ala Glu Glu
            195                 200                 205

Gln Gln Arg Ile Leu Asp Leu Gly Ile Thr Gly Pro Glu Gly His Val
        210                 215                 220

Leu Ser Arg Pro Glu Glu Val Glu Ala Glu Val Asn Arg Ala Ile
225                 230                 235                 240

Thr Ile Ala Asn Gln Thr Asn Cys Pro Leu Tyr Ile Thr Lys Val Met
                245                 250                 255

Ser Lys Ser Ser Ala Glu Val Ile Ala Gln Ala Arg Lys Lys Gly Thr
            260                 265                 270

Val Val Tyr Gly Glu Pro Ile Thr Ala Ser Leu Gly Thr Asp Gly Ser
            275                 280                 285
```

-continued

His Tyr Trp Ser Lys Asn Trp Ala Lys Ala Ala Phe Val Thr Ser
    290                 295                 300

Pro Pro Leu Ser Pro Asp Pro Thr Thr Pro Asp Phe Leu Asn Ser Leu
305                 310                 315                 320

Leu Ser Cys Gly Asp Leu Gln Val Thr Gly Ser Ala His Cys Thr Phe
            325                 330                 335

Asn Thr Ala Gln Lys Ala Val Gly Lys Asp Asn Phe Thr Leu Ile Pro
        340                 345                 350

Glu Gly Thr Asn Gly Thr Glu Glu Arg Met Ser Val Ile Trp Asp Lys
    355                 360                 365

Ala Val Val Thr Gly Lys Met Asp Glu Asn Gln Phe Val Ala Val Thr
370                 375                 380

Ser Thr Asn Ala Ala Lys Val Phe Asn Leu Tyr Pro Arg Lys Gly Arg
385                 390                 395                 400

Ile Ala Val Gly Ser Asp Ala Asp Leu Val Ile Trp Asp Pro Asp Ser
            405                 410                 415

Val Lys Thr Ile Ser Ala Lys Thr His Asn Ser Ser Leu Glu Tyr Asn
        420                 425                 430

Ile Phe Glu Gly Met Glu Cys Arg Gly Ser Pro Leu Val Val Ile Ser
    435                 440                 445

Gln Gly Lys Ile Val Leu Glu Asp Gly Thr Leu His Val Thr Glu Gly
450                 455                 460

Ser Gly Arg Tyr Ile Pro Arg Lys Pro Phe Pro Asp Phe Val Tyr Lys
465                 470                 475                 480

Arg Ile Lys Ala Arg Ser Arg Leu Ala Glu Leu Arg Gly Val Pro Arg
            485                 490                 495

Gly Leu Tyr Asp Gly Pro Val Cys Glu Val Ser Val Thr Pro Lys Thr
        500                 505                 510

Val Thr Pro Ala Ser Ser Ala Lys Thr Ser Pro Ala Lys Gln Gln Ala
    515                 520                 525

Pro Pro Val Arg Asn Leu His Gln Ser Gly Phe Ser Leu Ser Gly Ala
530                 535                 540

Gln Ile Asp Asp Asn Ile Pro Arg Arg Thr Thr Gln Arg Ile Val Ala
545                 550                 555                 560

Pro Pro Gly Gly Arg Ala Asn Ile Thr Ser Leu Gly
            565                 570

<210> SEQ ID NO 9
<211> LENGTH: 570
<212> TYPE: PRT
<213> ORGANISM: Homo sapiens

<400> SEQUENCE: 9

Met Ser Tyr Gln Gly Lys Lys Asn Ile Pro Arg Ile Thr Ser Asp Arg
1               5                   10                  15

Leu Leu Ile Lys Gly Gly Arg Ile Val Asn Asp Asp Gln Ser Phe Tyr
            20                  25                  30

Ala Asp Ile Tyr Met Glu Asp Gly Leu Ile Lys Gln Ile Gly Asp Asn
        35                  40                  45

Leu Ile Val Pro Gly Gly Val Lys Thr Ile Glu Ala Asn Gly Lys Met
    50                  55                  60

Val Ile Pro Gly Gly Ile Asp Val His Thr His Phe Gln Met Pro Tyr
65                  70                  75                  80

Lys Gly Met Thr Thr Val Asp Asp Phe Phe Gln Gly Thr Lys Ala Ala

```
                    85                  90                  95
Leu Ala Gly Gly Thr Thr Met Ile Ile Asp His Val Val Pro Glu Pro
                100                 105                 110
Glu Ser Ser Leu Thr Glu Ala Tyr Glu Lys Trp Arg Glu Trp Ala Asp
            115                 120                 125
Gly Lys Ser Cys Cys Asp Tyr Ala Leu His Val Asp Ile Thr His Trp
        130                 135                 140
Asn Asp Ser Val Lys Gln Glu Val Gln Asn Leu Ile Lys Asp Lys Gly
145                 150                 155                 160
Val Asn Ser Phe Met Val Tyr Met Ala Tyr Lys Asp Leu Tyr Gln Val
                165                 170                 175
Ser Asn Thr Glu Leu Tyr Glu Ile Phe Thr Cys Leu Gly Glu Leu Gly
                180                 185                 190
Ala Ile Ala Gln Val His Ala Glu Asn Gly Asp Ile Ile Ala Gln Glu
                195                 200                 205
Gln Thr Arg Met Leu Glu Met Gly Ile Thr Gly Pro Glu Gly His Val
            210                 215                 220
Leu Ser Arg Pro Glu Glu Leu Glu Ala Glu Ala Val Phe Arg Ala Ile
225                 230                 235                 240
Thr Ile Ala Ser Gln Thr Asn Cys Pro Leu Tyr Val Thr Lys Val Met
                245                 250                 255
Ser Lys Ser Ala Ala Asp Leu Ile Ser Gln Ala Arg Lys Lys Gly Asn
                260                 265                 270
Val Val Phe Gly Glu Pro Ile Thr Ala Ser Leu Gly Ile Asp Gly Thr
            275                 280                 285
His Tyr Trp Ser Lys Asn Trp Ala Lys Ala Ala Phe Val Thr Ser
        290                 295                 300
Pro Pro Leu Ser Pro Asp Pro Thr Thr Pro Asp Tyr Ile Asn Ser Leu
305                 310                 315                 320
Leu Ala Ser Gly Asp Leu Gln Leu Ser Gly Ser Ala His Cys Thr Phe
                325                 330                 335
Ser Thr Ala Gln Lys Ala Ile Gly Lys Asp Asn Phe Thr Ala Ile Pro
            340                 345                 350
Glu Gly Thr Asn Gly Val Glu Glu Arg Met Ser Val Ile Trp Asp Lys
        355                 360                 365
Ala Val Ala Thr Gly Lys Met Asp Glu Asn Gln Phe Val Ala Val Thr
    370                 375                 380
Ser Thr Asn Ala Ala Lys Ile Phe Asn Leu Tyr Pro Arg Lys Gly Arg
385                 390                 395                 400
Ile Ser Val Gly Ser Asp Ser Asp Leu Val Ile Trp Asp Pro Asp Ala
                405                 410                 415
Val Lys Ile Val Ser Ala Lys Asn His Gln Ser Ala Ala Glu Tyr Asn
            420                 425                 430
Ile Phe Glu Gly Met Glu Leu Arg Gly Ala Pro Leu Val Val Ile Cys
        435                 440                 445
Gln Gly Lys Ile Met Leu Glu Asp Gly Asn Leu His Val Thr Gln Gly
    450                 455                 460
Ala Gly Arg Phe Ile Pro Cys Ser Pro Phe Ser Asp Tyr Val Tyr Lys
465                 470                 475                 480
Arg Ile Lys Ala Arg Arg Lys Met Ala Asp Leu His Ala Val Pro Arg
                485                 490                 495
Gly Met Tyr Asp Gly Pro Val Phe Asp Leu Thr Thr Thr Pro Lys Gly
            500                 505                 510
```

```
Gly Thr Pro Ala Gly Ser Ala Arg Gly Ser Pro Thr Arg Pro Asn Pro
            515                 520                 525

Pro Val Arg Asn Leu His Gln Ser Gly Phe Ser Leu Ser Gly Thr Gln
530                 535                 540

Val Asp Glu Gly Val Arg Ser Ala Ser Lys Arg Ile Val Ala Pro Pro
545                 550                 555                 560

Gly Gly Arg Ser Asn Ile Thr Ser Leu Ser
            565                 570

<210> SEQ ID NO 10
<211> LENGTH: 572
<212> TYPE: PRT
<213> ORGANISM: Homo sapiens

<400> SEQUENCE: 10

Met Ser Phe Gln Gly Lys Lys Ser Ile Pro Arg Ile Thr Ser Asp Arg
1               5                   10                  15

Leu Leu Ile Arg Gly Gly Arg Ile Val Asn Asp Asp Gln Ser Phe Tyr
            20                  25                  30

Ala Asp Val His Val Glu Asp Gly Leu Ile Lys Gln Ile Gly Glu Asn
        35                  40                  45

Leu Ile Val Pro Gly Gly Ile Lys Thr Ile Asp Ala His Gly Leu Met
50                  55                  60

Val Leu Pro Gly Gly Val Asp Val His Thr Arg Leu Gln Met Pro Val
65                  70                  75                  80

Leu Gly Met Thr Pro Ala Asp Asp Phe Cys Gln Gly Thr Lys Ala Ala
            85                  90                  95

Leu Ala Gly Gly Thr Thr Met Ile Leu Asp His Val Phe Pro Asp Thr
        100                 105                 110

Gly Val Ser Leu Leu Ala Ala Tyr Glu Gln Trp Arg Glu Arg Ala Asp
    115                 120                 125

Ser Ala Ala Cys Cys Asp Tyr Ser Leu His Val Asp Ile Thr Arg Trp
130                 135                 140

His Glu Ser Ile Lys Glu Glu Leu Glu Ala Leu Val Lys Glu Lys Gly
145                 150                 155                 160

Val Asn Ser Phe Leu Val Phe Met Ala Tyr Lys Asp Arg Cys Gln Cys
            165                 170                 175

Ser Asp Ser Gln Met Tyr Glu Ile Phe Ser Ile Ile Arg Asp Leu Gly
        180                 185                 190

Ala Leu Ala Gln Val His Ala Glu Asn Gly Asp Ile Val Glu Glu Glu
    195                 200                 205

Gln Lys Arg Leu Leu Glu Leu Gly Ile Thr Gly Pro Glu Gly His Val
210                 215                 220

Leu Ser His Pro Glu Glu Val Glu Ala Glu Ala Val Tyr Arg Ala Val
225                 230                 235                 240

Thr Ile Ala Lys Gln Ala Asn Cys Pro Leu Tyr Val Thr Lys Val Met
            245                 250                 255

Ser Lys Gly Ala Ala Asp Ala Ile Ala Gln Ala Lys Arg Arg Gly Val
        260                 265                 270

Val Val Phe Gly Glu Pro Ile Thr Ala Ser Leu Gly Thr Asp Gly Ser
    275                 280                 285

His Tyr Trp Ser Lys Asn Trp Ala Lys Ala Ala Ala Phe Val Thr Ser
290                 295                 300

Pro Pro Val Asn Pro Asp Pro Thr Thr Ala Asp His Leu Thr Cys Leu
```

```
            305                 310                 315                 320
Leu Ser Ser Gly Asp Leu Gln Val Thr Gly Ser Ala His Cys Thr Phe
                325                 330                 335
Thr Thr Ala Gln Lys Ala Val Gly Lys Asp Asn Phe Ala Leu Ile Pro
                340                 345                 350
Glu Gly Thr Asn Gly Ile Glu Arg Met Ser Met Val Trp Glu Lys
                355                 360                 365
Cys Val Ala Ser Gly Lys Met Asp Glu Asn Glu Phe Val Ala Val Thr
                370                 375                 380
Ser Thr Asn Ala Ala Lys Ile Phe Asn Phe Tyr Pro Arg Lys Gly Arg
385                 390                 395                 400
Val Ala Val Gly Ser Asp Ala Asp Leu Val Ile Trp Asn Pro Lys Ala
                405                 410                 415
Thr Lys Ile Ile Ser Ala Lys Thr His Asn Leu Asn Val Glu Tyr Asn
                420                 425                 430
Ile Phe Glu Gly Val Glu Cys Arg Gly Ala Pro Ala Val Val Ile Ser
                435                 440                 445
Gln Gly Arg Val Ala Leu Glu Asp Gly Lys Met Phe Val Thr Pro Gly
                450                 455                 460
Ala Gly Arg Phe Val Pro Arg Lys Thr Phe Pro Asp Phe Val Tyr Lys
465                 470                 475                 480
Arg Ile Lys Ala Arg Asn Arg Leu Ala Glu Ile His Gly Val Pro Arg
                485                 490                 495
Gly Leu Tyr Asp Gly Pro Val His Glu Val Met Val Pro Ala Lys Pro
                500                 505                 510
Gly Ser Gly Ala Pro Ala Arg Ala Ser Cys Pro Gly Lys Ile Ser Val
                515                 520                 525
Pro Pro Val Arg Asn Leu His Gln Ser Gly Phe Ser Leu Ser Gly Ser
                530                 535                 540
Gln Ala Asp Asp His Ile Ala Arg Arg Thr Ala Gln Lys Ile Met Ala
545                 550                 555                 560
Pro Pro Gly Gly Arg Ser Asn Ile Thr Ser Leu Ser
                565                 570

<210> SEQ ID NO 11
<211> LENGTH: 564
<212> TYPE: PRT
<213> ORGANISM: Homo sapiens

<400> SEQUENCE: 11

Met Leu Ala Asn Ser Ala Ser Val Arg Ile Leu Ile Lys Gly Gly Lys
1               5                   10                  15
Val Val Asn Asp Asp Cys Thr His Glu Ala Asp Val Tyr Ile Glu Asn
                20                  25                  30
Gly Ile Ile Gln Gln Val Gly Arg Glu Leu Met Ile Pro Gly Gly Ala
            35                  40                  45
Lys Val Ile Asp Ala Thr Gly Lys Leu Val Ile Pro Gly Gly Ile Asp
            50                  55                  60
Thr Ser Thr His Phe His Gln Thr Phe Met Asn Ala Thr Cys Val Asp
65              70                  75                  80
Asp Phe Tyr His Gly Thr Lys Ala Ala Leu Val Gly Gly Thr Thr Met
                85                  90                  95
Ile Ile Gly His Val Leu Pro Asp Lys Glu Thr Ser Leu Val Asp Ala
                100                 105                 110
```

```
Tyr Glu Lys Cys Arg Gly Leu Ala Asp Pro Lys Val Cys Cys Asp Tyr
            115                 120                 125

Ala Leu His Val Gly Ile Thr Trp Trp Ala Pro Lys Val Lys Ala Glu
130                 135                 140

Met Glu Thr Leu Val Arg Glu Lys Gly Val Asn Ser Phe Gln Met Phe
145                 150                 155                 160

Met Thr Tyr Lys Asp Leu Tyr Met Leu Arg Asp Ser Glu Leu Tyr Gln
                165                 170                 175

Val Leu His Ala Cys Lys Asp Ile Gly Ala Ile Ala Arg Val His Ala
            180                 185                 190

Glu Asn Gly Glu Leu Val Ala Glu Gly Ala Lys Glu Ala Leu Asp Leu
        195                 200                 205

Gly Ile Thr Gly Pro Glu Gly Ile Glu Ile Ser Arg Pro Glu Glu Leu
210                 215                 220

Glu Ala Glu Ala Thr His Arg Val Ile Thr Ile Ala Asn Arg Thr His
225                 230                 235                 240

Cys Pro Ile Tyr Leu Val Asn Val Ser Ser Ile Ser Ala Gly Asp Val
                245                 250                 255

Ile Ala Ala Ala Lys Met Gln Gly Lys Val Val Leu Ala Glu Thr Thr
            260                 265                 270

Thr Ala His Ala Thr Leu Thr Gly Leu His Tyr Tyr His Gln Asp Trp
        275                 280                 285

Ser His Ala Ala Ala Tyr Val Thr Val Pro Pro Leu Arg Leu Asp Thr
    290                 295                 300

Asn Thr Ser Thr Tyr Leu Met Ser Leu Leu Ala Asn Asp Thr Leu Asn
305                 310                 315                 320

Ile Val Ala Ser Asp His Arg Pro Phe Thr Thr Lys Gln Lys Ala Met
                325                 330                 335

Gly Lys Glu Asp Phe Thr Lys Ile Pro His Gly Val Ser Gly Val Gln
            340                 345                 350

Asp Arg Met Ser Val Ile Trp Glu Arg Gly Val Val Gly Gly Lys Met
        355                 360                 365

Asp Glu Asn Arg Phe Val Ala Val Thr Ser Ser Asn Ala Ala Lys Leu
370                 375                 380

Leu Asn Leu Tyr Pro Arg Lys Gly Arg Ile Ile Pro Gly Ala Asp Ala
385                 390                 395                 400

Asp Val Val Val Trp Asp Pro Glu Ala Thr Lys Thr Ile Ser Ala Ser
                405                 410                 415

Thr Gln Val Gln Gly Gly Asp Phe Asn Leu Tyr Glu Asn Met Arg Cys
            420                 425                 430

His Gly Val Pro Leu Val Thr Ile Ser Arg Gly Arg Val Val Tyr Glu
        435                 440                 445

Asn Gly Val Phe Met Cys Ala Glu Gly Thr Gly Lys Phe Cys Pro Leu
450                 455                 460

Arg Ser Phe Pro Asp Thr Val Tyr Lys Lys Leu Val Gln Arg Glu Lys
465                 470                 475                 480

Thr Leu Lys Val Arg Gly Val Asp Arg Thr Pro Tyr Leu Gly Asp Val
                485                 490                 495

Ala Val Val Val His Pro Gly Lys Lys Glu Met Gly Thr Pro Leu Ala
            500                 505                 510

Asp Thr Pro Thr Arg Pro Val Thr Arg His Gly Gly Met Arg Asp Leu
        515                 520                 525

His Glu Ser Ser Phe Ser Leu Ser Gly Ser Gln Ile Asp Asp His Val
```

Pro Lys Arg Ala Ser Ala Arg Ile Leu Ala Pro Pro Gly Gly Arg Ser
545                 550                 555                 560

Ser Gly Ile Trp

<210> SEQ ID NO 12
<211> LENGTH: 20
<212> TYPE: PRT
<213> ORGANISM: artificial sequence
<220> FEATURE:
<223> OTHER INFORMATION: Alpha 1A (Q71U36)

<400> SEQUENCE: 12

Tyr Glu Glu Val Gly Val Asp Ser Val Glu Gly Glu Gly Glu Glu
1               5                   10                  15

Gly Glu Glu Tyr
        20

<210> SEQ ID NO 13
<211> LENGTH: 20
<212> TYPE: PRT
<213> ORGANISM: artificial sequence
<220> FEATURE:
<223> OTHER INFORMATION: Alpha 1B (P68363)

<400> SEQUENCE: 13

Tyr Glu Glu Val Gly Val Asp Ser Val Glu Gly Glu Gly Glu Glu
1               5                   10                  15

Gly Glu Glu Tyr
        20

<210> SEQ ID NO 14
<211> LENGTH: 20
<212> TYPE: PRT
<213> ORGANISM: artificial sequence
<220> FEATURE:
<223> OTHER INFORMATION: Alpha 1C (Q9BQE3)

<400> SEQUENCE: 14

Lys Asp Tyr Glu Glu Val Gly Ala Asp Ser Ala Asp Gly Glu Asp Glu
1               5                   10                  15

Gly Glu Glu Tyr
        20

<210> SEQ ID NO 15
<211> LENGTH: 20
<212> TYPE: PRT
<213> ORGANISM: artificial sequence
<220> FEATURE:
<223> OTHER INFORMATION: Alpha 3C (Q13748)

<400> SEQUENCE: 15

Asp Tyr Glu Glu Val Gly Val Asp Ser Val Glu Ala Glu Ala Glu Glu
1               5                   10                  15

Gly Glu Glu Tyr
        20

<210> SEQ ID NO 16
<211> LENGTH: 20
<212> TYPE: PRT
<213> ORGANISM: artificial sequence
<220> FEATURE:
<223> OTHER INFORMATION: Alpha 3E (Q6PEY2)

```
<400> SEQUENCE: 16

Asp Cys Glu Glu Val Gly Val Asp Ser Val Glu Ala Glu Ala Glu Glu
1               5                   10                  15

Gly Glu Ala Tyr
            20

<210> SEQ ID NO 17
<211> LENGTH: 20
<212> TYPE: PRT
<213> ORGANISM: artificial sequence
<220> FEATURE:
<223> OTHER INFORMATION: Alpha 4A (P68366)

<400> SEQUENCE: 17

Glu Lys Asp Tyr Glu Glu Val Gly Ile Asp Ser Tyr Glu Asp Glu Asp
1               5                   10                  15

Glu Gly Glu Glu
            20

<210> SEQ ID NO 18
<211> LENGTH: 20
<212> TYPE: PRT
<213> ORGANISM: artificial sequence
<220> FEATURE:
<223> OTHER INFORMATION: Alpha 8 (Q9NY65)

<400> SEQUENCE: 18

Lys Asp Tyr Glu Glu Val Gly Thr Asp Ser Phe Glu Glu Asn Glu
1               5                   10                  15

Gly Glu Glu Phe
            20

<210> SEQ ID NO 19
<211> LENGTH: 15
<212> TYPE: PRT
<213> ORGANISM: artificial sequence
<220> FEATURE:
<223> OTHER INFORMATION: peptidic based inhibitor

<400> SEQUENCE: 19

Gly Val Asp Ser Val Glu Ala Glu Ala Glu Glu Gly Glu Glu Tyr
1               5                   10                  15

<210> SEQ ID NO 20
<211> LENGTH: 16
<212> TYPE: PRT
<213> ORGANISM: artificial sequence
<220> FEATURE:
<223> OTHER INFORMATION: peptidic moiety
<220> FEATURE:
<221> NAME/KEY: peptidic
<222> LOCATION: (1)..(16)
<223> OTHER INFORMATION: X1, X2, X5, X7, X9 and X13 = G, A or V; X3,
      X6, X8, X10, X11, X12, X14 and X15 = E or D; X4 = S, T, N or Q; X16 =
      Y or F

<400> SEQUENCE: 20

Xaa Xaa Xaa Xaa Xaa Xaa Xaa Xaa Xaa Xaa Xaa Xaa Xaa Xaa Xaa Xaa
1               5                   10                  15
```